(12) United States Patent
Spycher et al.

(10) Patent No.: US 12,128,110 B2
(45) Date of Patent: Oct. 29, 2024

(54) TRANSGLUTAMINASE CONJUGATION METHOD AND LINKER

(71) Applicant: Paul Scherrer Institut, Villigen PSI (CH)

(72) Inventors: Philipp Spycher, Zurich (CH); Roger Schibli, Baden (CH); Martin Behe, Gelterkinde (CH); Jori Wehrmuller, Zurich (CH)

(73) Assignee: PAUL SCHERRER INSTITUT, Villigen PSI (CH)

( * ) Notice: Subject to any disclaimer, the term of this patent is extended or adjusted under 35 U.S.C. 154(b) by 785 days.

(21) Appl. No.: 16/648,636

(22) PCT Filed: Sep. 19, 2018

(86) PCT No.: PCT/EP2018/075350
§ 371 (c)(1),
(2) Date: Mar. 18, 2020

(87) PCT Pub. No.: WO2019/057772
PCT Pub. Date: Mar. 28, 2019

(65) Prior Publication Data
US 2021/0128743 A1 May 6, 2021

(30) Foreign Application Priority Data

Sep. 19, 2017 (EP) .................................... 17191825
Jan. 19, 2018 (GB) .................................... 1800878

(51) Int. Cl.
*C07K 16/32* (2006.01)
*A61K 47/68* (2017.01)
*C07K 16/28* (2006.01)
*C12P 21/00* (2006.01)

(52) U.S. Cl.
CPC ...... *A61K 47/6855* (2017.08); *A61K 47/6803* (2017.08); *A61K 47/6889* (2017.08); *C07K 16/2878* (2013.01); *C07K 16/32* (2013.01); *C12P 21/00* (2013.01); *C07K 2317/24* (2013.01); *C07K 2317/41* (2013.01)

(58) Field of Classification Search
CPC ............ A61K 47/6803; A61K 47/6889; C07K 16/2878; C07K 16/32; C07K 2317/24; C07K 2317/41; C12P 21/00
USPC ...................................................... 424/179.1
See application file for complete search history.

(56) References Cited

U.S. PATENT DOCUMENTS

| | | | |
|---|---|---|---|
| 4,137,230 A | 1/1979 | Hashimoto et al. | |
| 4,151,042 A | 4/1979 | Higashide et al. | |
| 4,248,870 A | 2/1981 | Miyashita et al. | |
| 4,260,608 A | 4/1981 | Miyashita et al. | |
| 4,265,814 A | 5/1981 | Hashimoto et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 5,416,064 A | 5/1995 | Chari et al. | |
| 6,660,510 B2 | 12/2003 | Lin et al. | |
| 8,211,912 B2 | 7/2012 | Roulston et al. | |
| 9,427,478 B2 * | 8/2016 | Bregeon | A61K 47/6801 |
| 9,676,721 B2 | 6/2017 | Bair et al. | |
| 9,717,803 B2 | 8/2017 | Bregeon et al. | |
| 9,764,038 B2 | 9/2017 | Dennler et al. | |
| 10,132,799 B2 * | 11/2018 | Belmant | G01N 33/532 |
| 10,434,180 B2 * | 10/2019 | Bregeon | A61K 47/6801 |
| 10,639,291 B2 | 5/2020 | Hu et al. | |
| 10,675,359 B2 | 6/2020 | Dennler et al. | |
| 11,396,649 B2 | 7/2022 | Spycher et al. | |
| 2005/0256030 A1 | 11/2005 | Feng | |
| 2005/0260186 A1 | 11/2005 | Bookbinder et al. | |
| 2006/0104968 A1 | 5/2006 | Bookbinder et al. | |
| 2008/0063783 A1 | 3/2008 | Kreij et al. | |
| 2010/0143970 A1 | 6/2010 | Yokoyama et al. | |
| 2012/0270810 A1 | 10/2012 | Preiss-Bloom et al. | |
| 2014/0356385 A1 | 12/2014 | Dennler et al. | |
| 2017/0043033 A1 | 2/2017 | Strop et al. | |

(Continued)

FOREIGN PATENT DOCUMENTS

EP 2287317 A2 2/2011
EP 2777714 A1 9/2014
(Continued)

OTHER PUBLICATIONS

U.S. Appl. No. 16/319,502, 2019/0194641, filed Jan. 22, 2019 Jun 27, 2019, Philipp Rene Spycher.
(Continued)

*Primary Examiner* — Yan Xiao
(74) *Attorney, Agent, or Firm* — LATHROP GPM LLP; James H. Velema, Esq.; Michael J. Spellberg

(57) ABSTRACT

The present invention relates to a method for generating an antibody-payload conjugate by means of a microbial transglutaminase (MTG). The method comprises a step of conjugating a linker having a primary amine residue, said linker having the peptide structure (shown in N->C direction) $(Aax)_m$-$(Aax)(NH_2)$-$(Aax)_n$-B-$(Aax)_o$, or $(Aax)_m$-B-$(Aax)_n$-$(Aax)(NH2)$-$(Aax)_o$, to a Gln residue comprised in the heavy or light chain of an antibody. $Aax(NH_2)$ is an amino acid, amino acid derivative or amino acid mimetic comprising a side chain having a primary amine group.

31 Claims, 39 Drawing Sheets
Specification includes a Sequence Listing.

(56) References Cited

U.S. PATENT DOCUMENTS

| | | |
|---|---|---|
| 2017/0151341 A1 | 6/2017 | Ma et al. |
| 2018/0071402 A1 | 3/2018 | Bregeon et al. |
| 2018/0078656 A1 | 3/2018 | Steinkuhler et al. |
| 2018/0134766 A1* | 5/2018 | Larson .................. C07K 16/00 |
| 2018/0193476 A1 | 7/2018 | Dennler et al. |
| 2019/0194641 A1 | 6/2019 | Spycher et al. |
| 2022/0133904 A1 | 5/2022 | Schibli et al. |
| 2022/0333093 A1 | 10/2022 | Spycher et al. |
| 2023/0263904 A1 | 8/2023 | Spycher et al. |
| 2023/0372525 A1 | 11/2023 | Bertrand et al. |

FOREIGN PATENT DOCUMENTS

| | | |
|---|---|---|
| JP | 2006-524037 A | 10/2006 |
| JP | 2015-209426 A | 11/2015 |
| WO | WO 1994/012520 A1 | 6/1994 |
| WO | WO 1998/006692 A1 | 2/1998 |
| WO | WO 1999/005536 A1 | 2/1999 |
| WO | WO 2002/083180 A1 | 10/2002 |
| WO | 03/012068 A2 | 2/2003 |
| WO | WO 2003/012068 A2 | 2/2003 |
| WO | WO 2003/087131 A2 | 10/2003 |
| WO | WO 2004/043493 A1 | 5/2004 |
| WO | WO 2008/102007 A1 | 8/2008 |
| WO | WO 2009/012268 A1 | 1/2009 |
| WO | WO 2009/099728 A1 | 8/2009 |
| WO | WO 2010/115629 A2 | 10/2010 |
| WO | WO 2010/115630 A2 | 10/2010 |
| WO | 2011/119484 A1 | 9/2011 |
| WO | WO 2012/041504 A1 | 4/2012 |
| WO | WO 2012/047724 A1 | 4/2012 |
| WO | 2012/059882 A2 | 5/2012 |
| WO | WO 2012/119787 A1 | 9/2012 |
| WO | 2013/040142 A2 | 3/2013 |
| WO | 2013/049830 A2 | 4/2013 |
| WO | WO 2013/092983 A2 | 6/2013 |
| WO | WO 2013/092998 A1 | 6/2013 |
| WO | 2014140300 A1 | 9/2014 |
| WO | WO 2014/135282 A1 | 9/2014 |
| WO | 2014/202775 A1 | 12/2014 |
| WO | WO 2015/015448 A2 | 2/2015 |
| WO | WO 2015/054060 A1 | 4/2015 |
| WO | WO 2015/097267 A1 | 7/2015 |
| WO | WO 2015/162563 A1 | 10/2015 |
| WO | WO 2015/191883 A1 | 12/2015 |
| WO | WO 2016/030791 A1 | 3/2016 |
| WO | 2016100735 A1 | 6/2016 |
| WO | WO 2016/128410 A1 | 8/2016 |
| WO | 2016144608 A1 | 9/2016 |
| WO | 2016/207090 A2 | 12/2016 |
| WO | WO 2017/025179 A1 | 2/2017 |
| WO | WO 2017/106643 A1 | 6/2017 |
| WO | WO 2019/030223 A1 | 2/2019 |
| WO | WO 2019/057772 A1 | 3/2019 |
| WO | WO 2019/082020 A1 | 5/2019 |
| WO | WO 2020/188061 A1 | 9/2020 |

OTHER PUBLICATIONS

U.S. Appl. No. 17/435,356, filed Mar. 19, 2020, Roger Schibli.
International Search Report and Written Opinion for PCT/EP2018/075350 issued by the EPO dated Jan. 28, 2019.
GB Search Report for GB1800878.9 issued by the British Patent Office Oct. 9, 2018.
Dorywalska, Magdalena et al., "Molecular Basis of Valine-Citrulline-PABC Linker Instability in Site-Specific ADCs 3 and Its Mitigation by Linker Design", Molecular Cancer Therapeutics, vol. 15(5), May 2016, pp. 958-970.
De Young et al., "Transglutaminase Activity in Human and Rabbit Ear Comedogenesis: A Histochemical Study", Journal of Investigative Dermatology, 1984, 82(3): 275-279.
Fornera et al., "Immobilization of Peroxidase on SiO2 Surfaces with the Help of a Dendronized Polymer and the Avidin-Biotin System", Macromolecular Bioscience, Aug. 2011, 11(8): 1052-1067.
International Search Report and Written Opinion for PCT International Patent Application No. PCT/EP2020/057697, dated Jun. 16, 2020.
International Search Report and Written Opinion for PCT International Patent Application No. PCT/EP2014/067403, dated Oct. 25, 2017.
Jeger et al., "Site-specific and stoichiometric modification of antibodies by bacterial transglutaminase", Agnew Chem Int Ed Engl., Dec. 17, 2010, 49(51): 9995-9997.
Kato et al. "Peptide-binding assessment using mass spectrometry as a new screening method for skin sensitization", J Toxicol Sci., Feb. 2003, 28(1): 19-24.
Khew et al., "Characterization of amine donor and acceptor sites for tissue type transglutaminase using a sequence from the C-terminus of human fibrillin-1 and the N-terminus of osteonectin", Biomaterials, Jun. 2010, 31(16): 4600-4608.
Lhospice et al., "Site-Specific Conjugation of Monomethyl Auristatin E to Anti-CD30 Antibodies Improves Their Pharmacokinetics and Therapeutic Index in Rodent Models", Mol Pharm., Jun. 2015, 12(6): 1863-1871.
Maude et al., "Peptide Synthesis and Self-Assembly", Peptide-Based Materials, Topics in Current Chemistry 310, Jan. 10, 2012, p. 62.
Mindt et al., "Modification of Different IgG1 Antibodies via Glutamine and Lysine using Bacterial and Human Tissue Transglutaminase", Bioconjugate Chem., 2008, 19(1): 271-278.
New Zealand Search and Examination Report for New Zealand Patent Application No. 762376, dated Feb. 1, 2022.
Oh et al., "Characteristics of an immobilized form of transglutaminase: A possible increase in substrate specificity by selective interaction with a protein spacer", Journ Agric Food Chem., 1993, 41(8): 1337-1342.
Roig et al., "Biotechnology and applied biology section applications of immobilized enzymes", Biochemical Education, Oct. 1987, 15(4): 198-208.
Spycher et al., "Dual, Site-Specific Modification of Antibodies by Using Solid-Phase Immobilized Microbial Transglutaminase", Chembiochem., Oct. 5, 2017, 18(19): 1923-1927.
Strop et al., "Location Matters: Site of Conjugation Modulates Stability and Pharmacokinetics of Antibody Drug Conjugates", Chemistry & Biology, Feb. 21, 2013, 20: pp. 161-167.
Tanaka et al., "N-terminal glycine-specific protein conjugation catalyzed by microbial transglutaminase", FEBS Letters, 579(10): 2092-2096.
Yuan et al. "Tissue transglutaminase 2 inhibition promotes cell death and chemosensitivity in glioblastomas", Mol. Cancer Ther., Sep. 2005, 4(9): 1293-1302.
Dennler, "Microbial Transglutaminase as a Versatile Tool for Site-Specific Protein Modification", Doctoral Thesis, 2015, ETH Zürich, Dissertation No. 22512.
International Search Report and Written Opinion for PCT International Patent Application No. PCT/EP2018/075350, dated Jan. 28, 2019.
Zhang et al., "A Rigid, Chiral, Dendronized Polymer with a Thermally Stable, Right-Handed Helical Conformation", Chemistry A European Journal, Aug. 8, 2008, 14(23): 6924-6934.
Zhou et al., "The microbial transglutaminase immobilization on carboxylated poly(N-isopropylacrylamide) for thermoresponsivity", Enzyme and Microbial Technology, 2016, vol. 87-88, pp. 44-51.
U.S. Appl. No. 16/319,502 2019/0194641 U.S. Pat. No. 11,396,649, filed Jan. 22, 2019 Jun. 27, 2019 Jul. 26, 2022, Philipp Rene Spycher, Site-Specific Conjugation to Antibody Lysine Residues With Solid-Phase Immobilized Microbial Translutaminase MTG and MTG in Solution.
U.S. Appl. No. 17/704,960 2022/0333093, filed Mar. 25, 2022 Oct. 20, 2022, Philipp Rene Spycher, Site-Specific Conjugation to Antibody Lysine Residues With Solid-Phase Immobilized Microbial Transglutaminase MTG and MTG in Solution.
U.S. Appl. No. 17/435,356 2022/0133904, filed Mar. 19, 2020 May 5, 2022, Roger Schibli, Transglutaminase Conjugation Method With a Glycine Based Linker.

(56) References Cited

OTHER PUBLICATIONS

Agard et al., "A Comparative Study of Bioorthogonal Reactions with Azides", ACS Chem. Biol., 2006, 1: 644-648.
Amant et al., "A Reactive Antibody Platform for One-Step Production of Antibody-Drug Conjugates through a Diels-Alder Reaction with Maleimide", Bioconjugate Chem, 2019, 30(9): 2340-2348.
Amant et al., "Tuning the Diels-Alder Reaction for Bioconjugation to Maleimide Drug-Linkers", Bioconjugate Chem., 2018, 29(7): 2406 2414.
Amsberry et al., "The lactonization of 2'-hydroxyhydrocinnamic acid amides: a potential prodrug for amines", J. Org. Chem., 1990, 55: 5867.
Azhdarinia et al., "Dual-Labeling Strategies for Nuclear and Fluorescence Molecular Imaging: A Review and Analysis", Mol Imaging Biol., 2011, 14(3): 261-276.
Balhorn et al., "Hexa-arginine enhanced uptake and residualization of selective high affinity ligands by Raji lymphoma cells", Molecular Cancer, 2009, 8(25): 1-9.
Bargh et al., "Cleavable linkers in antibody-drug conjugates", Chem Soc Rev., Aug. 12, 2019, 48(16): 4361-4374.
Baskin et al., "Copper-free click chemistry for dynamic in vivo imaging", PNAS, 2007, 104(43): 16793-16797.
Benjamin et al., "Thiolation of Q295: Site-Specific Conjugation of Hydrophobic Payloads without the Need for Genetic Engineering", Mol. Pharmaceutics, 2019, 16: 2795-2807.
Blackman et al., "The Tetrazine Ligation: Fast Bioconjugation based on Inverse-electron-demand Diels-Alder Reactivity", Journal of the American Chemical Society, 2008, 130(41): 13518-13519.
Bodero et al., "Synthesis and biological evaluation of RGD and isoDGR peptidomimetic-a-amanitin conjugates for tumor-targeting", Beilstein J. Org. Chem., 2018, 14: 407 415.
Kontermann et al., "Bispecific antibodies", Drug Discov Today, 2015, 20(7): 838-847.
Costoplus et al., "Peptide-Cleavable Self-immolative Maytansinoid Antibody-Drug Conjugates Designed to Provide Improved Bystander Killing", ACS Med. Chem. Lett., 2019, 10(10): 1393-1399.
Dal Corso et al., "Innovative Linker Strategies for Tumor-Targeted Drug Conjugates", Chemistry, 2019, 25(65): 14740-14757.
Dickgiesser et al., "Site-Specific Conjugation of Native Antibodies Using Engineered Microbial Transglutaminases", Bioconjug Chem., Mar. 12, 2020, 31(4): 1070-1076.
Dokter et al., "Preclinical profile of the HER2-targeting ADC SYD983/SYD985: introduction of a new duocarmycin-based linker-drug platform", Mol Cancer Ther., Nov. 2014, 13(11): 2618-2629.
Doronina et al., "Enhanced activity of monomethylauristatin F through monoclonal antibody delivery: effects of linker technology on efficacy and toxicity", Bioconjug Chem., Jan. 2006, 17(1): 114-124.
Dorywalska et al., "Site-Dependent Degradation of a Non-Cleavable Auristatin-Based Linker-Payload in Rodent Plasma and Its Effect on ADC Efficacy", PLoS One, 2015, 10(7): e0132282.
Dubowchik et al., "Cathepsin B-labile dipeptide linkers for lysosomal release of doxorubicin from internalizing immunoconjugates: model studies of enzymatic drug release and antigen-specific in vitro anticancer activity", Bioconjug Chem, 2002, 13(4): 855-869.
Great Britain Search Report for Great Britain Patent Application No. GB1800878.9, dated Oct. 9, 2018.
Hay et al., "A 2-nitroimidazole carbamate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT", Bioorg. Med. Chem. Lett., 1999, 9(15): 2237-2242.
Higashide et al., "Ansamitocin, a group of novel maytansinoid antibiotics with antitumour properties from Nocardia", Nature, 1977, 270: 721-722.
Houghton et al., "Site-specifically labeled CA19.9-targeted immunoconjugates for the PET, NIRF, and multimodal PET/NIRF imaging of pancreatic cancer", PNAS USA, Dec. 29, 2015, 112(52): 15850-15855.

Huang et al., "Characterization of antibody-drug conjugates by mass spectrometry: advances and future trends", Drug Discover Today, 2016, 21(5): 850-855.
Huggins et al., "Site Selective Antibody-Oligonucleotide Conjugation via Microbial Transglutaminase", Molecules, Sep. 10, 2019, 24(18): 3287.
International Search Report and Written Opinion for PCT International Patent Application No. PCT/EP2021/075831, dated Dec. 14, 2021.
International Search Report and Written Opinion for PCT International Patent Application No. PCT/EP2021/079560, dated Feb. 8, 2022.
International Search Report and Written Opinion for PCT International Patent Application No. PCT/EP2022/079787, dated Feb. 13, 2023.
Kawai et al., "Chemical Modification of Ansamitocins. III. Synthesis and Biological Effects of 3-Acyl Esters of Maytansinol", Chem. Pharm Bull., 1984, vol. 32(9): 3441-3451.
Kehrer et al., "Modulation of camptothecin analogs in the treatment of cancer: a review", Anticancer Drugs, 2001, 12(2): 89-105.
Kieliszek, "Microbial transglutaminase and its application in the food industry. A review", Folia Microbiol (Praha), 2014, 59(3): 241-250.
Kingsbury et al., "A novel peptide delivery system involving peptidase activated prodrugs as antimicrobial agents. Synthesis and biological activity of peptidyl derivatives of 5-fluorouracil", J. Med. Chem., 1984, 27(11): 1447-1451.
Kolb et al., "The growing impact of click chemistry on drug discovery", Drug Discov Today, Dec. 15, 2003, 8(24): 1128-1137.
Kupchan et al., "Tumor inhibitors. 124. Structural requirements for antileukemic activity among the naturally occurring and semisynthetic maytansinoids", J. Med. Chem., 1978, 21(1): 31-37.
Lambert et al., "Antibody-Drug Conjugates for Cancer Treatment", Annu. Rev. Med., 2018, 69: 191 207.
Levengood et al., "Orthogonal Cysteine Protection Enables Homogeneous Multi-Drug Antibody-Drug Conjugates", Angewandte Chem Int Ed Engl., Jan. 16, 2017, 56(3): 733-737.
Li et al., "Synthesis and Evaluation of Camptothecin Antibody-Drug Conjugates", ACS Med Chem. Lett., 2019, 10(10): 1386-1392.
Lyon et al., "Reducing hydrophobicity of homogeneous antibody-drug conjugates improves pharmacokinetics and therapeutic index", Nat Biotechnol, 2015, 33: 733-735.
MacKenzie et al., "Strain-promoted cycloadditions involving nitrones and alkynes-rapid tunable reactions for bioorthogonal labeling", Curr Opin Chem Biol., 2014, 21: 81-88.
Nakada et al., "Novel antibody drug conjugates containing exatecan derivative-based cytotoxic payloads", Bioorg Med Chem Lett., Mar. 15, 2016, 26(6): 1542-1545.
Nicolaou et al., "Chemistry and biology of natural and designed enediynes", PNAS, 1993, 90(13): 5881-5888.
Ning et al., "Protein Modification by Strain-Promoted Alkyne-Nitrone Cycloaddition", Angewandte Chemie International Edition, 2010, 49(17): 3065-3068.
Nunes et al., "Use of a next generation maleimide in combination with THIOMABTM antibody technology delivers a highly stable, potent and near homogeneous THIOMABTM antibody-drug conjugate (TDC)", RSC Adv., 2017, 7: 24828-24832.
Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker", Bioconjugate Chem, 2019, 30(7): 1957-1968.
Rodrigues et al., "Synthesis and p-lactamase-mediated activation of a cephalosporin-taxol prodrug", Chemistry Biology, 1995, 2: p. 223.
Salomon et al., "Optimizing Lysosomal Activation of Antibody-Drug Conjugates (ADCs) by Incorporation of Novel Cleavable Dipeptide Linkers", Mol Pharm., 2019, 16(12): 4817-4825.
Sletten et al., "A Bioorthogonal Quadricyclane Ligation", J Am Chem Soc, 2011, 133(44): 17570-17573.
Smith et al., "The Enediyne Antibiotics", J. Med. Chem., 1996, 39(11): 2103-2117.

(56) References Cited

OTHER PUBLICATIONS

Sonzini et al., "Improved Physical Stability of an Antibody-Drug Conjugate Using Host-Guest Chemistry", Bioconjug Chem., Jan. 15, 2020, 31(1): 123-129.
Staben et al., "Targeted drug delivery through the traceless release of tertiary and heteroaryl amines from antibody-drug conjugates", Nature Chemistry, Oct. 17, 2016, 8: 1112-1119.
Stöckmann et al., "Exploring isonitrile-based click chemistry for ligation with biomolecules", Organic & Biomolecular Chemistry, 2011, 21: 7303-7305.
Strop et al., "RN927C, a Site-Specific Trop-2 Antibody-Drug Conjugate (ADC) with Enhanced Stability, Is Highly Efficacious in Preclinical Solid Tumor Models", Molecular Cancer Therapeutics, Aug. 31, 2016, 15(11): 2698-2708.
Strop et al., "Versatility of Microbial Transglutaminase", Bioconjugate Chemistry, 2014, 25(5): 855-862.
Su et al., "Modulating Antibody-Drug Conjugate Payload Metabolism by Conjugation Site and Linker Modification", Bioconjugate Chem., 2018, 29(4): 1155-1167.
Subedi et al., "The Structural Role of Antibody N-Glycosylation in Receptor Interactions", Structure, 2015, 23(9): 1573-1583.
Tsesmetzis et al., "Nucleobase and Nucleoside Analogues: Resistance and Re-Sensitisation at the Level of Pharmacokinetics, Pharmacodynamics and Metabolism", Cancers, 2018, 10(7): 240.
Walker et al., "Cleavage behavior of calicheamicin gamma 1 and calicheamicin T", PNAS USA, 1992, 89(10): 4608-4612.
Yarema et al., "Metabolic Delivery of Ketone Groups to Sialic Acid Residues. Application to Cell Surface Glycoform Engineering", Journal of Biological Chemistry, Nov. 1998, 273(47): 31168-31179.
Zhang et al., "Multifunctional Tumor-Targeting Cathepsin B-Sensitive Gemcitabine Prodrug Covalently Targets Albumin in Situ and Improves Cancer Therapy", Bioconjugate Chem., 2018, 29(6): 1852-1858.
Zhao et al., "Recent advances of antibody drug conjugates for clinical applications", Acta Pharmaceutica Sinica B, 2020, 10(9): 1589-1600.
Zheng et al., "The impact of glycosylation on monoclonal antibody conformation and stability", Mabs-Austin, 2011, 3(6): 568-576.
European Examination Report for European Patent Application No. 17742684.8, mailed Nov. 6, 2023.
Kamiya et al., "S-peptide as a potent peptidyl linker for protein cross-linking by microbial transglutaminase from Streptomyces mobaraensis," Bioconj Chem., Mar.-Apr. 2003, 14(2): 351-357.
Plagmann et al., "Transglutaminase-catalyzed covalent multimerization of Camelidae anti-human TNF single domain antibodies improves neutralizing activity," J Biotechnol., Jun. 15, 2009, 142(2): 170-178.
Takazawa et al., "Enzymatic labeling of a single chain variable fragment of an antibody with alkaline phosphatase by microbial transglutaminase," Biotechnol Bioeng., May 20, 2004, 86(4): 399-404.

* cited by examiner

Figure 5
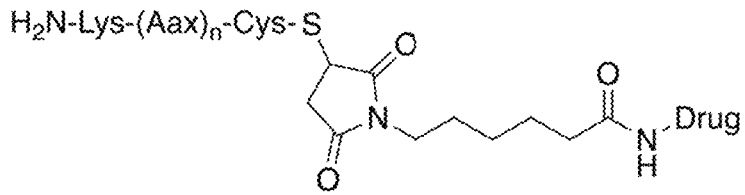
maleimidocaproyl (mc)
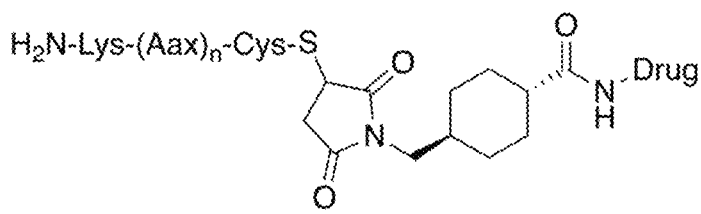
maleimidomethyl cyclohexane-1-carboxylate (mcc)
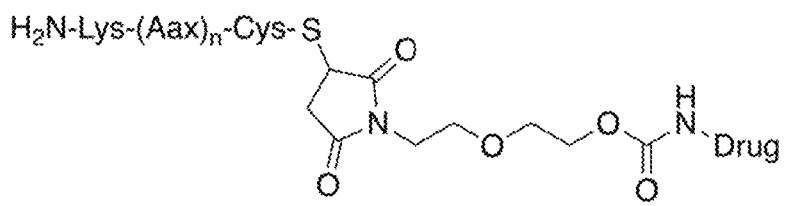
mc-like linker used in SYD985
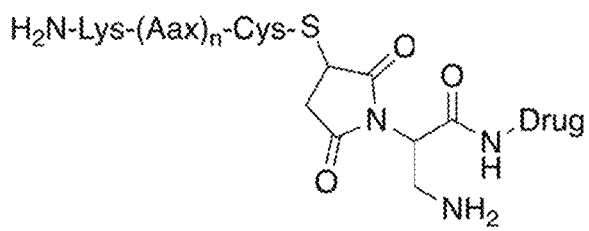
self-stabilizing maleimide

Stucture 1
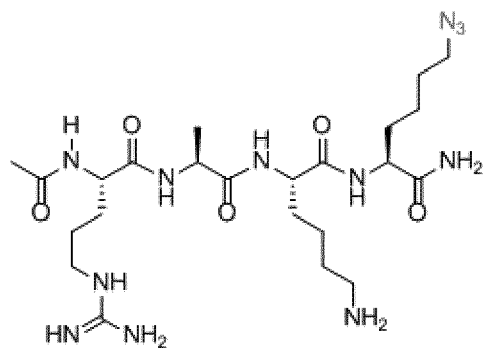
Stucture 2
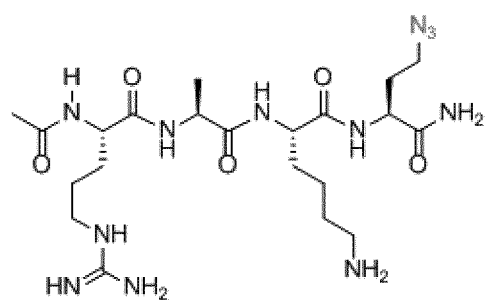
Stucture 3
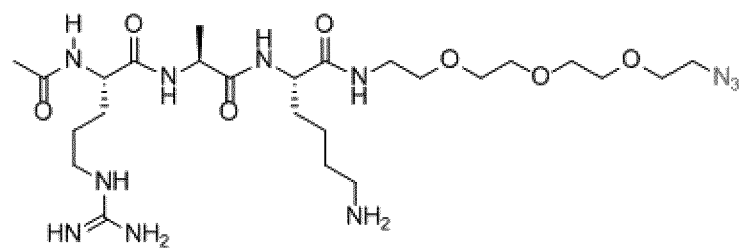
Stucture 4
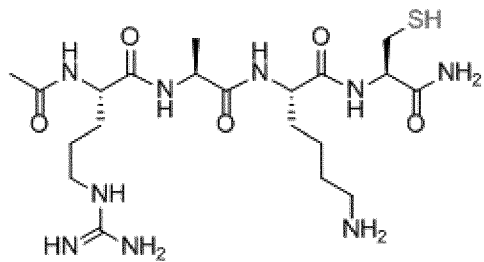
Fig. 9

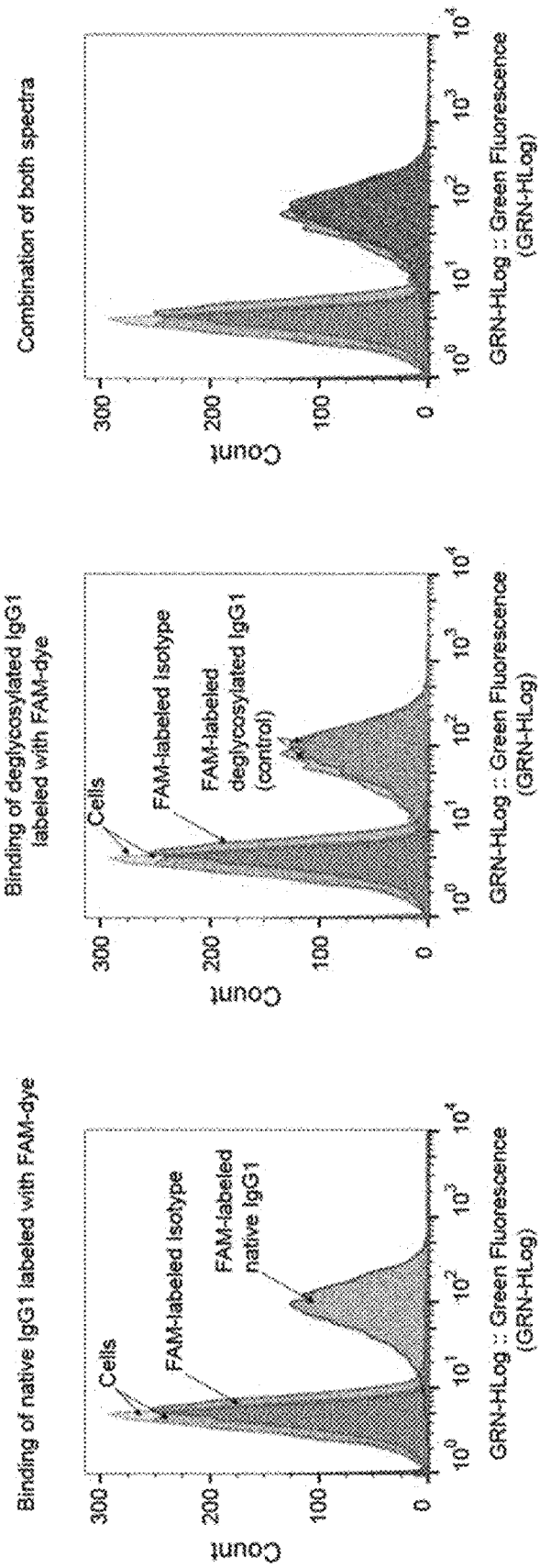

| IMGT unique numbering for C-DOMAIN | CH2 IGHG1 amino acid translation J00228 (1) | IMGT exon numbering 1-110 | Eu numbering [1] (1) (110 aa) (2) 231-340 | Kabat numbering [2] | Strands, turns and loops for C-DOMAIN (5) |
|---|---|---|---|---|---|
| 1,8 | - | - | - | - | |
| 1,7 | - | - | - | - | |
| 1,6 | (A) | 1 | 231 | 244 | |
| 1,5 | P | 2 | 232 | 245 | |
| 1,4 | E | 3 | 233 | 246 | |
| 1,3 | L | 4 | 234 | 247 | |
| 1,2 | L | 5 | 235 | 248 | |
| 1,1 | G | 6 | 236 | 249 | |
| 1 | G | 7 | 237 | 250 | |
| 2 | P | 8 | 238 | 251 | |
| 3 | S | 9 | 239 | 252 | |
| 4 | V | 10 | 240 | 253 | |
| 5 | F | 11 | 241 | 254 | |
| 6 | L | 12 | 242 | 255 | |
| 7 | F | 13 | 243 | 256 | |
| 8 | P | 14 | 244 | 257 | A-STRAND |
| 9 | P | 15 | 245 | 258 | |
| 10 | K | 16 | 246 | 259 | |
| 11 | P | 17 | 247 | 260 | |
| 12 | K | 18 | 248 | 261 | |
| 13 | D | 19 | 249 | 262 | |
| 14 | T | 20 | 250 | 263 | |
| 15 | L | 21 | 251 | 264 | |
| 15,1 | M | 22 | 252 | 265 | |
| 15,2 | I | 23 | 253 | 266 | AB-TURN |
| 15,3 | - | - | - | - | |
| 16 | S | 24 | 254 | 267 | |
| 17 | R | 25 | 255 | 268 | |
| 18 | T | 26 | 256 | 269 | |
| 19 | P | 27 | 257 | 270 | |
| 20 | E | 28 | 258 | 271 | |
| 21 | V | 29 | 259 | 272 | B-STRAND |
| 22 | T | 30 | 260 | 273 | |
| 23 | C | 31 | 261 | 274 | |
| 24 | V | 32 | 262 | 275 | |
| 25 | V | 33 | 263 | 276 | |
| 26 | V | 34 | 264 | 277 | |
| 27 | D | 35 | 265 | 278 | |
| 28 | V | 36 | 266 | 279 | |
| 29 | S | 37 | 267 | 280 | |
| 30 | H | 38 | 268 | 281 | |
| 31 | E | 39 | 269 | 282 | BC-LOOP |
| 34 | D | 40 | 270 | 283 | |
| 35 | P | 41 | 271 | 284 | |
| 36 | E | 42 | 272 | 285 | |
| 37 | V | 43 | 273 | 286 | |
| 38 | K | 44 | 274 | 287 | |
| 39 | F | 45 | 275 | 288 | |
| 40 | N | 46 | 276 | 289 | |
| 41 | W | 47 | 277 | 290 | |
| 42 | Y | 48 | 278 | 291 | C-STRAND |
| 43 | V | 49 | 279 | 292 | |
| 44 | D | 50 | 280 | 295 | |
| 45 | G | 51 | 281 | 296 | |
| 45,1 | V | 52 | 282 | 299 | |
| 45,2 | E | 53 | 283 | 300 | |
| 45,3 | V | 54 | 284 | 301 | |
| 45,4 | H | 55 | 285 | 302 | CD-STRAND |
| 45,5 | - | - | - | - | |
| 45,6 | - | - | - | - | |
| 45,7 | - | - | - | - | |
| 77 | N | 56 | 286 | 303 | |
| 78 | A | 57 | 287 | 304 | |
| 79 | K | 58 | 288 | 305 | |
| 80 | T | 59 | 289 | 306 | D-STRAND |
| 81 | K | 60 | 290 | 307 | |
| 82 | P | 61 | 291 | 308 | |
| 83 | R | 62 | 292 | 309 | |
| 84 | E | 63 | 293 | 310 | |
| 84,1 | E | 64 | 294 | 311 | |
| 84,2 | Q | 65 | 295 | 312 | |
| 84,3 | Y | 66 | 296 | 313 | |
| 84,4 | N | 67 | 297 | 314 | |
| 84,5 | - | - | - | - | |
| 84,6 | - | - | - | - | |
| 84,7 | - | - | - | - | DE-TURN |
| 85,7 | - | - | - | - | |
| 85,6 | - | - | - | - | |
| 85,5 | - | - | - | - | |
| 85,4 | S | 68 | 298 | 317 | |
| 85,3 | T | 69 | 299 | 318 | |
| 85,2 | Y | 70 | 300 | 319 | |
| 85,1 | R | 71 | 301 | 320 | |
| 85 | V | 72 | 302 | 321 | |
| 86 | V | 73 | 303 | 322 | |
| 87 | S | 74 | 304 | 323 | |
| 88 | V | 75 | 305 | 324 | |
| 89 | L | 76 | 306 | 325 | |
| 90 | T | 77 | 307 | 326 | E-STRAND |
| 91 | V | 78 | 308 | 327 | |
| 92 | L | 79 | 309 | 328 | |
| 93 | H | 80 | 310 | 329 | |
| 94 | Q | 81 | 311 | 330 | |
| 95 | D | 82 | 312 | 331 | |
| 96 | W | 83 | 313 | 332 | |
| 96,1 | - | - | - | - | EF-TURN |
| 96,2 | - | - | - | - | |
| 97 | L | 84 | 314 | 333 | |
| 98 | N | 85 | 315 | 334 | |
| 99 | G | 86 | 316 | 335 | |
| 100 | K | 87 | 317 | 336 | F-STRAND |
| 101 | E | 88 | 318 | 337 | |
| 102 | Y | 89 | 319 | 338 | |
| 103 | K | 90 | 320 | 339 | |
| 104 | C | 91 | 321 | 340 | |
| 105 | K | 92 | 322 | 341 | |
| 106 | V | 93 | 323 | 342 | |
| 107 | S | 94 | 324 | 343 | |
| 108 | N | 95 | 325 | 344 | |
| 109 | K | 96 | 326 | 345 | |
| 110 | A | 97 | 327 | 346 | |
| 111 | - | - | - | - | FG-LOOP |
| 112 | - | - | - | - | |
| 113 | L | 98 | 328 | 347 | |
| 114 | P | 99 | 329 | 348 | |
| 115 | A | 100 | 330 | 349 | |
| 116 | P | 101 | 331 | 350 | |
| 117 | I | 102 | 332 | 351 | |
| 118 | E | 103 | 333 | 352 | |
| 119 | K | 104 | 334 | 353 | |
| 120 | T | 105 | 335 | 354 | |
| 121 | I | 106 | 336 | 355 | G-STRAND |
| 122 | S | 107 | 337 | 357 | |
| 123 | K | 108 | 338 | 358 | |
| 124 | A | 109 | 339 | 359 | |
| 125 | K | 110 | 340 | 360 | |

Fig. 14

| Structure | Name | Description |
|---|---|---|
| 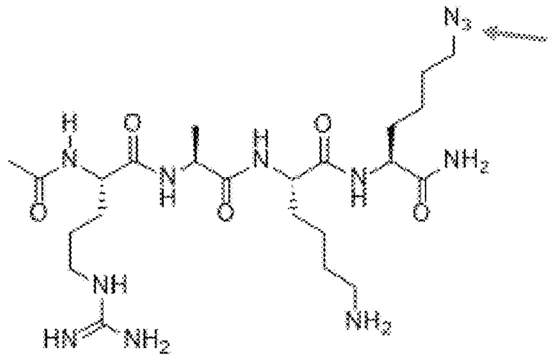 | ArgAlaLysLys(N3) | Lys(N3) comprises an Azide for click chemistry instead of a primary amine. The other Lys provides the primary amine for the transglutaminase reaction |
| 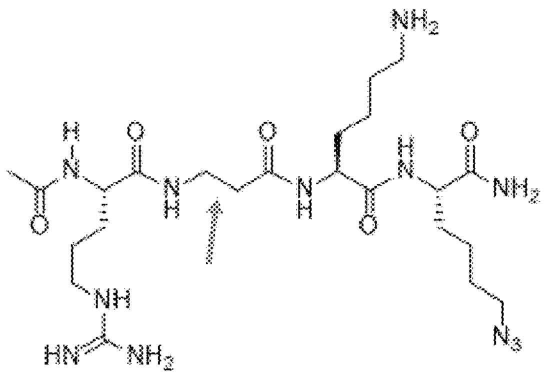 | ArgßAlaLysLys(N3) | ßAla does not make a peptide bond, hence this is an example for a peptidomimetic |
| 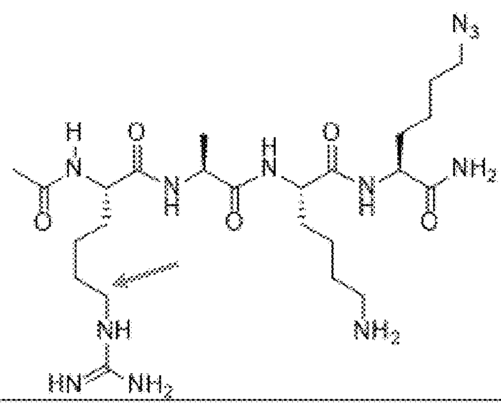 | homoArgAlaLysLys(N3) | homoArg is a non naturally occurring amino acid |
| 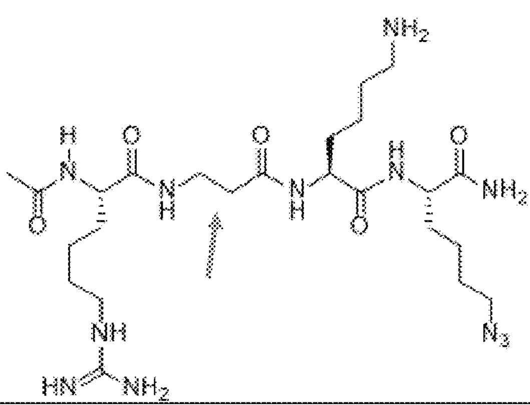 | homoArgßAlaLysLys(N3) | Combination of the upper two |

Fig. 18A

| Structure | Name | Notes |
|---|---|---|
| 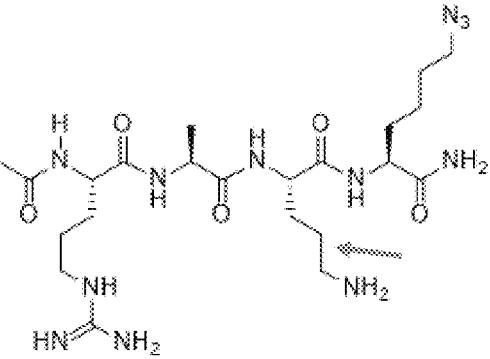 | ArgAlaOrnLys(N3) (SEQ ID NO:15) | Orn is ornithine, i.e., a Lys derivative |
| 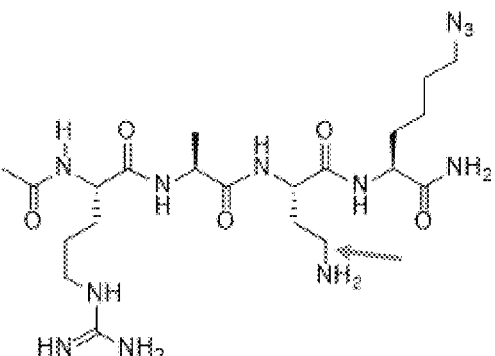 | ArgAlaDabLys(N3) (SEQ ID NO:16) | Dab is α,γ-diaminobutyric acid, i.e., a Lys derivative |
| 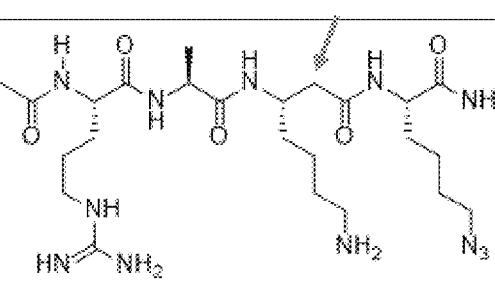 | ArgAlaβhomoLysLys(N3) (SEQ ID NO:17) | βhomoLys = L-βhomolysine (S)-3,7-Diamino-heptanoic acid" is a non naturally occurring amino acid |
| 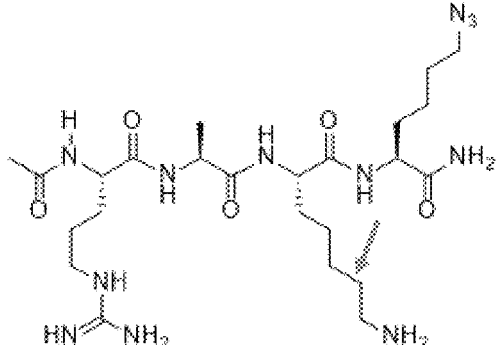 | ArgAlahomoLysLys(N3) (SEQ ID NO:18) | homoLys is a Lys derivative |
Fig. 18B

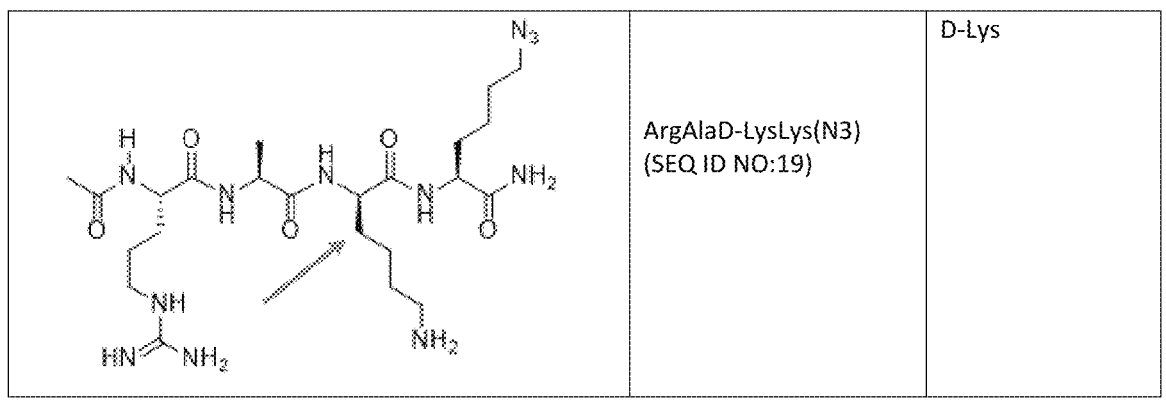
Fig. 18B ctd'

| | | |
|---|---|---|
| 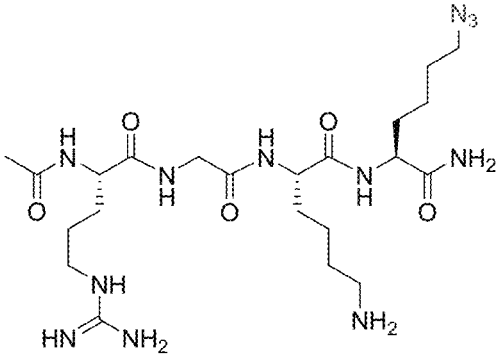 | ArgGlyLysLys(N₃)<br>(SEQ ID NO:6) | |
| 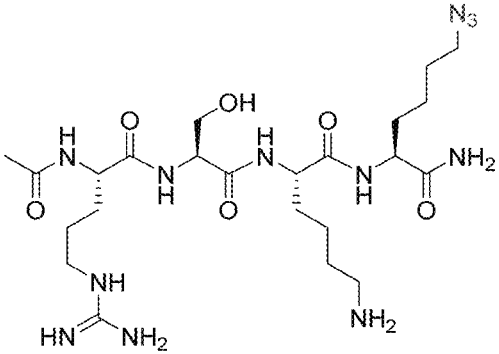 | ArgSerLysLys(N₃)<br>(SEQ ID NO:7) | |
| 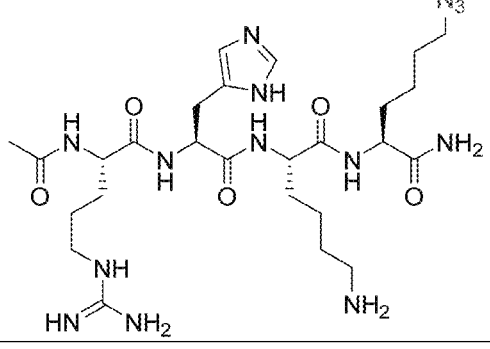 | ArgHisLysLys(N₃)<br>(SEQ ID NO:8) | |
| 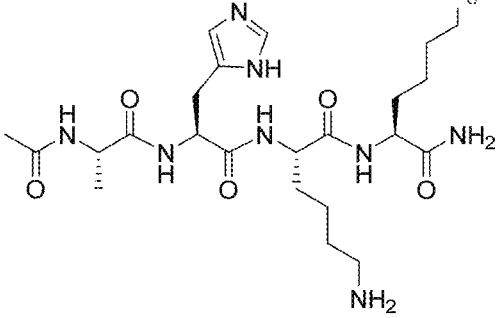 | AlaHisLysLys(N₃)<br>(SEQ ID NO:9) | |
Fig. 19A

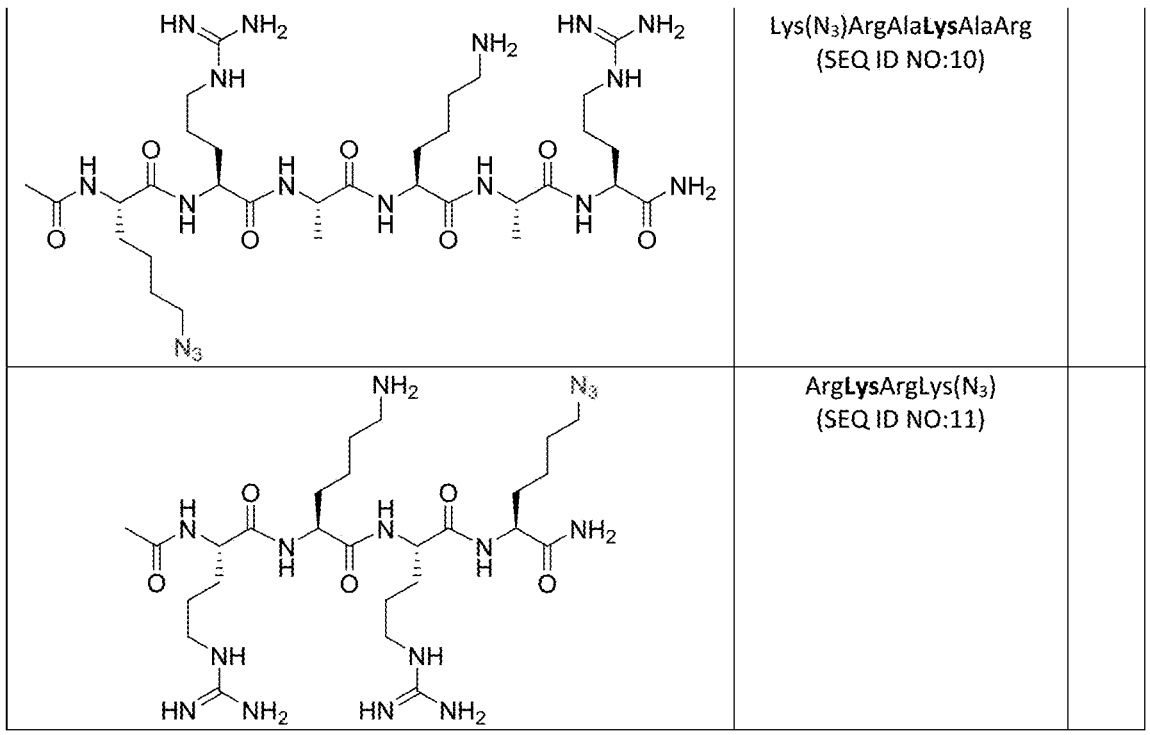
Fig. 19A ctd'
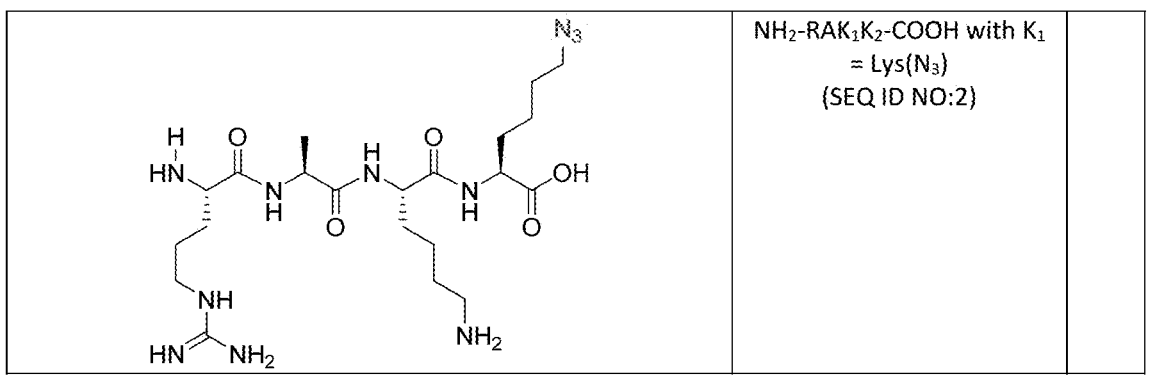
Fig. 19B

| | | |
|---|---|---|
| 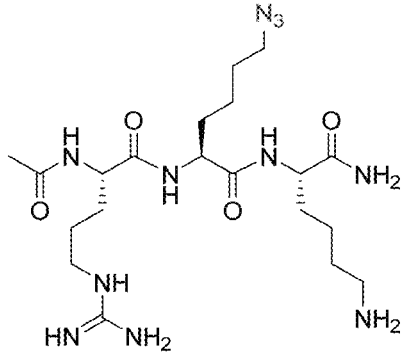 | ArgLys(N₃)Lys<br>(SEQ ID NO:38) | |
| 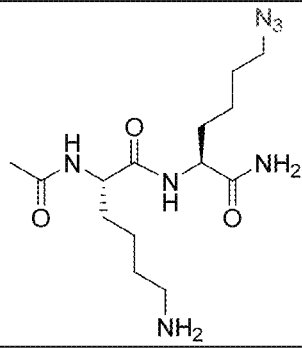 | LysLys(N₃)<br>(SEQ ID NO:39) | |
| 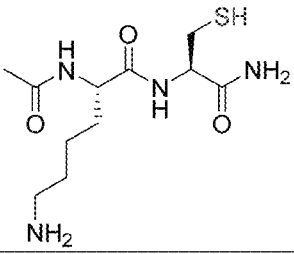 | LysCys<br>(SEQ ID NO:40) | |
Fig. 20

A
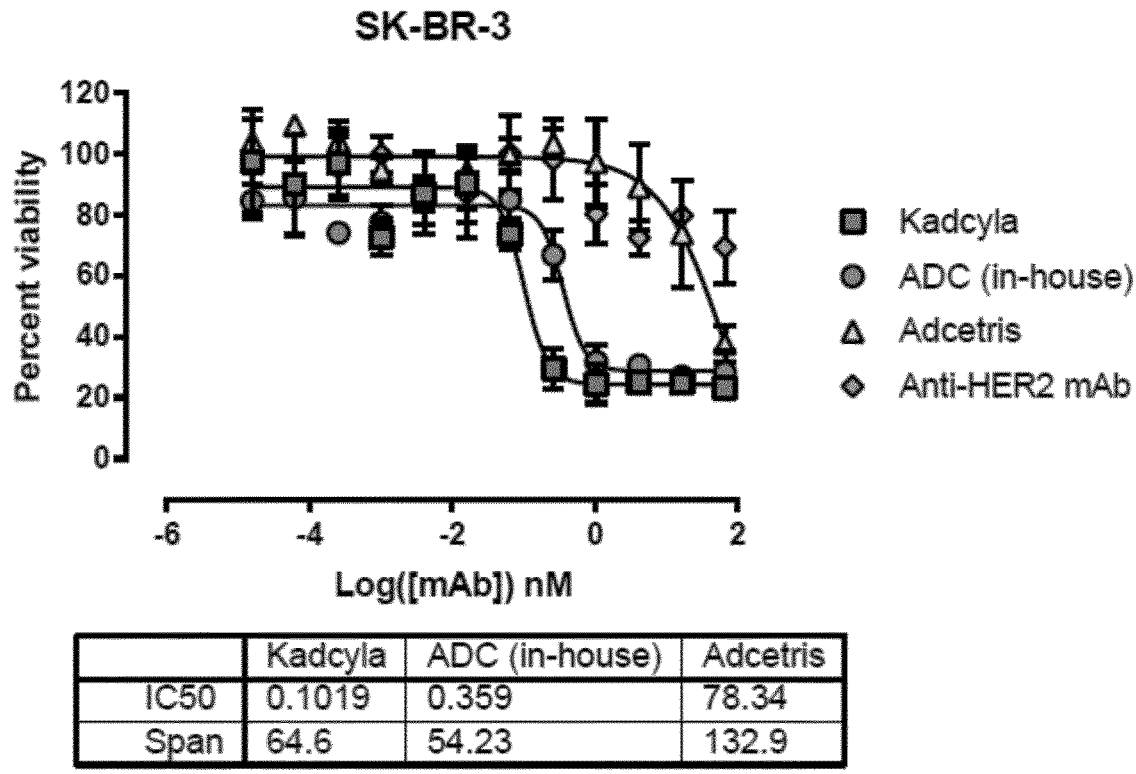
B
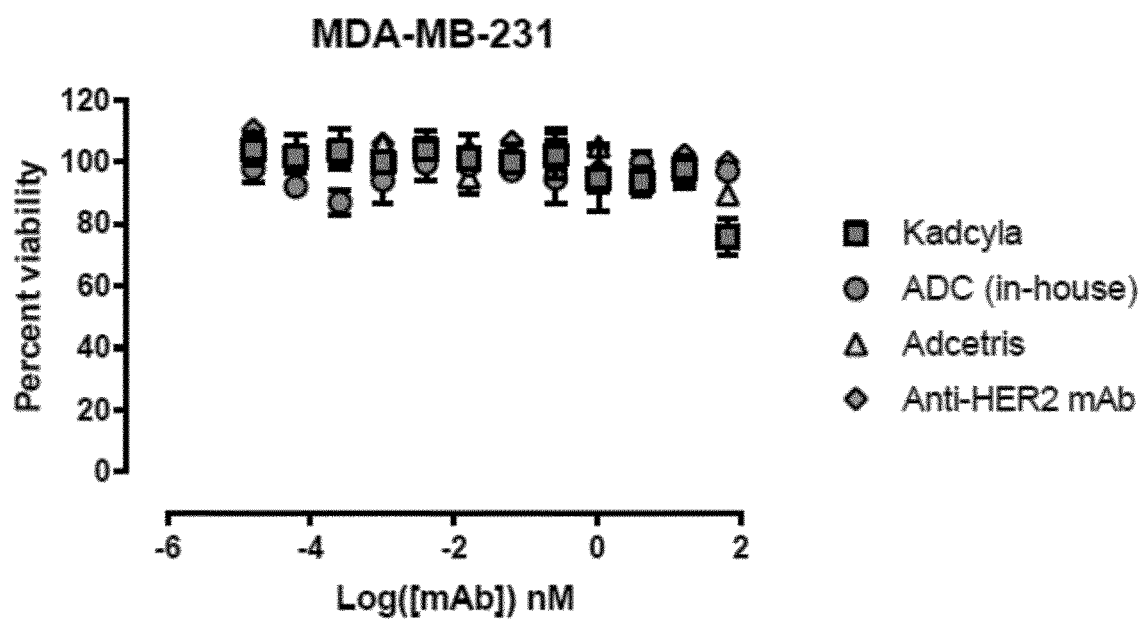
Fig. 22

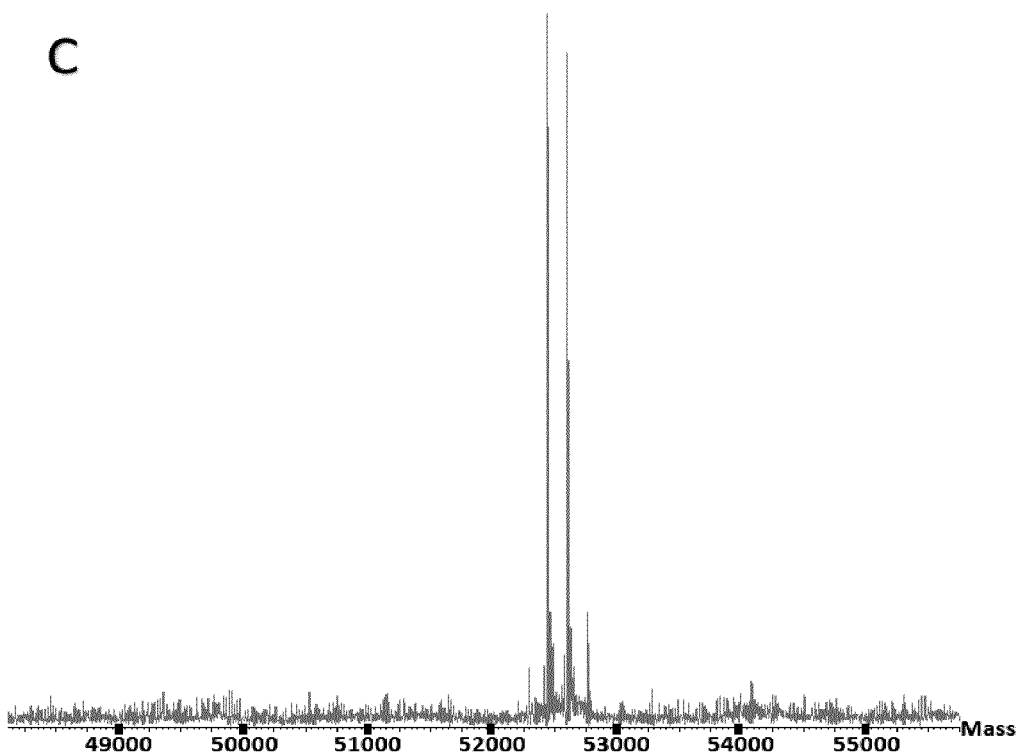
Fig. 27 ctd'

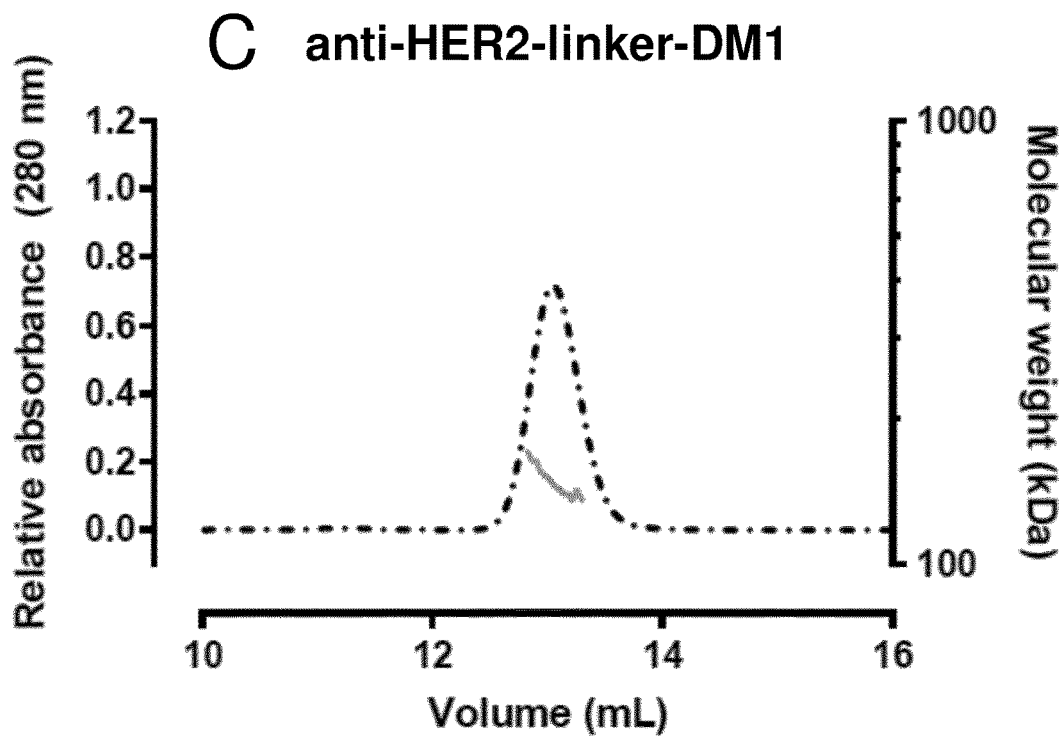
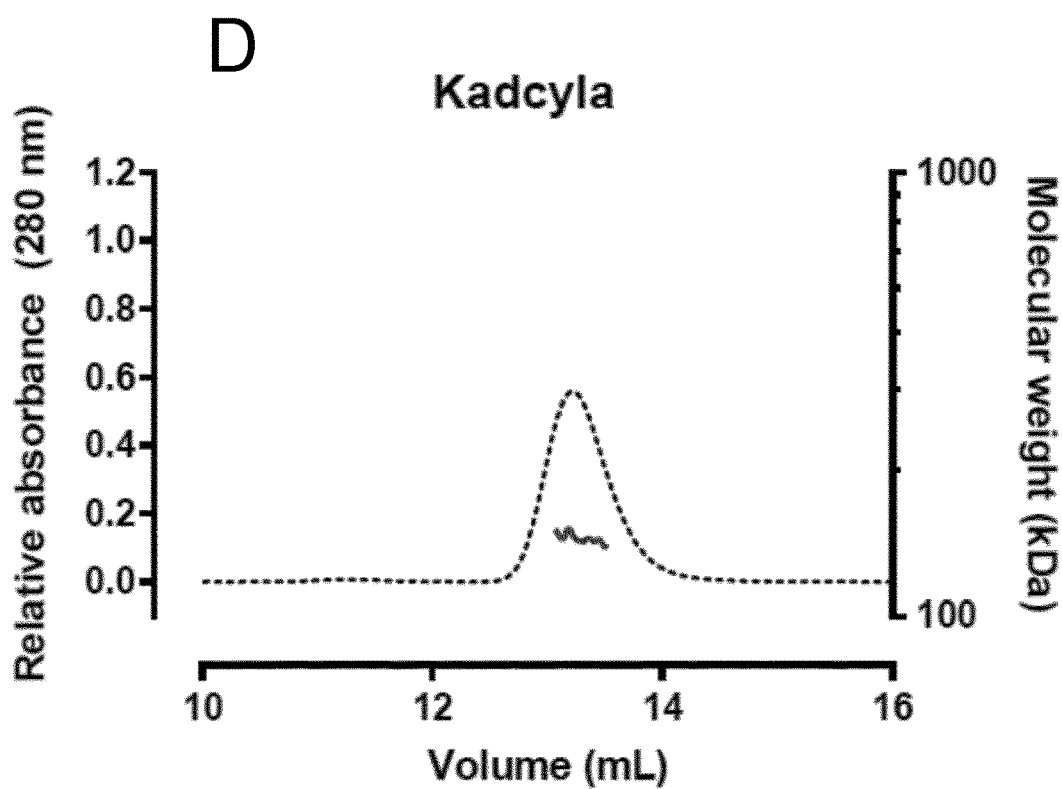
Fig. 28 ctd'

SEQUENCE LISTING

<160> NUMBER OF SEQ ID NOS: 37

<210> SEQ ID NO 1
<211> LENGTH: 6
<212> TYPE: PRT
<213> ORGANISM: Artificial Sequence
<220> FEATURE:
<221> NAME/KEY: MOD_RES
<222> LOCATION: (6)..(6)
<223> OTHER INFORMATION: Xaa is 6-azido-L-lysine (Lys(N3))
<220> FEATURE:
<223> OTHER INFORMATION: synthetic linker

<400> SEQUENCE: 1

Arg Ala Lys Ala Arg Xaa
1               5

```
<210> SEQ ID NO 2
<211> LENGTH: 4
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 2

Arg Ala Lys Xaa
1

<210> SEQ ID NO 3
<211> LENGTH: 4
<212> TYPE: PRT
<213> ORGANISM: Artificial Sequence
<220> FEATURE:
<223> OTHER INFORMATION: synthetic linker
<220> FEATURE:
<221> NAME/KEY: MOD_RES
<222> LOCATION: (4)..(4)
<223> OTHER INFORMATION: Xaa is 4-azido-L-homoalanine

<400> SEQUENCE: 3

Arg Ala Lys Xaa
1

<210> SEQ ID NO 4
<211> LENGTH: 3
<212> TYPE: PRT
<213> ORGANISM: Artificial Sequence
<220> FEATURE:
<223> OTHER INFORMATION: synthetic linker
<220> FEATURE:
<221> NAME/KEY: MOD_RES
<222> LOCATION: (3)..(3)
<223> OTHER INFORMATION: Carboxyl group of Lys is modified with [PEG]3N3

<400> SEQUENCE: 4

Arg Ala Lys
1

<210> SEQ ID NO 5
<211> LENGTH: 4
<212> TYPE: PRT
<213> ORGANISM: Artificial Sequence
<220> FEATURE:
<223> OTHER INFORMATION: synthetic linker

<400> SEQUENCE: 5

Arg Ala Lys Cys
1

<210> SEQ ID NO 6
<211> LENGTH: 4
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 6
```

```
Arg Gly Lys Xaa
1

<210> SEQ ID NO 7
<211> LENGTH: 4
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 7

Arg Ser Lys Xaa
1

<210> SEQ ID NO 8
<211> LENGTH: 4
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 8

Arg His Lys Xaa
1

<210> SEQ ID NO 9
<211> LENGTH: 4
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 9

Ala His Lys Xaa
1

<210> SEQ ID NO 10
<211> LENGTH: 6
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: Xaa is 6-azido-L-lysine (Lys(N3))
<220> FEATURE:
<223> OTHER INFORMATION: synthetic linker

<400> SEQUENCE: 10

Xaa Arg Ala Lys Ala Arg
1               5

<210> SEQ ID NO 11
<211> LENGTH: 4
<212> TYPE: PRT
<213> ORGANISM: Artificial Sequence
<220> FEATURE:
<221> NAME/KEY: MOD_RES
<222> LOCATION: (4)..(4)
```

```
<223> OTHER INFORMATION: Xaa is 6-azido-L-lysine (Lys(N3))
<220> FEATURE:
<223> OTHER INFORMATION: synthetic linker

<400> SEQUENCE: 11

Arg Lys Arg Xaa
1

<210> SEQ ID NO 12
<211> LENGTH: 4
<212> TYPE: PRT
<213> ORGANISM: Artificial Sequence
<220> FEATURE:
<221> NAME/KEY: MOD_RES
<222> LOCATION: (2)..(2)
<223> OTHER INFORMATION: Xaa is beta Alanine
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 12

Arg Xaa Lys Xaa
1

<210> SEQ ID NO 13
<211> LENGTH: 4
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: Xaa is L-homoarginine
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 13

Xaa Ala Lys Xaa
1

<210> SEQ ID NO 14
<211> LENGTH: 4
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: Xaa = L-homoarginine
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 14

Xaa Xaa Lys Xaa
1

<210> SEQ ID NO 15
<211> LENGTH: 4
```

```
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Xaa is Ornithine
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 15

Arg Ala Xaa Xaa
1

<210> SEQ ID NO 16
<211> LENGTH: 4
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Xaa is alpha,gamma,-diaminobutyric acid
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 16

Arg Ala Xaa Xaa
1

<210> SEQ ID NO 17
<211> LENGTH: 4
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Xaa = L-beta-homolysine ((S)-3,7-Diamino-
      heptanoic acid)
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 17

Arg Ala Xaa Xaa
1

<210> SEQ ID NO 18
<211> LENGTH: 4
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Xaa is L-homolysine
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 18
```

Arg Ala Xaa Xaa
1

<210> SEQ ID NO 19
<211> LENGTH: 4
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: Xaa is D-Lysine
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<223> OTHER INFORMATION: synthetic linker

<400> SEQUENCE: 19

Arg Ala Xaa Xaa
1

<210> SEQ ID NO 20
<211> LENGTH: 7
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<221> NAME/KEY: MOD_RES
<222> LOCATION: (7)..(7)
<223> OTHER INFORMATION: Xaa is L-Lys(tetrazine)
<220> FEATURE:
<223> OTHER INFORMATION: synthetic linker

<400> SEQUENCE: 20

Arg Ala Lys Xaa Arg Ala Xaa
1               5

<210> SEQ ID NO 21
<211> LENGTH: 5
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: Xaa is 6-azido-L-lysine (Lys(N3))
<220> FEATURE:
<223> OTHER INFORMATION: synthetic linker

<400> SEQUENCE: 21

Xaa Cys Arg Ala Lys
1               5

<210> SEQ ID NO 22
<211> LENGTH: 5
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: Xaa is 6-azido-L-lysine (Lys(N3))
<220> FEATURE:
<223> OTHER INFORMATION: synthetic linker

<400> SEQUENCE: 22

Xaa Ala Arg Cys Lys
1               5

```
<210> SEQ ID NO 23
<211> LENGTH: 7
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: Xaa is 6-azido-L-lysine (Lys(N3))
<220> FEATURE:
<221> NAME/KEY: MOD_RES
<222> LOCATION: (7)..(7)
<223> OTHER INFORMATION: Xaa is 6-azido-L-lysine (Lys(N3))
<220> FEATURE:
<223> OTHER INFORMATION: synthetic linker

<400> SEQUENCE: 23

Xaa Arg Ala Lys Ala Arg Xaa
1               5

<210> SEQ ID NO 24
<211> LENGTH: 5
<212> TYPE: PRT
<213> ORGANISM: Artificial Sequence
<220> FEATURE:
<221> NAME/KEY: MOD_RES
<222> LOCATION: (4)..(4)
<223> OTHER INFORMATION: Xaa is 6-azido-L-lysine (Lys(N3))
<220> FEATURE:
<221> NAME/KEY: MOD_RES
<222> LOCATION: (5)..(5)
<223> OTHER INFORMATION: Xaa is 6-azido-L-lysine (Lys(N3))
<220> FEATURE:
<223> OTHER INFORMATION: synthetic linker

<400> SEQUENCE: 24

Lys Ala Arg Xaa Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic linker

<400> SEQUENCE: 25

Arg Ala Ala Arg Lys
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic linker

<400> SEQUENCE: 26

Arg Arg Lys Ala Tyr
1               5

<210> SEQ ID NO 27
<211> LENGTH: 5
<212> TYPE: PRT
<213> ORGANISM: Artificial Sequence
<220> FEATURE:
<223> OTHER INFORMATION: synthetic linker

<400> SEQUENCE: 27

Arg Arg Lys Asn Tyr
```

1               5

<210> SEQ ID NO 28
<211> LENGTH: 5
<212> TYPE: PRT
<213> ORGANISM: Artificial Sequence
<220> FEATURE:
<223> OTHER INFORMATION: synthetic linker

<400> SEQUENCE: 28

Lys Ala Arg Ala Arg
1               5

<210> SEQ ID NO 29
<211> LENGTH: 4
<212> TYPE: PRT
<213> ORGANISM: Artificial Sequence
<220> FEATURE:
<223> OTHER INFORMATION: synthetic linker

<400> SEQUENCE: 29

Lys Ala Arg Ala
1

<210> SEQ ID NO 30
<211> LENGTH: 5
<212> TYPE: PRT
<213> ORGANISM: Artificial Sequence
<220> FEATURE:
<223> OTHER INFORMATION: synthetic linker

<400> SEQUENCE: 30

Arg Ala Lys Ala Arg
1               5

<210> SEQ ID NO 31
<211> LENGTH: 4
<212> TYPE: PRT
<213> ORGANISM: Artificial Sequence
<220> FEATURE:
<223> OTHER INFORMATION: synthetic linker

<400> SEQUENCE: 31

Ala Tyr Ala Lys
1

<210> SEQ ID NO 32
<211> LENGTH: 7
<212> TYPE: PRT
<213> ORGANISM: Artificial Sequence
<220> FEATURE:
<223> OTHER INFORMATION: synthetic linker

<400> SEQUENCE: 32

Arg Ala Lys Ala Arg Gly Lys
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic linker

<400> SEQUENCE: 33

Arg Ala Lys Lys Asn Arg Ala Lys
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic linker

<400> SEQUENCE: 34

Asn Lys Ala Leu Lys Ala Pro
1               5

<210> SEQ ID NO 35
<211> LENGTH: 12
<212> TYPE: PRT
<213> ORGANISM: Artificial Sequence
<220> FEATURE:
<223> OTHER INFORMATION: synthetic linker

<400> SEQUENCE: 35

Asp Gly Val Glu Lys Asn Ala Lys Thr Lys Pro Arg
1               5                   10

<210> SEQ ID NO 36
<211> LENGTH: 395
<212> TYPE: PRT
<213> ORGANISM: Streptoverticillium ladakanum

<400> SEQUENCE: 36

Met His Arg Arg Ile His Ala Val Gly Gln Ala Arg Pro Pro Thr
1               5                   10                  15

Met Ala Arg Gly Lys Glu Thr Lys Ser Tyr Ala Glu Thr Tyr Arg Leu
                20                  25                  30

Thr Ala Asp Asp Val Ala Asn Ile Asn Ala Leu Asn Glu Ser Ala Pro
            35                  40                  45

Ala Ala Ser Ser Ala Gly Pro Ser Phe Arg Ala Pro Asp Ser Asp Asp
        50                  55                  60

Arg Val Thr Pro Pro Ala Glu Pro Leu Asp Arg Met Pro Asp Pro Tyr
65                  70                  75                  80

Arg Pro Ser Tyr Gly Arg Ala Glu Thr Val Val Asn Asn Tyr Ile Arg
                85                  90                  95

Lys Trp Gln Gln Val Tyr Ser His Arg Asp Gly Arg Lys Gln Gln Met
            100                 105                 110

Thr Glu Glu Gln Arg Glu Trp Leu Ser Tyr Gly Cys Val Gly Val Thr
        115                 120                 125

Trp Val Asn Ser Gly Gln Tyr Pro Thr Asn Arg Leu Ala Phe Ala Ser
    130                 135                 140

Phe Asp Glu Asp Arg Phe Lys Asn Glu Leu Lys Asn Gly Arg Pro Arg
145                 150                 155                 160

Ser Gly Glu Thr Arg Ala Glu Phe Glu Gly Arg Val Ala Lys Glu Ser
                165                 170                 175

Phe Asp Glu Glu Lys Gly Phe Gln Arg Ala Arg Glu Val Ala Ser Val
            180                 185                 190

Met Asn Arg Ala Leu Glu Asn Ala His Asp Glu Ser Ala Tyr Leu Asp
        195                 200                 205

Asn Leu Lys Lys Glu Leu Ala Asn Gly Asn Asp Ala Leu Arg Asn Glu
    210                 215                 220

Asp Ala Arg Ser Pro Phe Tyr Ser Ala Leu Arg Asn Thr Pro Ser Phe
225                 230                 235                 240

```
Lys Glu Arg Asn Gly Gly Asn His Asp Pro Ser Arg Met Lys Ala Val
                245                 250                 255

Ile Tyr Ser Lys His Phe Trp Ser Gly Gln Asp Arg Ser Ser Ala
            260                 265                 270

Asp Lys Arg Lys Tyr Gly Asp Pro Asp Ala Phe Arg Ser Ala Pro Gly
            275                 280                 285

Thr Gly Leu Val Asp Met Ser Arg Asp Arg Asn Ile Pro Arg Ser Pro
290                 295                 300

Thr Ser Pro Gly Glu Gly Phe Val Asn Phe Asp Tyr Gly Trp Phe Gly
305                 310                 315                 320

Ala Gln Thr Glu Ala Asp Ala Asp Lys Thr Val Trp Thr His Gly Asn
                325                 330                 335

His Tyr His Ala Pro Asn Gly Ser Leu Gly Cys His Ala Cys Leu Thr
                340                 345                 350

Arg Ala Ser Ser Ala Thr Gly Ser Glu Gly Tyr Ser Asp Phe Asp Arg
            355                 360                 365

Gly Glu Pro Tyr Val Val Ser Pro Ser Pro Ser Pro Arg Met Leu Glu
            370                 375                 380

His Arg Pro Arg Gln Gly Lys Ala Gly Leu Ala
385                 390                 395

<210> SEQ ID NO 37
<211> LENGTH: 335
<212> TYPE: PRT
<213> ORGANISM: Streptoverticillium ladakanum

<400> SEQUENCE: 37

Phe Arg Ala Pro Asp Ser Asp Glu Arg Val Thr Pro Pro Ala Glu Pro
1               5                   10                  15

Leu Asp Arg Met Pro Asp Pro Tyr Arg Pro Ser Tyr Gly Arg Ala Glu
                20                  25                  30

Thr Ile Val Asn Asn Tyr Ile Arg Lys Trp Gln Gln Val Tyr Ser His
            35                  40                  45

Arg Asp Gly Arg Lys Gln Gln Met Thr Glu Glu Gln Arg Glu Trp Leu
        50                  55                  60

Ser Tyr Gly Cys Val Gly Val Thr Trp Val Asn Ser Gly Gln Tyr Pro
65              70                  75                  80

Thr Asn Arg Leu Ala Phe Ala Phe Phe Asp Glu Asp Lys Tyr Lys Asn
                85                  90                  95

Glu Leu Lys Asn Gly Arg Pro Ser Gly Glu Thr Arg Ala Glu Phe
            100                 105                 110

Glu Gly Arg Val Ala Lys Asp Ser Phe Asp Glu Ala Lys Gly Phe Gln
        115                 120                 125

Arg Ala Arg Asp Val Ala Ser Val Met Asn Lys Ala Leu Glu Asn Ala
130                 135                 140

His Asp Glu Gly Ala Tyr Leu Asp Asn Leu Lys Lys Glu Leu Ala Asn
145                 150                 155                 160

Gly Asn Asp Ala Leu Arg Asn Glu Asp Ala Arg Ser Pro Phe Tyr Ser
                165                 170                 175

Ala Leu Arg Asn Thr Pro Ser Phe Lys Asp Arg Asn Gly Asn His
            180                 185                 190

Asp Pro Ser Lys Met Lys Ala Val Ile Tyr Ser Lys His Phe Trp Ser
            195                 200                 205

Gly Gln Asp Arg Ser Gly Ser Ser Asp Lys Arg Lys Tyr Gly Asp Pro
```

```
                210                215                220
Glu Ala Phe Arg Pro Asp Arg Gly Thr Gly Leu Val Asp Met Ser Arg
225                 230                 235                 240

Asp Arg Asn Ile Pro Arg Ser Pro Thr Ser Pro Gly Glu Ser Phe Val
                245                 250                 255

Asn Phe Asp Tyr Gly Trp Phe Gly Ala Gln Thr Glu Ala Asp Ala Asp
                260                 265                 270

Lys Thr Val Trp Thr His Gly Asn His Tyr His Ala Pro Asn Gly Ser
                275                 280                 285

Leu Gly Ala Met His Val Tyr Glu Ser Lys Phe Arg Asn Trp Ser Asp
                290                 295                 300

Gly Tyr Ser Asp Phe Asp Arg Gly Ala Tyr Val Val Thr Phe Val Pro
305                 310                 315                 320

Lys Ser Trp Asn Thr Ala Pro Asp Lys Val Thr Gln Gly Trp Pro
                325                 330                 335
```

TRANSGLUTAMINASE CONJUGATION METHOD AND LINKER

CROSS REFERENCE TO RELATED APPLICATIONS

The present application is a 35 U.S.C. § 371 national phase entry of International Patent Application No. PCT/EP2018/075350, filed on Sep. 19, 2018, which claims the benefit of priority to GB Patent Application No. 1800878.9, filed on Jan. 19, 2018, and EP Patent Application No. 17191825.3, filed on Sep. 19, 2017, the entire contents of each of which are incorporated by reference herein for all purposes.

SEQUENCE LISTING

The instant application contains a Sequence Listing which has been submitted electronically in ASCII format and is hereby incorporated by reference in its entirety. Said ASCII copy, created on Jun. 30, 2020, is named 1182684_AD1454US_SL2.txt and is 15,143 bytes in size.

FIELD OF THE INVENTION

The present invention relates to method for generating an antibody-payload conjugate by means of a microbial transglutaminase.

BACKGROUND

Attaching highly potent payloads to antibodies finds increased interest for the targeted treatment of cancer or inflammatory diseases. The constructs this produces are called antibody-payload conjugates, or antibody-drug conjugates (ADC).

Currently, four ADCs have gained FDA-approval (Adcetris, Kadcyla, Besponsa and Mylotarg) all of which have their payload chemically attached to the antibody in a non-site specific manner. Hence, the resulting product is highly heterogeneous, both with respect to the stoichiometric relationship between antibody and payload (payload antibody ratio, or drug to antibody ratio, DAR), as well concerning the conjugation sites on the antibody. Each of the resulting species, although in the same drug product, may have distinct properties that could potentially lead to a wide range of different in-vivo pharmacokinetic properties and activities.

In a previous in-vivo study (Lhospice et al., 2015), it was shown that a site-specific drug attachment led to a significant higher tumor uptake (~2×) and a decreased uptake in non-targeted tissues compared to the FDA-approved ADC, also the maximal tolerated dose was at least 3× higher. These data suggest that stoichiometrically well-defined ADCs display improved pharmacokinetics and better therapeutic indexes compared to chemically modified ADCs.

As a site-specific technology, enzymatic conjugation has shown great interest since these conjugation reactions are typically fast and can be done under physiological conditions. Among the available enzymes, microbial transglutaminase (MTG) from the species *Streptomyces mobaraensis* has found increasing interest as an attractive alternative to conventional chemical protein conjugation of functional moieties including antibodies. The MTG catalyzes under physiological conditions a transamidation reaction between a 'reactive' glutamine of a protein or peptide and a 'reactive' lysine residue of a protein or peptide, whereas the latter can also be a simple, low molecular weight primary amine such as a 5-aminopentyl group (Jeger et al., 2010, Strop et al., 2014).

The bond formed is an isopeptide bond which is an amide bond, that does not form part of the peptide-bond backbone of the respective polypeptide or protein. It is formed between the Gamma-carboxamide of the glutamyl residue of the acyl glutamine-containing amino acid donor sequence and a primary (1°) amine of the amino donor-comprising substrate according to the invention.

From the inventor's experience as well as from others it seems that only few glutamines are typically targeted by MTG, thus making the MTG an attractive tool for site-specific and stoichiometric protein modifications.

Previously, glutamine 295 (Q295) was identified as the only reactive glutamine on the heavy chain of different IgG types to be specifically targeted by MTG with low-molecular weight primary amine substrates (Jeger et al. 2010).

Quantitative conjugation to Q295, however, was only possible upon removal of the glycan moiety at the asparagine residue 297 (N297) with PNGase F, while glycosylated antibodies could not be conjugated efficiently (conjugation efficiency <20). This finding is also supported by the studies of Mindt et al. (2008) and Jeger et al. (2010).

In order to obviate deglycosylation it is also possible to insert a point mutation at the residue N297 which results in the ablation of the glycosylation called aglycosylation.

However, both approaches come with significant disadvantages. An enzymatic deglycosylation step is undesired under GMP aspects, because it has to be made sure that the both the deglycosylation enzyme (e.g., PNGase F) as well as the cleaved glycan have to be removed from the medium, to ensure a high purity product.

The substitution of N297 against another amino acid has unwanted effects, too, because it may affect the overall stability of the $C_H2$ domain, and the efficacy of the entire conjugate as a consequence. Further, the glycan that is present at N297 has important immunomodulatory effects, as it triggers antibody dependent cellular cytotoxicity (ADCC) and the like. These immunomodulatory effects would get lost upon deglycosylation or substitution of N297 against another amino acid.

Furthermore, the genetic engineering of an antibody for payload attachment may have disadvantages in that the sequence insertion may increase immunogenicity and decrease the overall stability of the antibody.

It is hence one object of the present invention to provide a transglutaminase based antibody conjugation approach which does not require prior deglycosylation of the antibody, in particular of N297.

It is another object of the present invention to provide a transglutaminase based antibody conjugation approach which does not require the substitution or modification of N297 in the $C_H2$ domain.

It is one further object of the present invention to provide an antibody conjugation technology that allows the manufacture of highly homogenous conjugation products, both as regards stoichiometry as well as site-specificity of the conjugation.

These and further objects are met with methods and means according to the independent claims of the present invention. The dependent claims are related to specific embodiments.

SUMMARY OF THE INVENTION

The present invention relates to methods and linker structures for generating an antibody-payload conjugate by means of a microbial transglutaminase (MTG). The invention and general advantages of its features will be discussed in detail below.

As discussed elsewhere herein, B/star can be a linking moiety, like e.g. a bio-orthogonal group (e.g., an azide/$N_3$-group) that is suitable for strain-promoted alkyne-azide cycloaddition (SPAAC) click-chemistry reaction to a DBCO-containing payload (e.g. a toxin or a fluorescent dye or a metal chelator, like DOTA or NODA-GA). This click-chemistry-based "two-step chemoenzymatic"-approach to attach the functional moiety to the antibody has the major advantage that it can be clicked at low molecular excess versus to the antibody, typically e.g. at 5 eq per conjugation site or lower (Dennler et al. 2014). This allows for a cost-effective generation of ADCs. In addition, virtually any probe can be clicked with this approach ranging from fluorescent dyes to metal chelators (cf. Spycher et al. 2017, Dennler et al. 2015).

B/star can also be the actual payload, e.g., a toxin. Such embodiment allows the rapid manufacture of the resulting compound in one step, facilitating purification and production.

Figure 1:
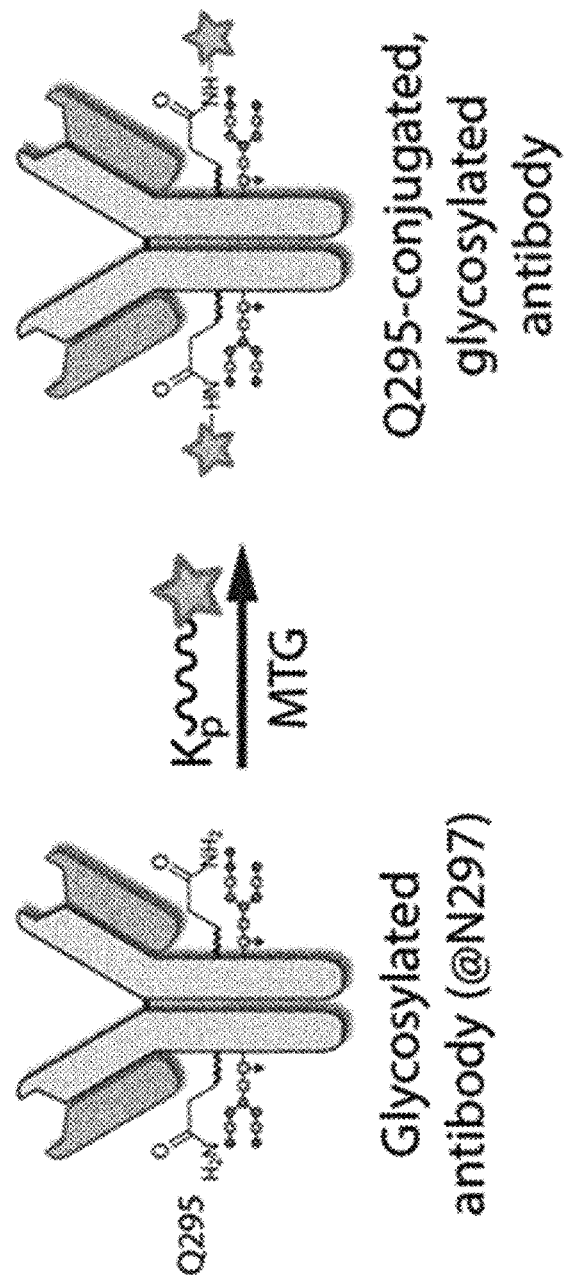
FIG. 1 shows an illustration of one aspect of the present invention. MTG=microbial transglutaminase. The star symbol illustrates the payload or linking moiety B. Kp is a Lysine residue, lysine derivative or lysine mimetic, which can be N- or C-terminal or intrachain of a peptide, and which is the substrate for MTG. Note that this process allows to maintain the glycosylation at N297. Note that in case B/star is a linking moiety, the actual payload still has to be conjugated to this moiety.
Figure 2:
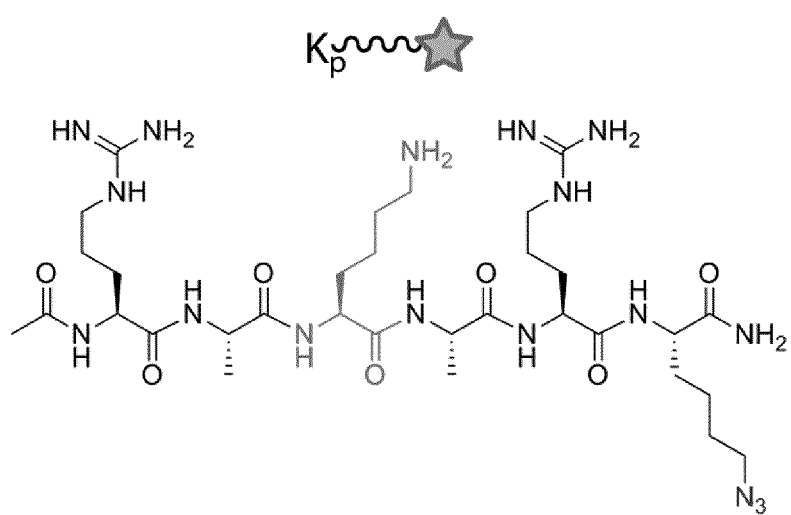

FIG. 2 shows an example of a linker peptide comprising an oligopeptide according to the invention. The sequence is ArgAlaLysAlaArgLys($N_3$) ($RAK_1ARK_2$, with $K_2$=Lys($N_3$)) (SEQ ID NO:1). Lys($N_3$) is a Lys residue in which the primary amine has been replaced by an Azide (—N≡N, or —$N_3$). According to the nomenclature of the present invention, either Lys($N_3$) or $N_3$ alone can be regarded as the linking moiety B (in this example, $N_3$ is suitable for click-chemistry).

The peptide efficiently conjugates to native IgG1 antibody (~77% as estimated from LC-MS analysis under non-optimized conditions) at position Q295.

It is important to understand that in some linker peptides shown herein, the moiety at the C-terminus is simply designated as $N_3$. However, this should be understood as an abbreviation of Lys($N_3$). For example, RAKAR($N_3$) or ArgAlaLysAlaArg($N_3$) does actually mean $RAK_1ARK_2$, with $K_2$=Lys($N_3$), or ArgAlaLysAlaArgLys($N_3$) (SEQ ID NO:1).

It is furthermore important to understand that in different linker peptides shown herein, the C-terminus and/or the N-terminus may or may not be protected, even if shown otherwise. Protection can be accomplished by, e.g., amidation of the former, and/or acetylation of the latter. In the context of the present invention, both the protected and unprotected linker peptides are encompassed.

For example RAKARK($N_3$) does indeed encompass four variants, with a) both termini protected as discussed above, b) only the N-terminus or the C-terminus protected as discussed above, or c) both termini unprotected.

The following figure shows a C-terminal Lys($N_3$) with an amidated C-terminus:

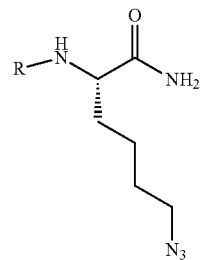

Figure 3:
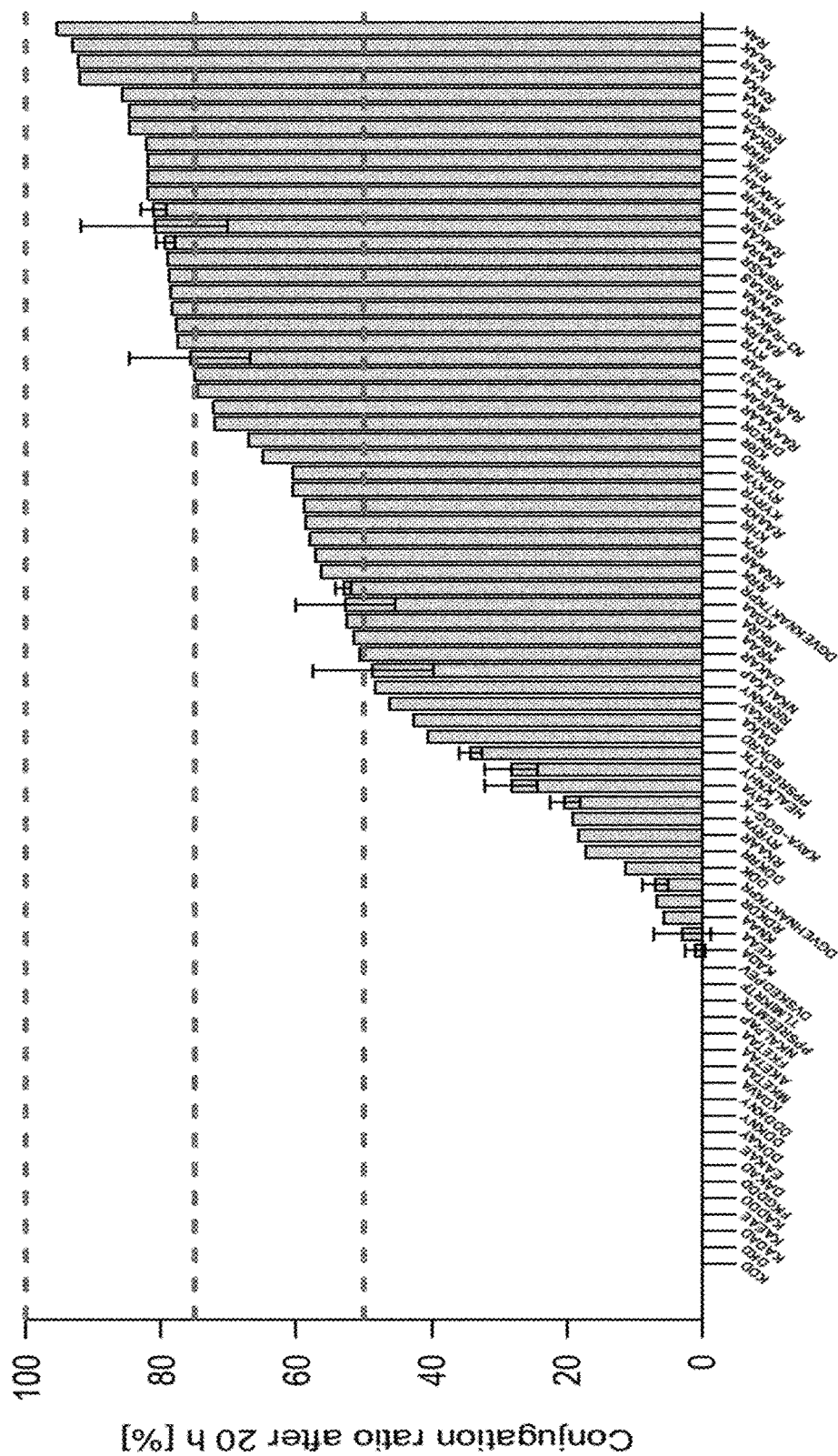

FIG. 3 shows results of the screening of a given peptide library. Different peptides were screened that contained a MTG-reactive lysine residue and which also had different lengths and charges. LC-MS was used for analysis. Clearly, positively charged peptides seem to favor Q295 conjugation while negatively c charged peptides yield poor conjugation yields.

Figure 4:
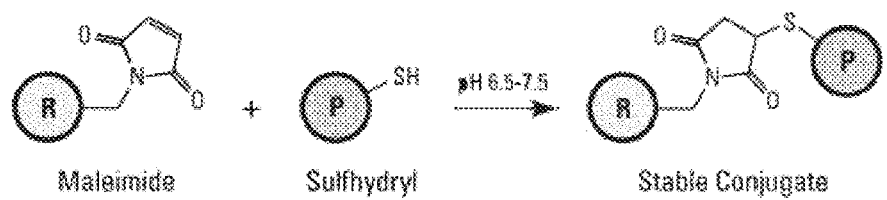

FIGS. 4 and 5 show an embodiment where the linker comprises a Cys residue with a free sulfhydryl group, suitable to conjugate a maleimide-comprising toxin linker construct thereto.

FIG. 4 shows the binding reaction, and FIG. 5 some potential linker constructs.

| Linker peptide | Process type | Steps |
|---|---|---|
| (Aax)m-Lys-(Aax)n-Payload | One-step conjugation | step 1: conjugation of linker comprising the payload to Gln residue in antibody |
| (Aax)m-Lys-(Aax)n-Linking moiety | Two-step conjugation | step 1: conjugation of linker comprising the Linking moiety to Gln residue in antibody<br>step 2: conjugation of payload to Linking moiety |

Figure 6A:
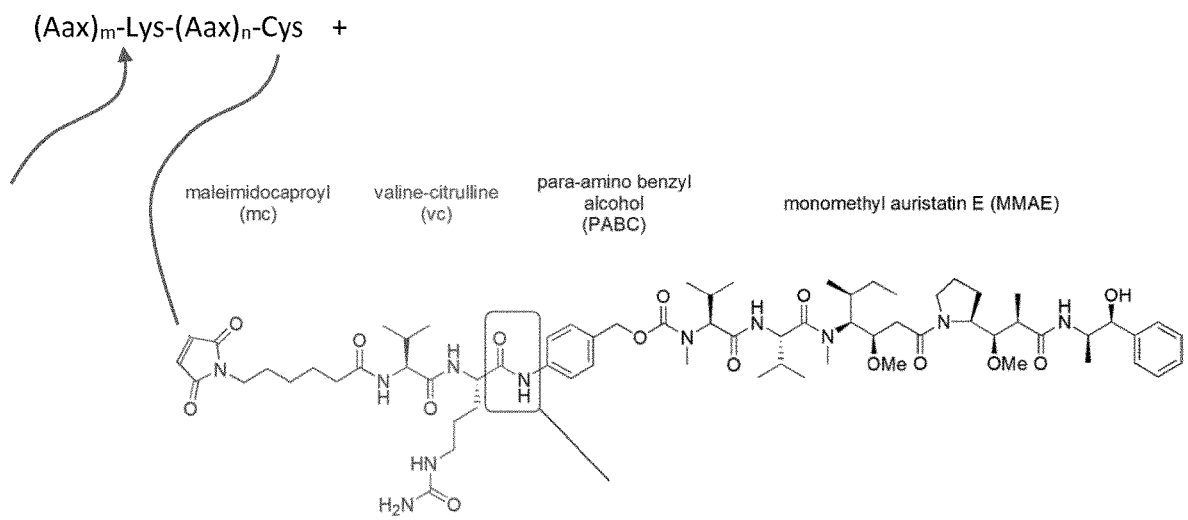
Figure 6B:
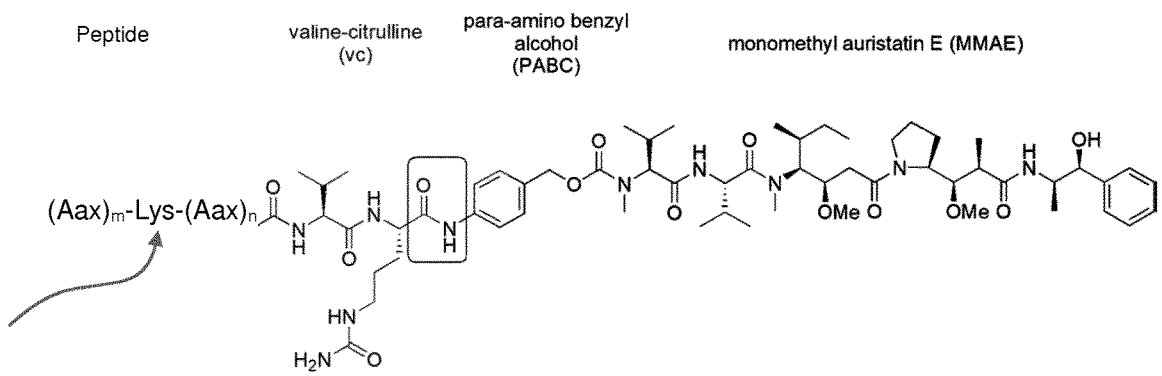

FIGS. 6A and 6B show a two-step conjugation process (FIG. 6A) with the peptide being conjugated to the Gln of the antibody (either Q295 or molecularly engineered) and a one-step conjugation process (FIG. 6B) according to the present invention.

In the two-step process, the linker peptide is (Aax)m-Lys-(Aax)n-linking moiety. The Lys residue is conjugated to a Gln residue in the antibody via microbial transglutaminase, and the linking moiety—in this case a Cys residue with a free sulfhydryl group—is then conjugated to the payload, in this case a MMAE toxin carrying a MC/VC/PABDC linker structure, via the maleimide.

In the one two-step process, the linker peptide (Aax)m-Lys-(Aax)n is already conjugated to the payload. The Lys residue is conjugated to a Gln residue in the antibody, and the payload consist of an MMAE toxin carrying a VC/PABDC structure. The valine residue of the VC structure is conjugated to the last amino acid of the linker peptide by means of a peptide bond FIG. 7A-7C show three examples of linkers comprising a linker suitable for dual-payload attachment.

Figure 7A:
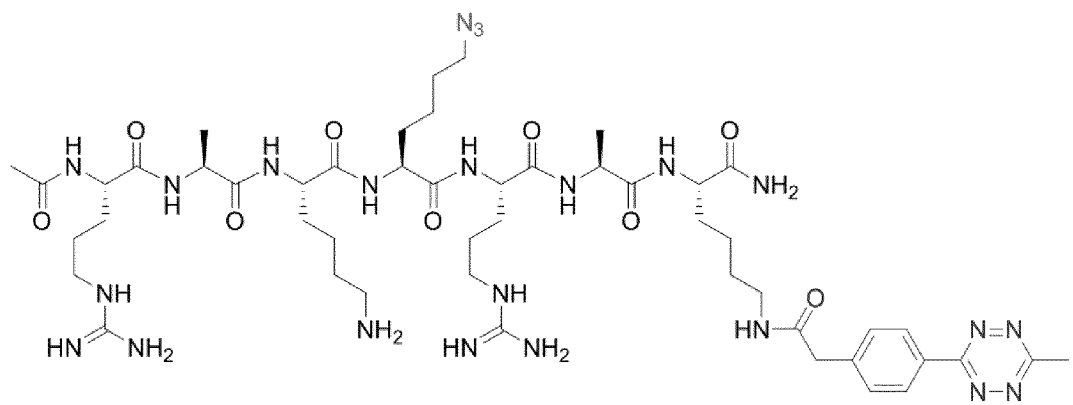

FIG. 7A shows a peptide that has a first linking moiety which is an azide ($N_3$), while a second linking moiety is a tetrazine (both bio-orthogonal). The structure of the oligopeptide is ArgAlaLysLys($N_3$)-ArgAlaLys(Tetrazine) ($RAK_1K_2RAK_3$, with $K_2$=Lys($N_3$), $K_3$=Lys(Tetrazine)) (SEQ ID NO:20).

Figure 7B:
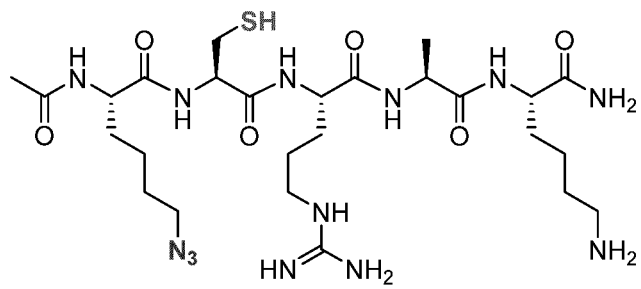

FIG. 7B shows a peptide carrying an azide ($N_3$) and a free sulfhydryl-group from the Cys-moiety. The structure of the oligopeptide is Lys(N$_3$)CysArgAlaLys (K$_1$CRAK$_2$, with K$_1$=Lys(N$_3$)) (SEQ ID NO:21).

Figure 7C:
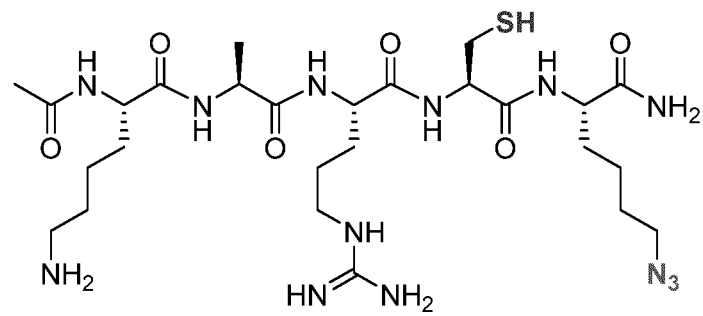

FIG. 7C shows another peptide carrying an azide (N$_3$) and a free sulfhydryl-group from the Cys-moiety. The structure of the oligopeptide is LysAlaArgCysLys(N$_3$) (K$_1$ARCK2, with K$_2$=Lys(N$_3$)) (SEQ ID NO:22).

Each of the linking moieties are bio-orthogonally compatible groups that can be clicked simultaneously.

These linkers thus allow to conjugate two different payloads to the Q295 of the C$_H$2 domain of an antibody. Using a second payload allows for the development of a completely new class of antibody payload conjugates that go beyond current therapeutic approaches with respect to efficacy and potency. Also new application fields are envisioned, for example, dual-type imaging for imaging and therapy or intra-/postoperative surgery (cf. Azhdarinia A. et al., Molec Imaging and Biology, 2012). For example, dual-labeled antibodies encompassing a molecular imaging agent for preoperative positron emission tomography (PET) and a near-infrared fluorescent (NIRF)-dye for guided delineation of surgical margins could greatly enhance the diagnosis, staging, and resection of cancer (cf. Houghton J L. et al., PNAS 2015). PET and NIRF optical imaging offer complementary clinical applications, enabling the noninvasive whole-body imaging to localize disease and identification of tumor margins during surgery, respectively. However, the generation of such dual-labeled probes up to date has been difficult due to a lack of suitable site-specific methods; attaching two different probes by chemical means results in an almost impossible analysis and reproducibility due to the random conjugation of the probes. Furthermore, in a study of Levengood M. et al., Angewandte Chemie, 2016 a dual-drug labeled antibody, having attached two different auristatin toxins (having differing physiochemical properties and exerting complementary anti-cancer activities) imparted activity in cell line and xenograft models that were refractory to ADCs comprised of the individual auristatin components. This suggests that dual-labeled ADCs enable to address cancer heterogeneity and resistance more effectively than the single, conventional ADCs alone. Since one resistance mechanism towards ADCs include the active pumping-out of the cytotoxic moiety from the cancer cell, another dual-drug application may include the additional and simultaneous delivery of a drug that specifically blocks the efflux mechanism of the cytotoxic drug. Such a dual-labeled ADC could thus help to overcome cancer resistance to the ADC more effectively than conventional ADCs.

Similar structures in which alkynes or tetrazine/trans-cyclooctenes are being used as linker are equally suitable and covered by the scope and gist of the present invention.

It is important to understand that in some linker peptides shown herein, the moiety at the C-terminus is simply designated as N$_3$. However, this should be understood as an abbreviation of Lys(N$_3$). For example, RAKAR(N$_3$) or ArgAlaLysAlaArg(N$_3$) does actually mean RAK$_1$ARK$_2$, with K$_2$=Lys(N$_3$), or ArgAlaLysAlaArgLys(N$_3$) (SEQ ID NO:1).

It is furthermore important to understand that in different linker peptides shown herein, the C-terminus and/or the N-terminus may or may not be protected, even if shown otherwise. Protection can be accomplished by amidation of the former, and/or acetylation of the latter. In the context of the present invention, both the protected and unprotected linker peptides are encompassed. For example RAKARK(N$_3$) does indeed encompass four variants, with a) both termini protected as discussed above, b) only the N-terminus or the C-terminus protected as discussed above, or c) both termini unprotected.

The question whether or not the C- and/or N-terminus is amidated and/or acetylated is a practical question, depending on the conjugation conditions (buffer, medium, reactivity of the other reaction components, etc).

Figure 8A:
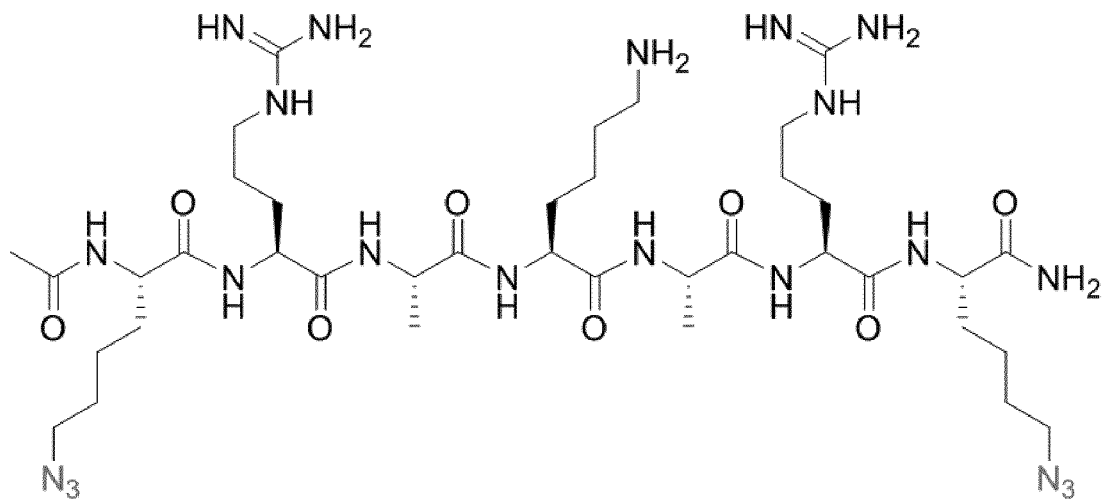
Figure 8B:
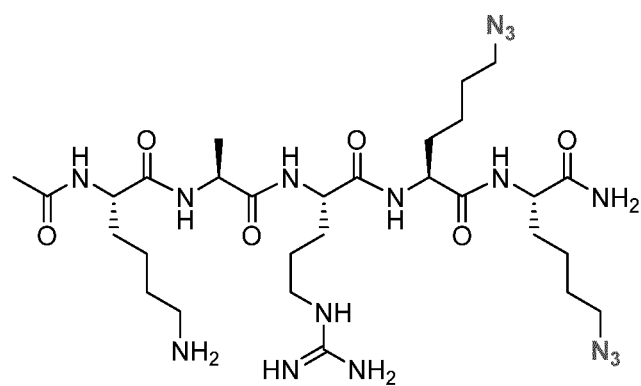

FIG. 8A and FIG. 8B show a possible linker structures with two Azide linker moieties. FIG. 8A shows Lys(N$_3$)ArgAlaLysAlaArgLys(N$_3$) (K$_1$RAK$_2$ARK$_3$, with K$_1$ and K$_3$=Lys(N$_3$)) (SEQ ID NO:23). FIG. 8B shows LysAlaArgLys(N$_3$)Lys(N$_3$) (K$_1$RK$_2$K$_3$; with K$_2$ and K$_3$=Lys(N$_3$)) (SEQ ID NO:24). In such way, an antibody payload ratio of 4 can be obtained. The presence of the charged Arg residues helps to keep hydrophobic payloads in solution.

It is important to understand that in some linker peptides shown herein, the moiety at the C-terminus is simply designated as N$_3$. However, this should be understood as an abbreviation of Lys(N$_3$). For example, RAKAR(N$_3$) or ArgAlaLysAlaArg(N$_3$) does actually mean RAK$_1$ARK$_2$, with K$_2$=Lys(N$_3$), or ArgAlaLysAlaArgLys(N$_3$) (SEQ ID NO:1).

It is furthermore important to understand that in different linker peptides shown herein, the C-terminus and/or the N-terminus may or may not be protected, even if shown otherwise. Protection can be accomplished by amidation of the former, and/or acetylation of the latter. In the context of the present invention, both the protected and unprotected linker peptides are encompassed. For example RAKARK(N$_3$) does indeed encompass four variants, with a) both termini protected as discussed above, b) only the N-terminus or the C-terminus protected as discussed above, or c) both termini unprotected.

FIG. 9 shows further linkers that are suitable for MTG-mediated conjugation to native antibodies. Structure 1 is SEQ ID NO:2, Structure 2 is SEQ ID NO:3, Structure 3 is SEQ ID NO:4, and Structure 4 is SEQ ID NO:5 (see table below for sequences). These linkers structures contain a linking moiety (azide, N$_3$) suitable for click-chemistry based attachment of the functional payload in a second step, or a Cys-residue which provides a thiol group suitable for attachment to a maleimide. Since these structures are based on peptides, that chemistry is well-understood and which is assembled from building blocks of single amino acids, new linkers can rapidly and easily be synthesized and evaluated.

|   | Sequence, residue for transglutaminase reaction in bold print | | Linking moiety B | SEQ ID NO |
|---|---|---|---|---|
| 1 | ArgAlaLysLys(N$_3$) | RAK$_1$K$_2$, with K$_2$ = Lys(N$_3$)) | Lys(N$_3$)) | SEQ ID NO: 2 |
| 2 | ArgAlaLysXaa(N$_3$) | RAKX, with X = Xaa(N$_3$), Xaa is 4-Azido-L-homoalanine | Xaa(N$_3$) | SEQ ID NO: 3 |

-continued

| | Sequence, residue for transglutaminase reaction in bold print | | Linking moiety B | SEQ ID NO |
|---|---|---|---|---|
| 3 | ArgAlaLys[PEG]$_3$(N$_3$) | RAK[PEG]$_3$N$_3$, with [PEG]$_3$ = triethylenglycol | [PEG]$_3$N$_3$ | SEQ ID NO: 4 |
| 4 | ArgAlaLysCys | RAKC | Cysteine | SEQ ID NO: 5 |

Figure 10:
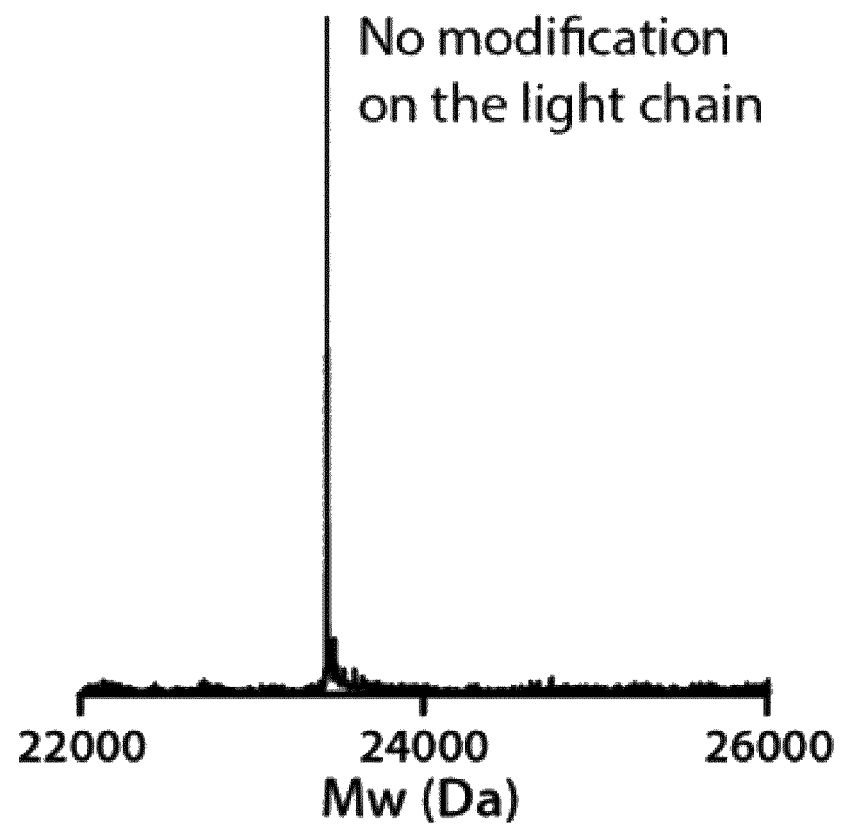

FIG. 10 shows that the light chain of IgG1 antibodies is not modified by the conjugation. Shown is the deconvoluted LC-MS spectra of a IgG1 light chain.

Figure 11:
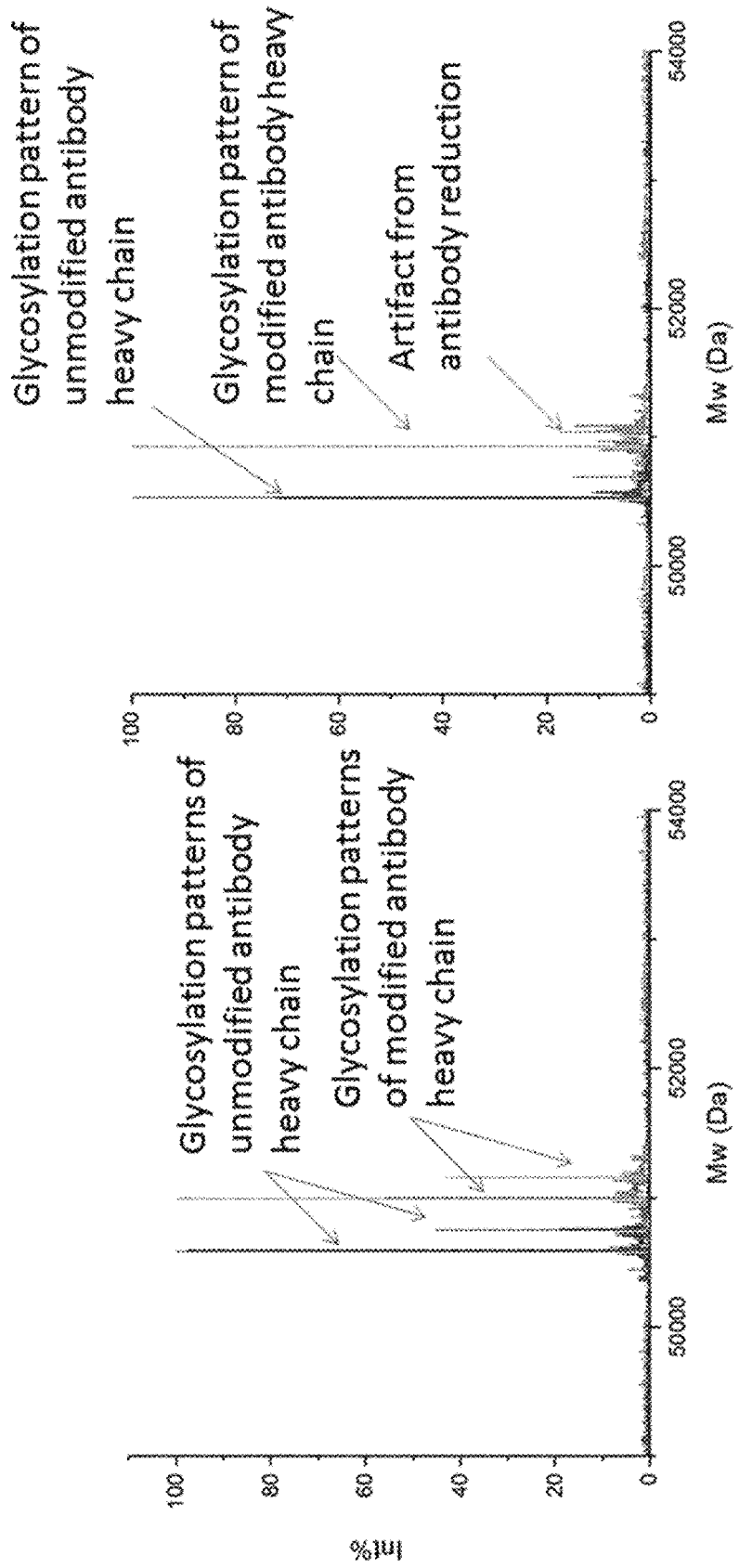

FIG. 11 shows deconvoluted LC-MS spectra of two different native IgG1 heavy chains selectively modified with an N$_3$-functional peptide. From the spectra it can be seen that both heavy chains got selectively and quantitatively (>95%) modified with only one peptide-linker since the observed mass difference corresponds to the expected peptide mass shift.

Figure 12:
Figure 12:
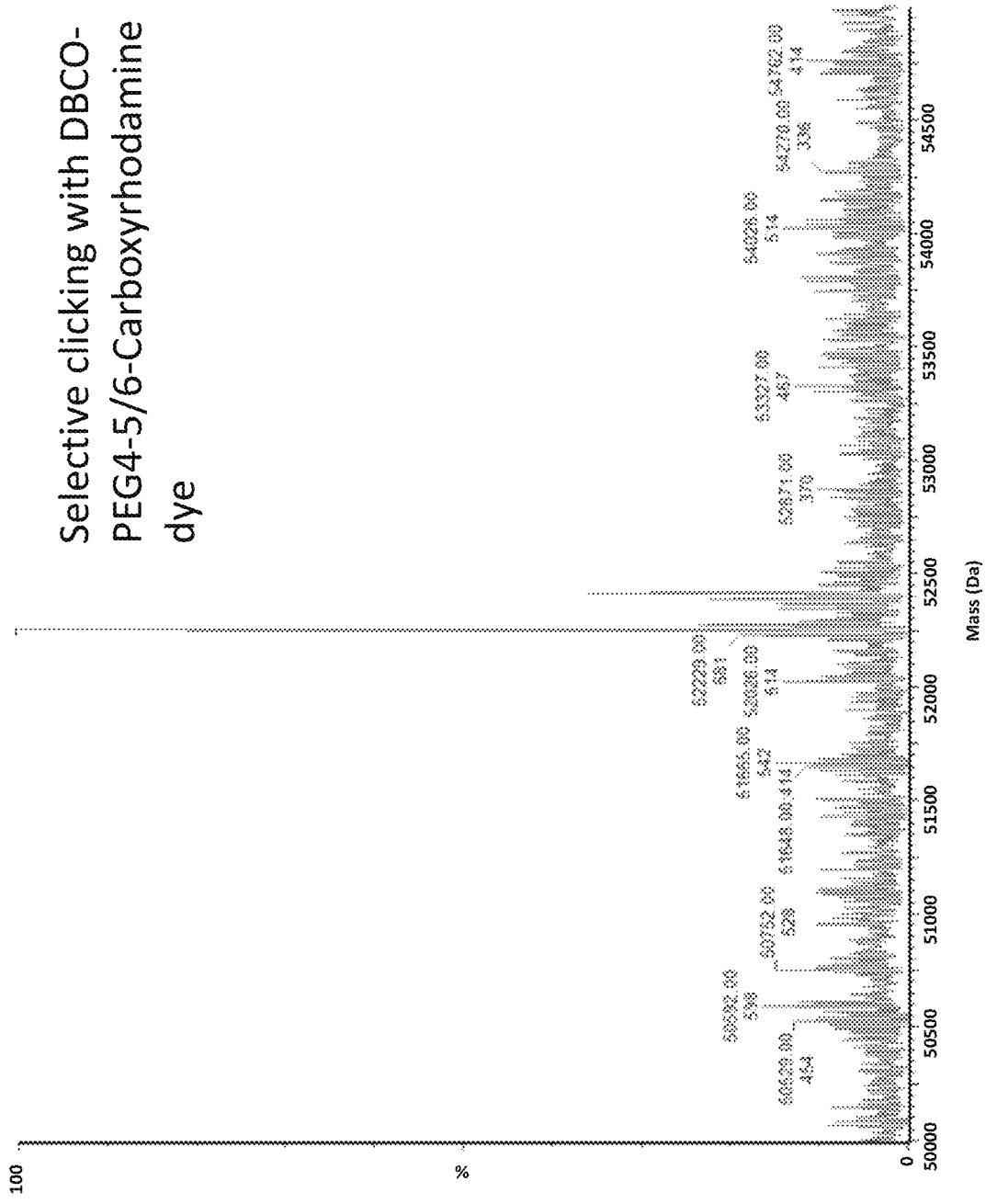

FIG. 12 shows the results of a conversion/clicking experiment (>95%) of different DBCO-functional probes (FAM- and Carboxyrhodamine-dye) to azide-functionalized native IgG1 antibody; this yields a sites-specifically modified, native IgG1 antibody, selectively modified at a single residue (Q295).

Figure 13B:
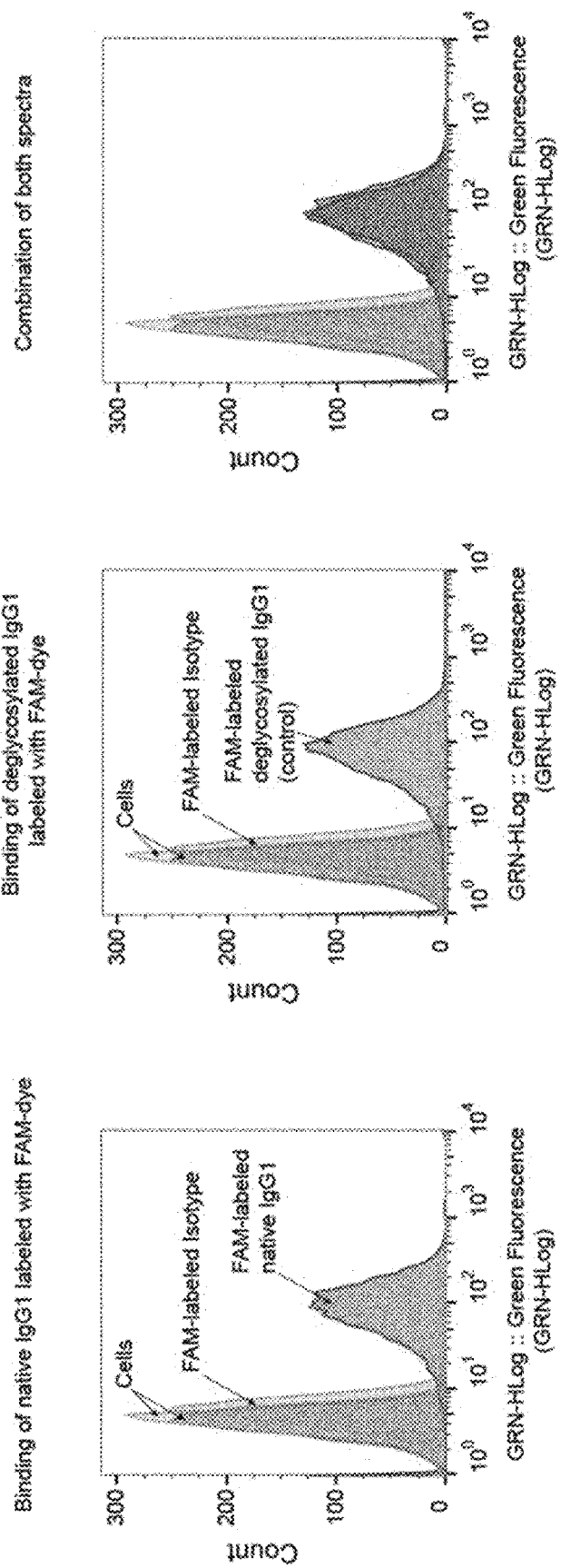

FIG. 13A and FIG. 13B show the results of a flow-cytometry experiment with two native IgG1 using deglycosylated variants as reference. FAM-dye was used. As peptide: RAKAR-K(N$_3$) (SEQ ID NO:1) was used and DBCO-PEG4-5/6-FAM-dye for clicking. According to LC-MS a clicking of >95% efficiency was achieved.

FIG. 14 shows an overview of the Ig C$_H$2 domain with the different numbering schemes. For the purposes of the present invention, the EU numbering is being used.

Figure 15:
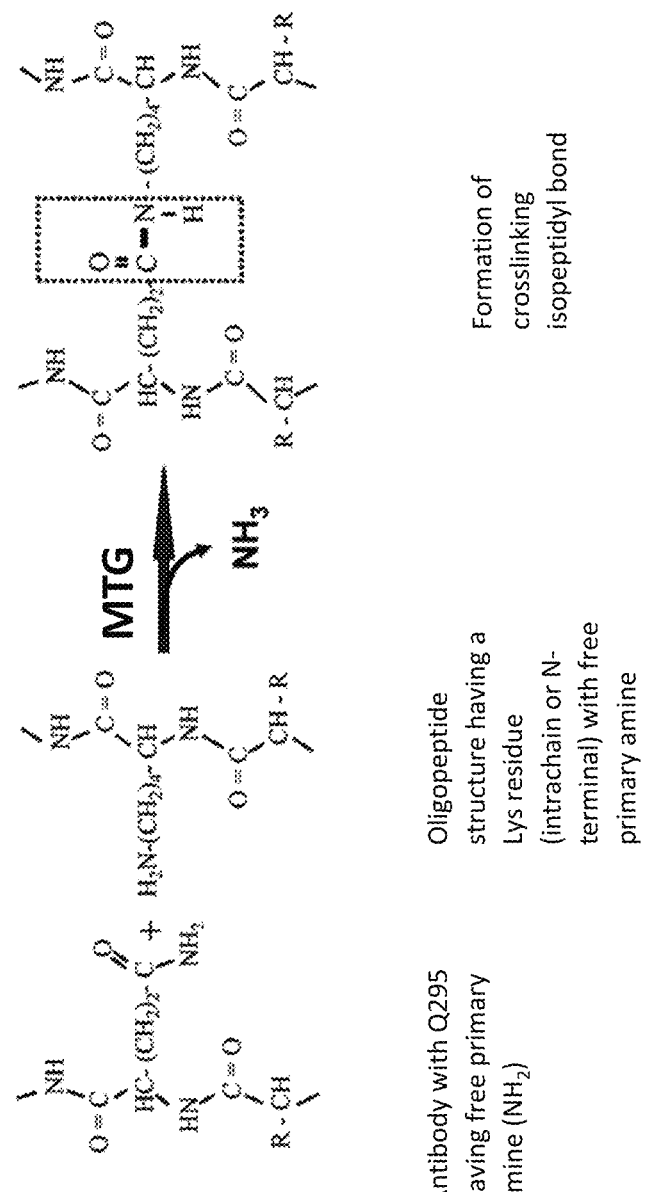

FIG. 15 shows a transglutaminase reaction to conjugate a linker having a Lys residue (intrachain or N-/C-terminal) with a free primary amine to the free primary amine of the Q295 residue of an antibody.

Figure 16:
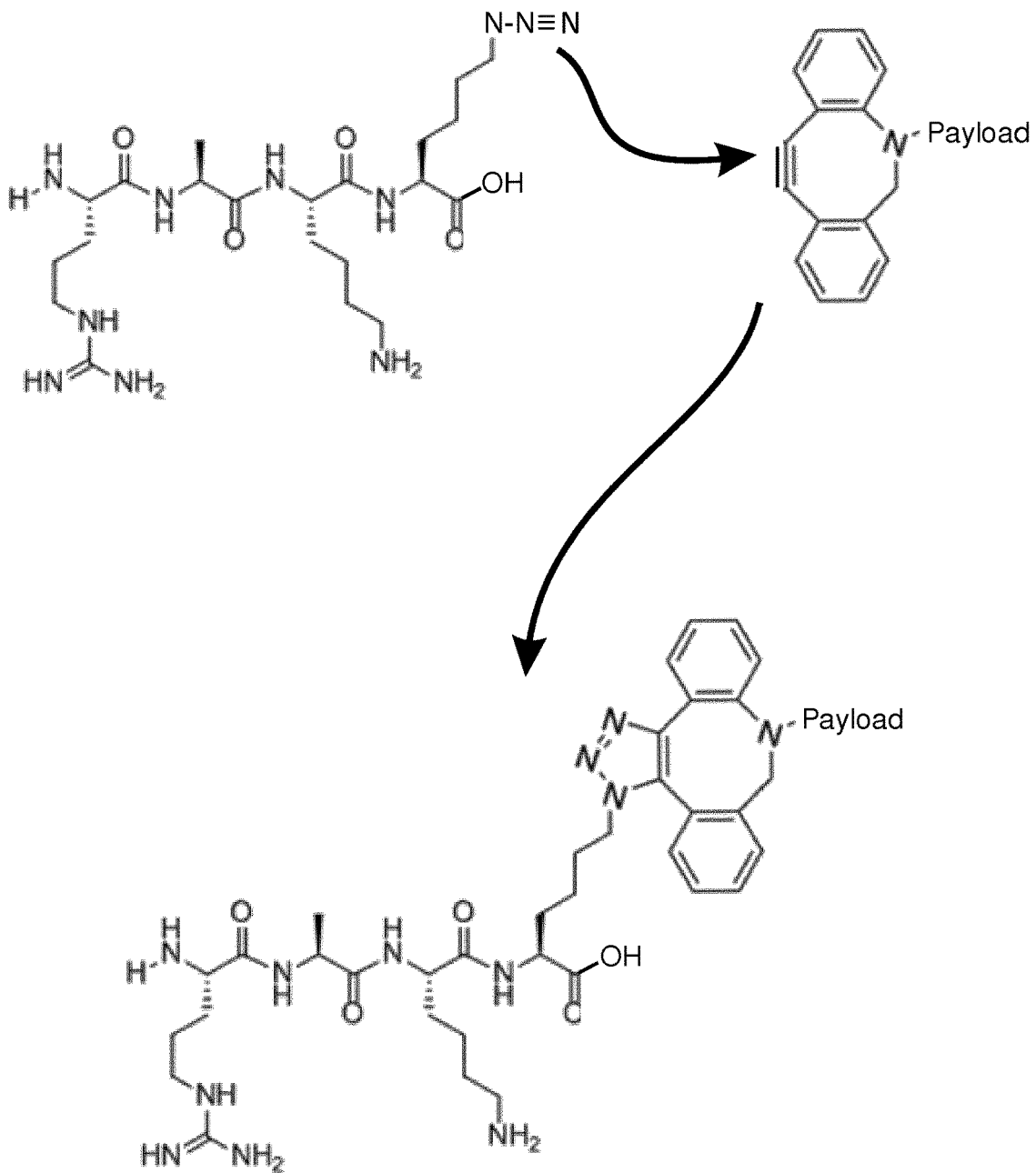

FIG. 16. Click chemistry reaction scheme (strain-promoted alkyne-azide cycloaddition (SPAAC) to conjugate the linker ArgAlaLysLys(N$_3$) (RAK$_1$K$_2$, with K$_2$=Lys(N$_3$)) (SEQ ID NO:2) to dibenzocyclooctyne labelled with a payload.

Figure 17:
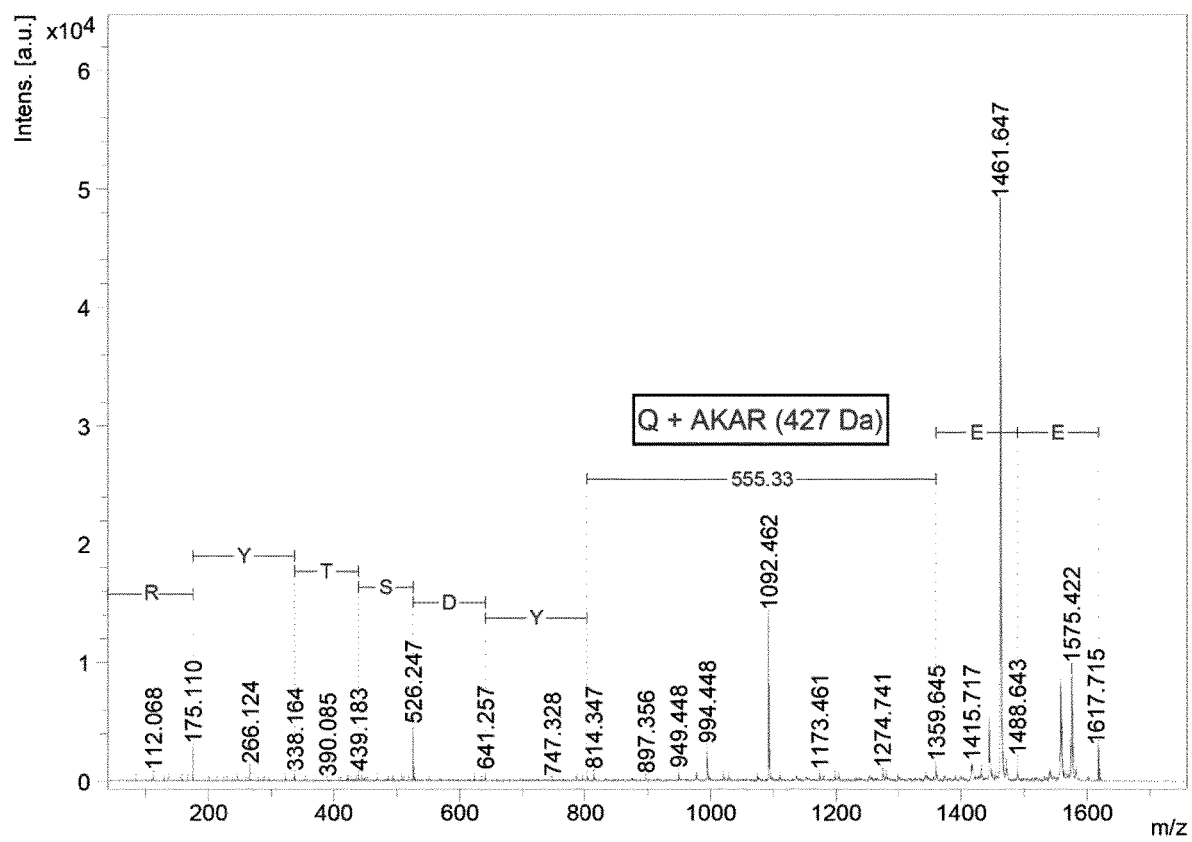

FIG. 17. Peptide mapping of ArgAlaLysAlaArg-B (RAKAR) (SEQ ID NO:30) conjugated to glycosylated IgG1 reference antibody using MTG was subjected to tryptic digestion followed by LC-MS/MS. Peptide fragmentation clearly identified Q295 in the antibody heavy chain as the site of modification within the fragment EEQYDSTYR (1*Peptide_23_AKAR, Mw: 1617.7 Da expected and measured).

Figure 18A:
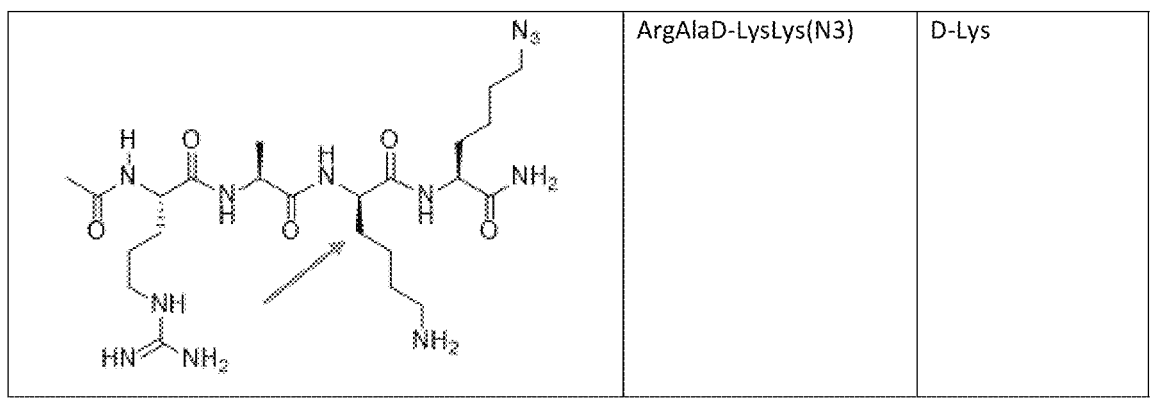

FIG. 18A-18B show different peptide linkers that can be used in the context of the present invention. FIG. 18A shows peptide linkers comprising a non-natural amino acid. FIG. 18B shows peptide linkers comprising a lysine derivative or mimetic which provides the primary amine for the transglutaminase reaction. All of these peptide variants or peptidomimetics have been derived from a ArgAlaLysLys(N$_3$) peptide (RAK$_1$K$_2$, with K$_2$=Lys(N$_3$)) (SEQ ID NO:2). Note that, instead of Lys(N$_3$), other linking moieties B can be used, as described herein elsewhere.

FIG. 19A-19B show further peptide linkers that can be used in the context of the present invention.

FIG. 20 shows further peptide linkers that can be used in the context of the present invention. ArgLys(N$_3$)Lys (SEQ ID NO:38) is a peptide that has the linking moiety Lys(N$_3$) intrachain, i.e., neither at N nor at C-terminal). LysLys(N$_3$) (SEQ ID NO:38) and LysCys (SEQ ID NO:40) are very short linkers.

Figure 21:
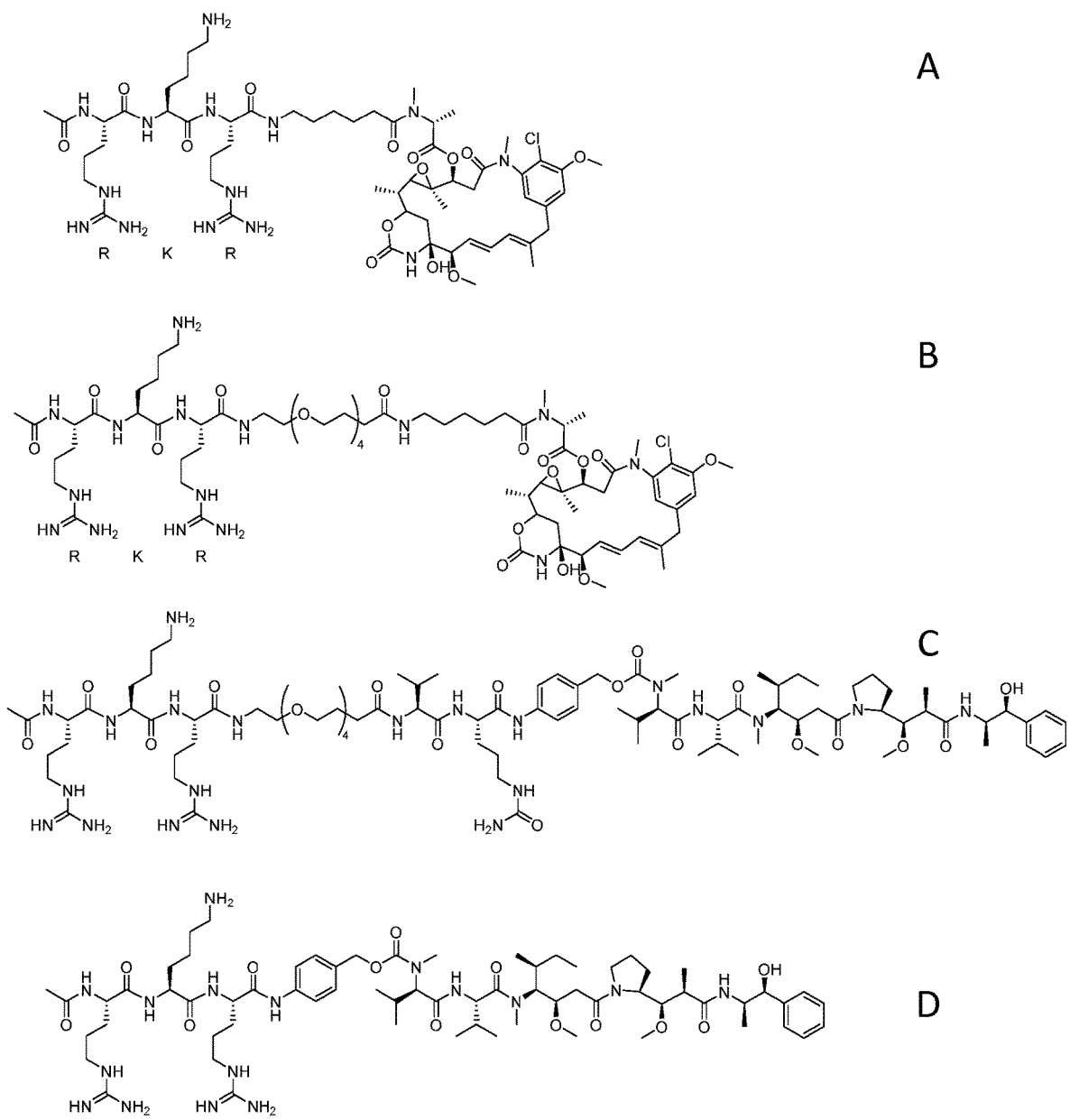

FIG. 21 shows different linker toxin constructs that can be conjugated to an antibody according to the method described herein. In all cases, the Lys residues carry the primary amine for transglutaminase conjugation FIG. 21, row A, RKR-DM1 This Figure shows the non-cleavable RKR-DM1 peptide-toxin conjugate with two arginine-groups serving to increase the solubility of the hydrophobic payload DM1. The lysine serves for the conjugation to the antibody via MTG. The Ahx-spacer serves to decouple the positively-charged arginine from the DM1, helping the latter to more efficiently bind its target since the linker is not cleavable.

FIG. 21, row B, RKR-DM1 This Figure shows the non-cleavable RKR-DM1 peptide-toxin conjugate with two arginine-groups and a PEG4-spacer, all three moieties serving to increase the solubility of the hydrophobic payload DM1. The lysine serves for the conjugation to the antibody via MTG. The PEG4 furthermore helps to decouple the positively-charged arginine from the DM1, helping the latter to more efficiently bind its target since the linker is not cleavable.

FIG. 21, row C, RKR-MMAE This Figure shows the cleavable RKR-MMAE peptide-toxin conjugate with two arginine-groups, a PEG4-spacer, a PABC-group and a val-cit sequence. The lysine serves for the conjugation to the antibody via MTG, the arginine-groups and the PEG4-spacer to increase the solubility and the PABC-group and the val-cit sequence help to release the toxin.

FIG. 21, row D, RKR-MMAE This Figure shows the cleavable RKR-MMAE peptide-toxin conjugate with two arginine-groups and a PABC-group with no PEG-spacer and val-cit sequence. Since the RKR-peptide is intrinsically degradable by peptidases, no val-cit sequence might be necessary for toxin release, and as the two arginine-groups are very hydrophilic no PEG-spacer may be needed, keeping thus the whole peptide-toxin conjugate as small as possible to minimize undesired interactions with other molecules while in blood circulation.

FIG. 22 shows results of a cellular toxicity assay as performed according to example 2. The Inhouse ADC has a similar potency against SK-BR3 cells as Kadcyla. Hence, the advantages provided by the novel linker technology (ease of manufacture, site specificity, stable stoichiometry, no need to deglycosylate that antibody) do not come at any disadvantage regarding the cellular toxicity.

Figure 23A:
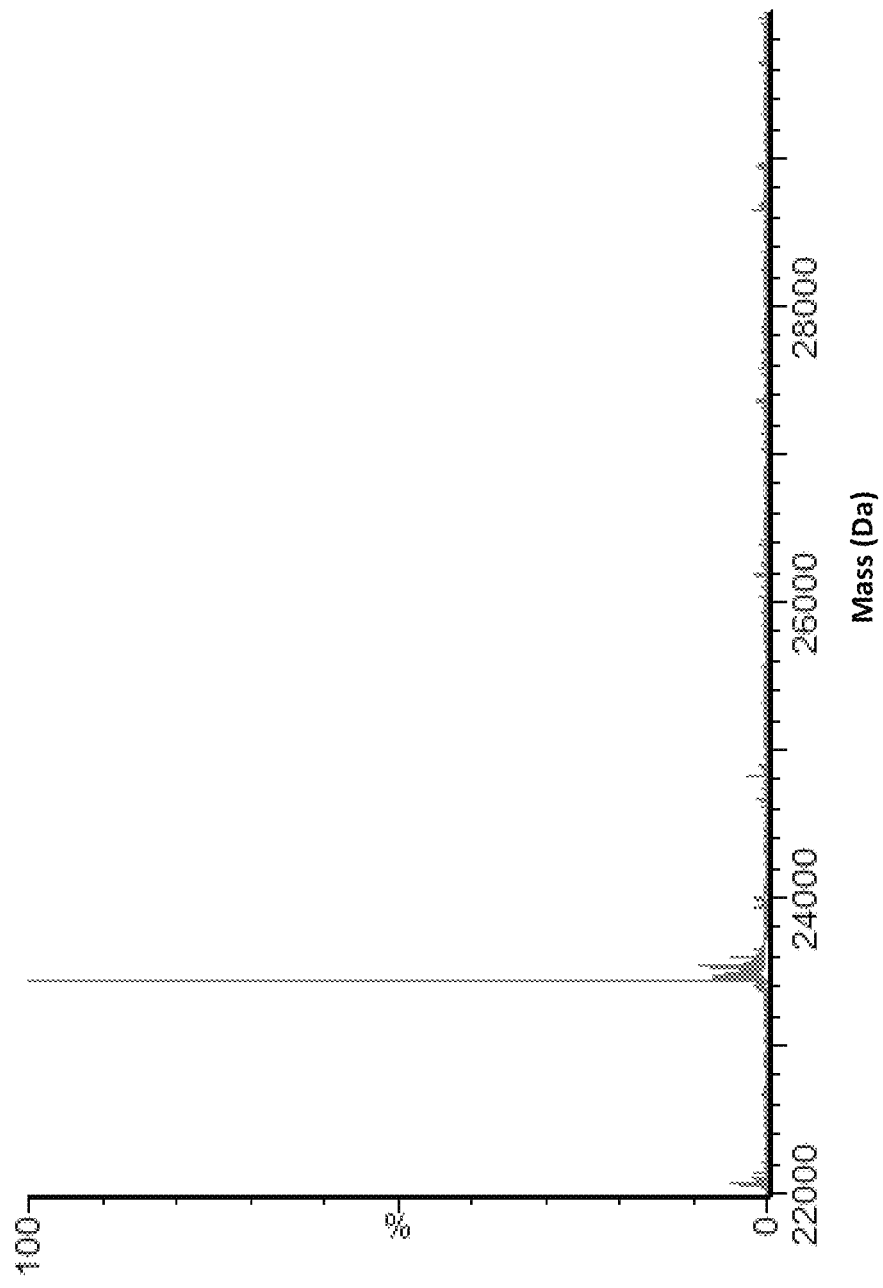
Figure 23B:
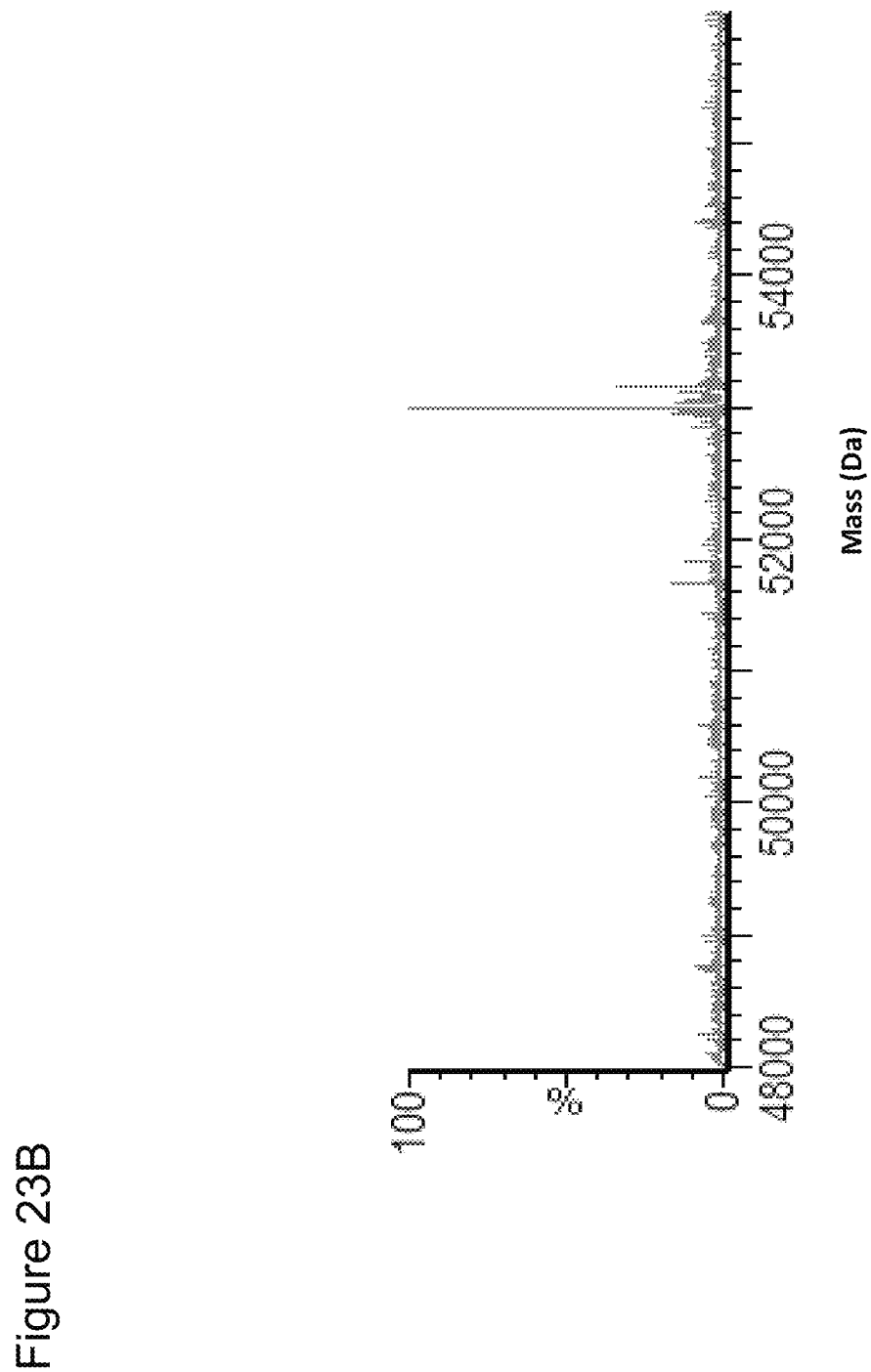

FIGS. 23A-23B show results of a dual-payload conjugation and cell-binding study (example 6). FIG. 23 A: Light chain of humanized IgG1 after dual-payload conjugation: Purity>95%. FIG. 23 B: Heavy chain of humanized IgG1 after dual-payload conjugation and attaching maleimide-NODAGA and DBCO-PEG4-Ahx-DM1: Purity>90%

Figure 24:
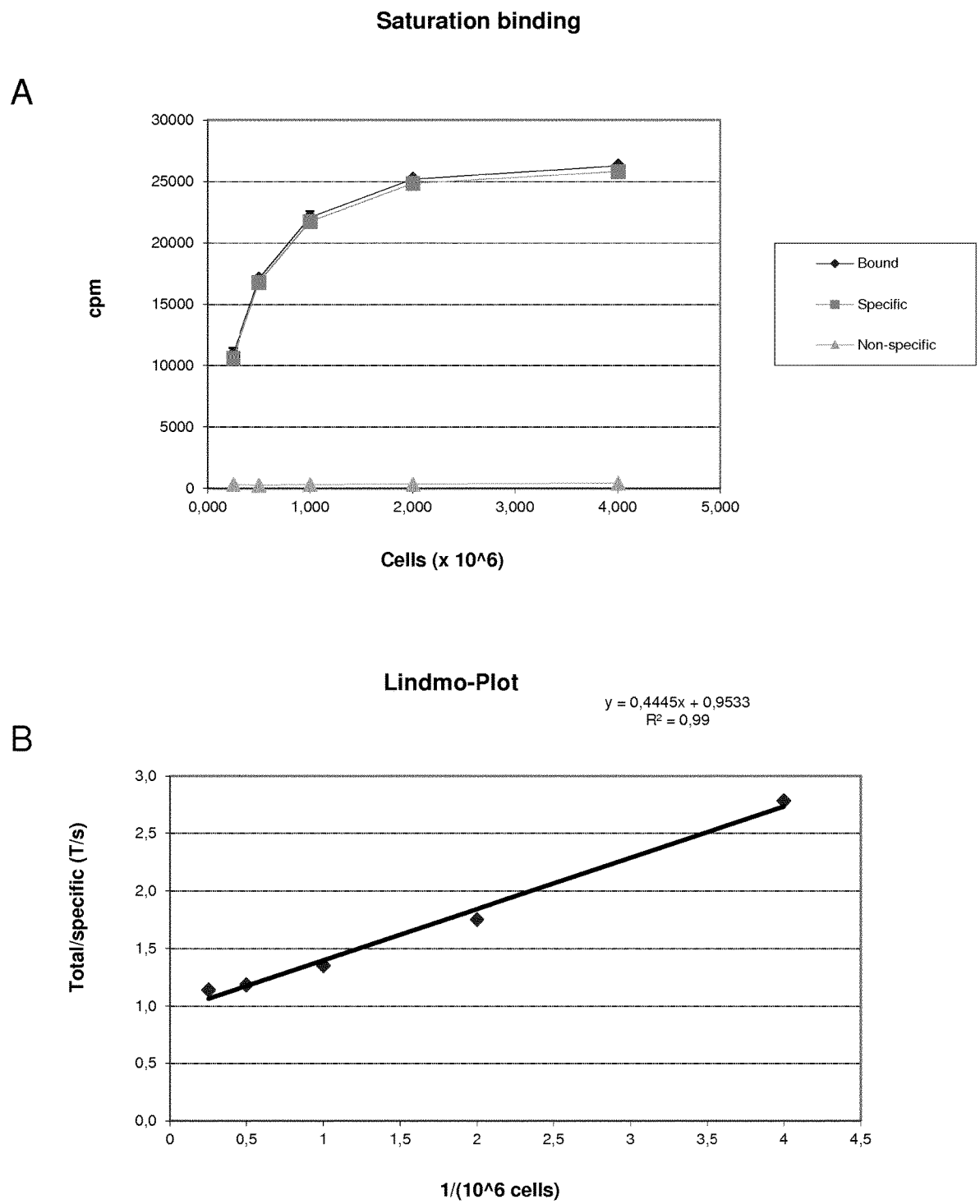

FIG. 24 shows further results of a dual-payload conjugation and cell-binding study (example 6).

Figure 25:
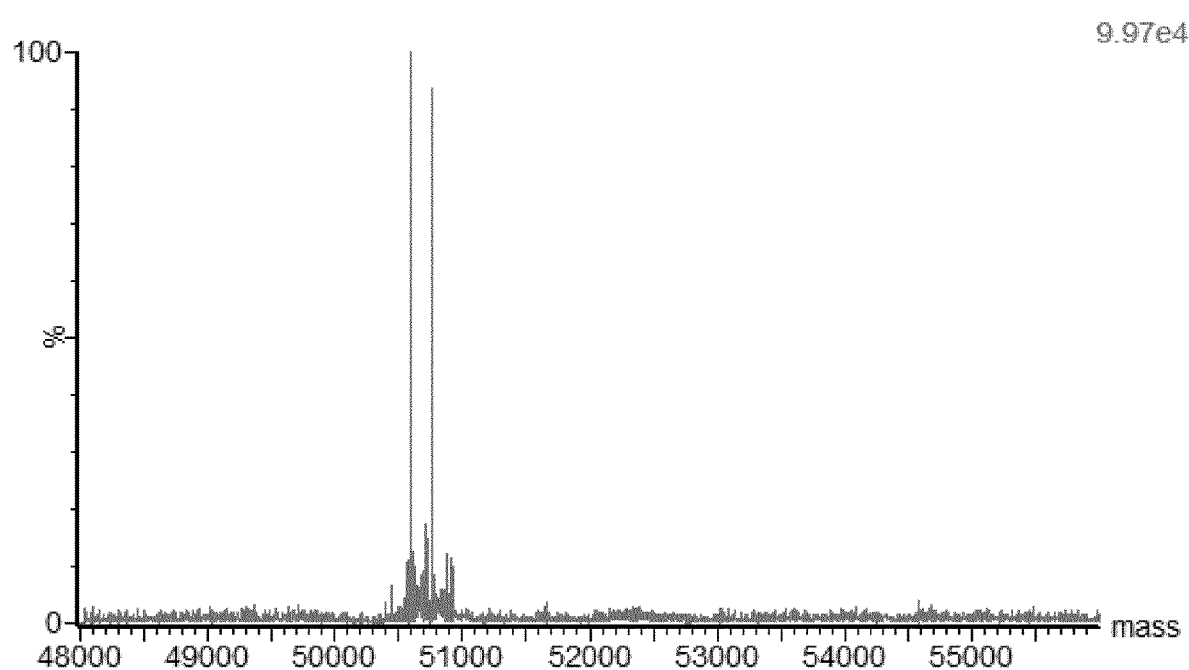

FIG. 25 shows results of a control conjugation of Ac-RβAK(N₃)—NH₂ (Ac-ArgβAlaLys(N₃)—NH₂) (i.e., a linker not containing an amino acid with a primary amine on a side chain) for conjugation to humanized IgG1 (example 7). No conjugation was detected.

Figure 26A:
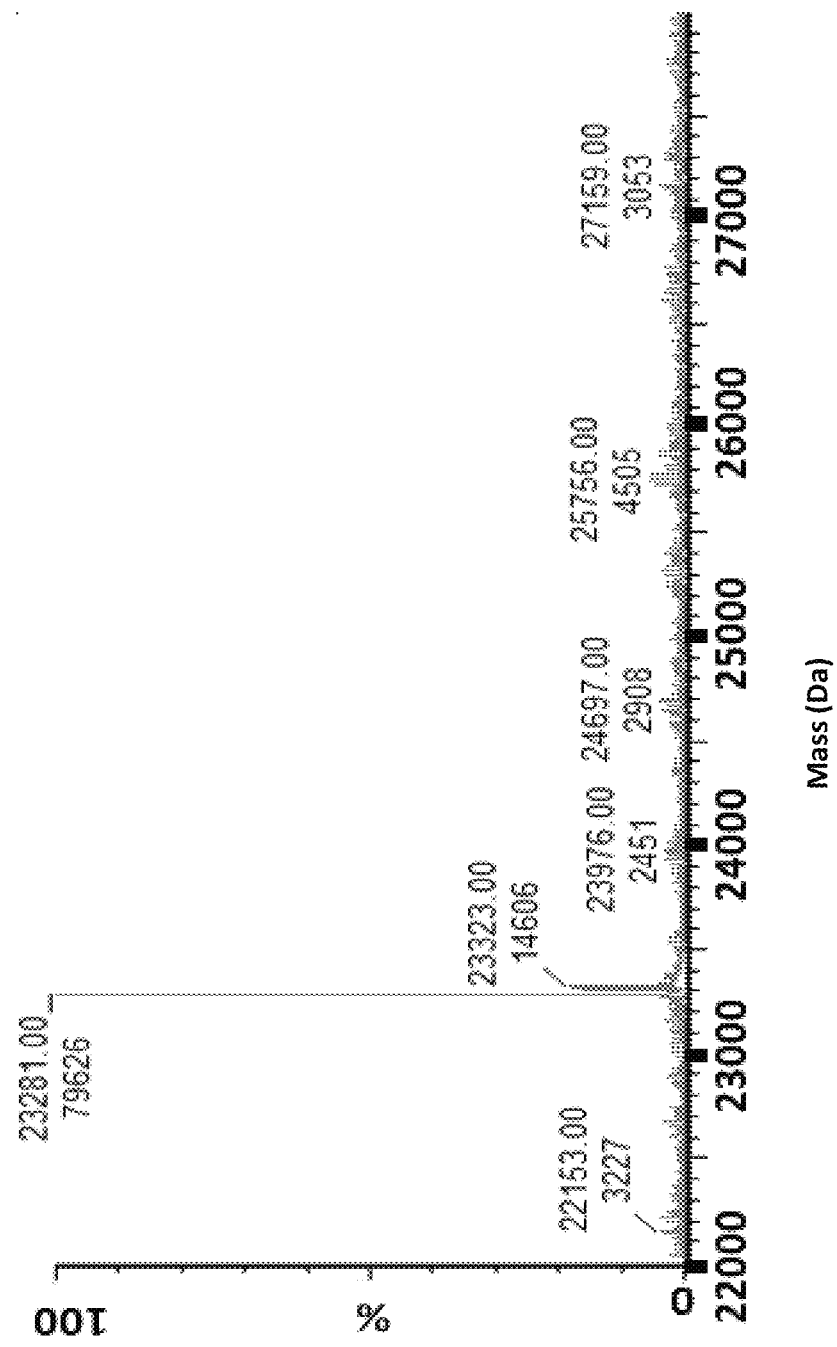
Figure 26B:
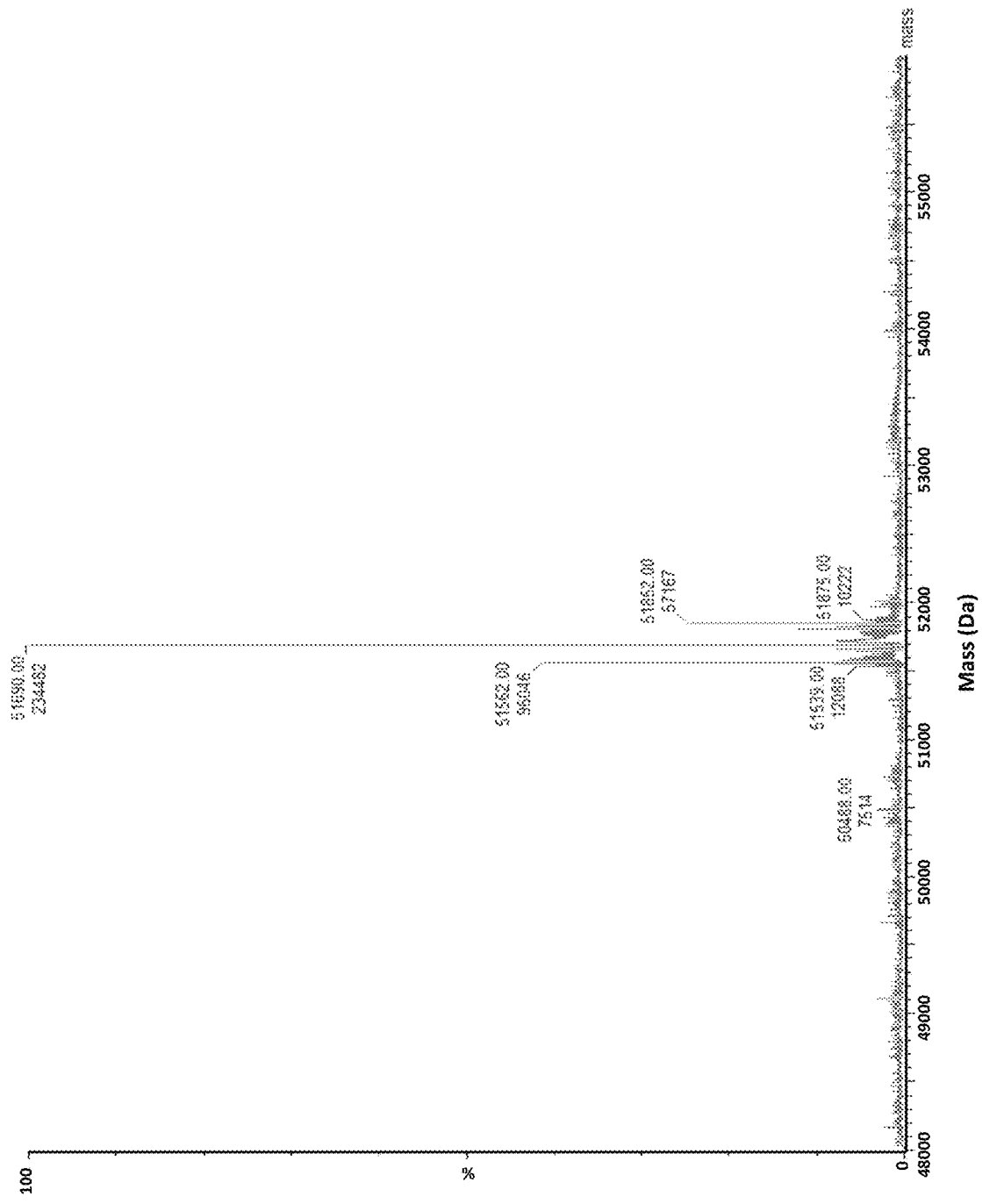
Figure 26C:
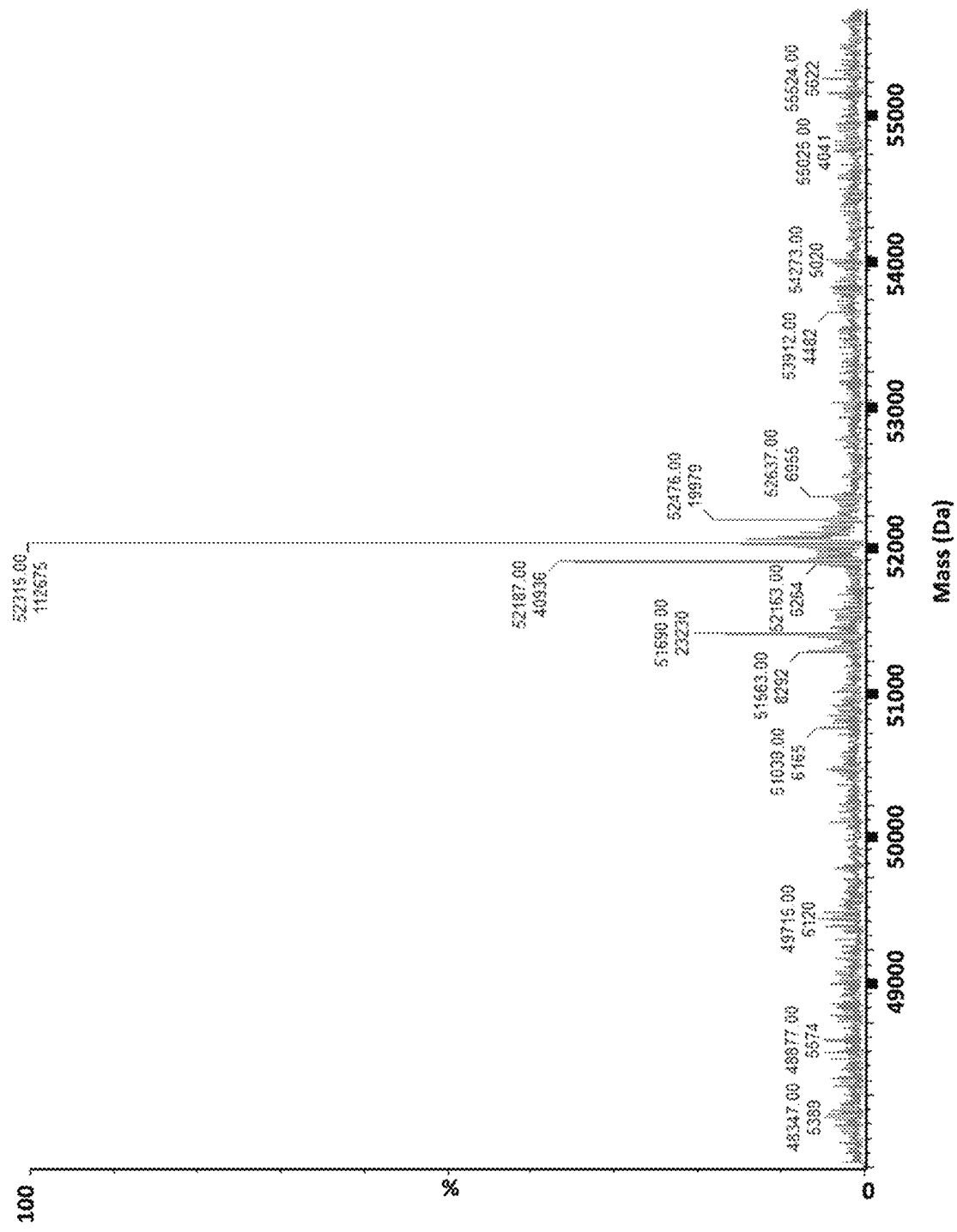

FIGS. 26A-26C show results of a conjugation experiment to human IgG4 antibody (example 8). FIG. 26A: Light chain of human IgG4: no conjugation detected. FIG. 26B: Native heavy chain of human IgG4 showing its glycosylation pattern. FIG. 26C: Native heavy chain of human IgG4 after conjugation with RAKAR, showing selective modification at a single residue. A conjugation efficiency of 85% was reached under non-optimized conditions.

Figure 27:
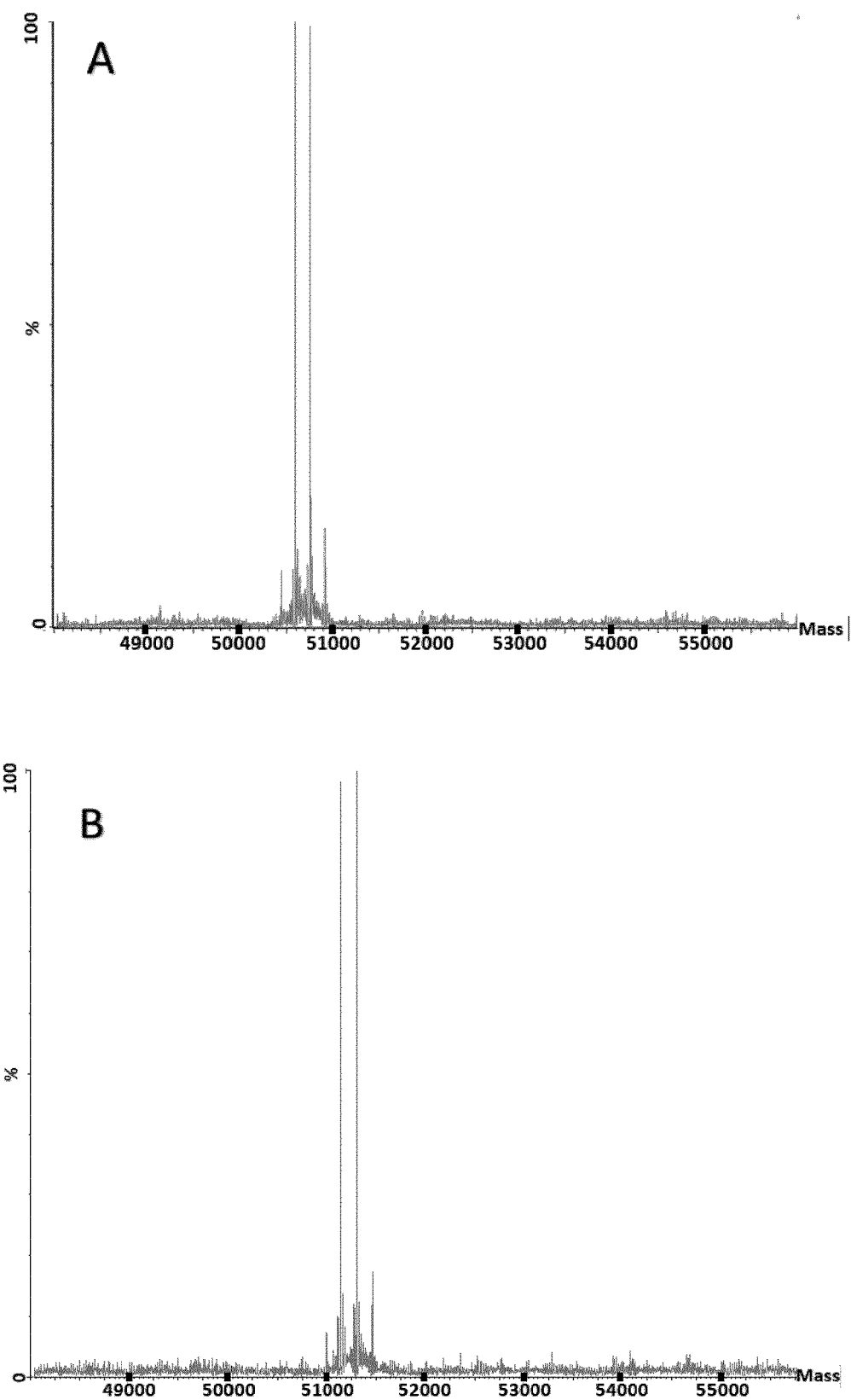

FIG. 27 shows results of an ADC preparation from a humanized IgG1, followed by LC-MS (example 9). FIG. 27A: Native heavy chain of humanized IgG1 showing its native glycosylation pattern. FIG. 27B: Native heavy chain of humanized IgG1 after conjugation with Ac-RAK-Lys(N₃)—NH₂ (SEQ ID NO:2). A conjugation efficiency of 98% was achieved. FIG. 27C: Native heavy chain of humanized IgG1 after conjugation with Ac-RAK-Lys(N₃)—NH₂ (SEQ ID NO:2) and clicked with DBCO-PEG4-Ahx-DM1. A clicking efficiency of 98% was achieved.

Figure 28:
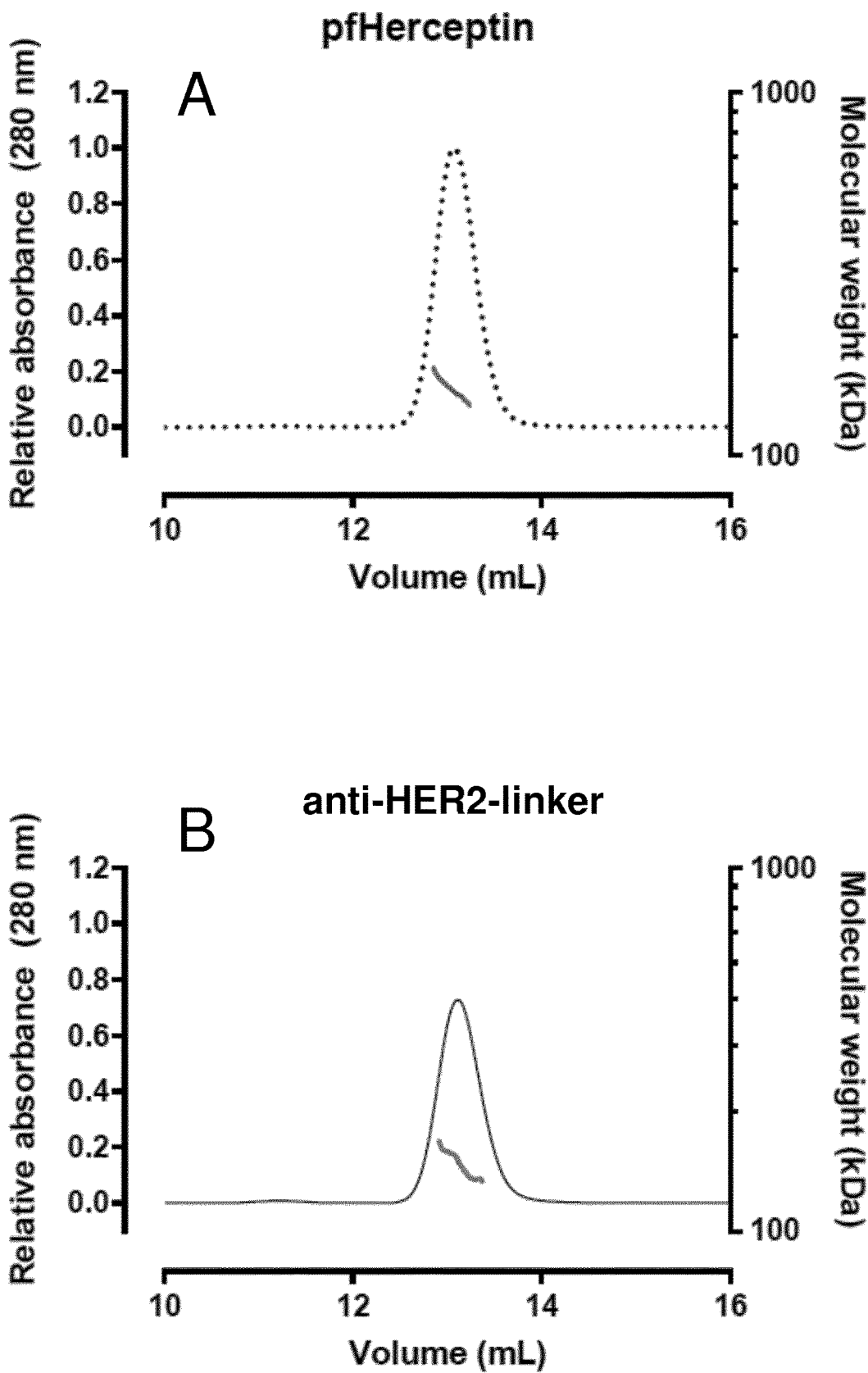

FIG. 28 shows results of SEC-MALS experiments. FIG. 28 A Herceptin, FIG. 28 B: anti-HER2-linker construct using the claimed linker technology FIG. 28 C: Inhouse ADC, FIG. 28D: Kadcyla®

DETAILED DESCRIPTION OF THE INVENTION

Before the invention is described in detail, it is to be understood that this invention is not limited to the particular components or process steps of the methods described as such devices and methods may vary. It is also to be understood that the terminology used herein is for purposes of describing particular embodiments only, and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the documents referred to herein is incorporated by reference. This refers, particularly, for documents that disclose standard or routine methods. In that case, the incorporation by reference has mainly the purpose to provide sufficient enabling disclosure, and avoid lengthy repetitions.

According to a first aspect, a method for generating an antibody-payload conjugate by means of a microbial transglutaminase (MTG) is provided, which method comprises a step of conjugating a linker having a primary amine residue, said linker having the peptide structure (shown in N->C direction)

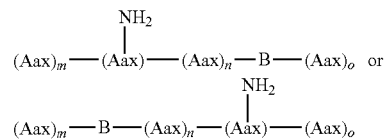

to a Gln residue comprised in the heavy or light chain of an antibody, wherein
  m is an integer between ≥0 and ≤12
  n is an integer between ≥0 and ≤12
  o is an integer between ≥0 and ≤12
  m+n+o≥0,
  Aax can be any naturally or non-naturally occurring L- or D-amino acid, or amino acid derivative or mimetic, and
  B is a payload or a linking moiety,
and wherein

is an amino acid, amino acid derivative or amino acid mimetic comprising a side chain having a primary amine group.

As used herein, the term "primary amine" relates to an amine substituted with two hydrogen atoms, of the general formula R—NH₂.

It is important to understand that in different linker peptides shown herein, the C-terminus and/or the N-terminus may or may not be protected, even if shown otherwise. Protection can be accomplished by amidation of the former, and/or acetylation of the latter. In the context of the present invention, both the protected and unprotected linker peptides are encompassed.

According to one embodiment,

is Lysine or a Lysine derivative or a Lysine mimetic. Preferably, said lysine or Lysine derivative or Lysine mimetic is an amino acid with a primary amine (both D and L form), as shown in the following table 1:

TABLE 1

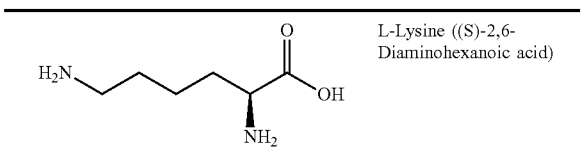

L-Lysine ((S)-2,6-Diaminohexanoic acid)

TABLE 1-continued

| Structure | Name |
|---|---|
| (D-Lysine structure) | D-Lysine ((R)-2,6-Diaminohexanoic acid) |
| (Ornithine structure) | Ornithine (2,5-Diaminopentanoic acid), both in the L and D configuration |
| (L-β-Homolysine structure) | L-β-Homolysine (S)-3,7-Diaminoheptanoic acid |
| (Homolysine structure) | Homolysine |
| (Dab structure) | α,γ-diaminobutyric acid (Dab) both in the L and D configuration (shown is L) |

Hence, in the simplest form, B can be directly conjugated to the Lys or a Lysine derivative or Lysine mimetic. In such case, m+n+o=0.

Two examples for such embodiments, where Lysine or a Lysine derivative or Lysine mimetic is directly conjugated to a toxin, are shown in the following:

Lys-MMAE

Lys-DM1

In some embodiments, the N- or C-Terminus of the peptide structure can be protected with suitable protection groups (amidated or acetylated).

In another embodiment, the Lys derivative can be an organic molecule that comprises a primary amine and is accepted by a transglutaminase enzyme.

The linker structure can hence be any of the examples in the following table 2 (where Lys stands for Aax-NH$_2$, or lysine or a lysine derivative or mimetic):

TABLE 2

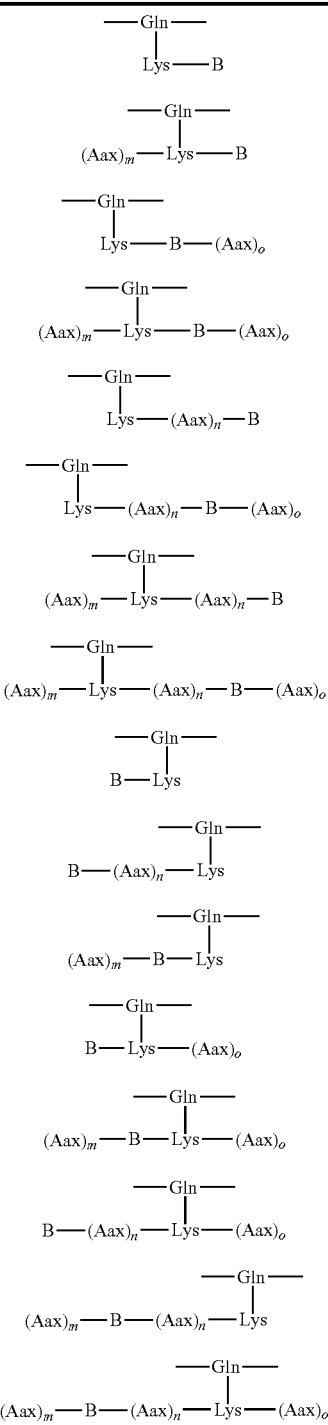

The inventors have shown that this process is suitable to very cost effectively and quickly produce site-specific antibody-payload conjugates (24-36 hrs), and hence allows the production of large libraries of such molecules, and subsequent screening thereof in high throughput screening systems.

In contrast thereto, a Cys engineering process in which an antibody payload conjugate is produced where the payload is conjugated to the antibody via a genetically (molecularly) engineered Cys residue needs at least about 3-4 weeks.

In general, the method allows to conjugate a large number of payloads to an antibody. For each payload, a suitable peptide linker structure can be identified from a large linker pool to deliver optimal clinical and non-clinical characteristics. This is not possible in other methods where the linker structure is fixed.

As used herein, the term "non-naturally occurring amino acid", or amino acid analog, relates to amino acids having the general structure —NH—CHR—CO—, but which do not occur in a biological protein. The term comprises, but is not restricted to, β-alanine, α-aminobutyric acid, γ-aminobutyric acid, α-aminoisobutyric acid, ε-lysine, ornithine, hydroxyproline, agmatine, {S}-2-amino-4-((2-amino)pyrimidinyl)butanoic acid, 4-amino butyric acid, 4-amino-3-hydroxy-5-phenylpentanoic acid, 4-amino-3-hydroxy-6-methylheptanoic acid, 6-aminohexanoic acid, alpha-aminoisobutyric acid, benzophenone, t-butylglycine, citruiline, cyclohexyialanine, desamino tyrosine, L-(4-guanidino)phenylalanine, homoarginine, homocysteine, homoserine, homolysine, n-formyl tryptophan, norleucine, norvalene, phenylglycine, (S)-4-piperidyl-N-amidino)glycine, ornithine, parabenzoyl-L-phenylalanine, sarcosine, statine, 2-thienyl alanine, and/or D-isomers of the naturally or non-naturally occurring amino acids.

The term "D-amino acid" is understood to comprise the D-counterparts of both naturally occurring amino acids as well as of non-naturally occurring amino acids.

In one embodiment, the linker having the peptide structure is not cleavable by cathepsin B. In one further embodiment, the linker having the peptide structure does not comprise a valine-alanine motif or a valine-citrullin motif.

One typical dipeptide structure used in ADC linkers, yet devoid of a Lys residue, is the valine-citrulline motif, as e.g. provided in Brentuximab Vedotin, and discussed in Dubowchik and Firestone 2002. This linker can be cleaved by cathepsin B to release the toxin at the side of disease. The same applies to the valine-alanine motif, which is for example provided in SGN-CD33A.

In one further embodiment, the linker does not comprise polyethylene glycol or a polyethylene glycol derivative.

Polyethylene glycol (PEG) is a polyether compound with many applications from industrial manufacturing to medicine. PEG is also known as polyethylene oxide (PEO) or polyoxyethylene (POE), depending on its molecular weight. The structure of PEG is commonly expressed as H—(O—CH$_2$—CH$_2$)$_n$—OH.

It is hence important to understand that, because B can either be a payload or a linking moiety, the method according to the invention has two major embodiments, as shown in the following table 3:

TABLE 3

| Linker peptide | Process type | Steps |
|---|---|---|
| (Aax)m-Lys-(Aax)n-Payload | One-step conjugation | step 1: conjugation of linker comprising the payload to Gln residue in antibody |

TABLE 3-continued

| Linker peptide | Process type | Steps |
|---|---|---|
| (Aax)m-Lys-(Aax)n-Linking moiety | Two-step conjugation | step 1: conjugation of linker comprising the Linking moiety to Gln residue in antibody<br>step 2: conjugation of payload to Linking moiety |

According to one embodiment of the invention, $m+n+o \leq 25$, preferably $\leq 20$, more preferably $\leq 15$, more preferably $\leq 12$, more preferably $\leq 10$, more preferably $\leq 8$, more preferably $\leq 7$, more preferably $\leq 6$, more preferably $\leq 5$, more preferably $\leq 4$.

According to one further embodiment of the invention, the payload or linking moiety is conjugated to a Gln residue which was introduced into the heavy or light chain of the antibody by molecular engineering.

According to one further embodiment of the invention, the payload or linking moiety is conjugated to a Gln in the Fc domain of the antibody According to one further embodiment of the invention, the payload or linking moiety is conjugated to the Gln residue Q295 (EU numbering) of the $C_H2$ domain of the antibody.

It is important to understand that Q295 is an extremely conserved amino acid residue in IgG type antibodies. It is conserved in human IgG1, 2, 3, 4, as well as in rabbit and rat antibodies amongst others. Hence, being able to use Q295 is a considerable advantage for making therapeutic antibody-payload conjugates, or diagnostic conjugates where the antibody is often of non-human origin. The method according to the invention does hence provide an extremely versatile and broadly applicable tool.

Further, it has been shown that engineered conjugates using Q295 for payload attachment demonstrate good pharmacokinetics and efficacy (Lhospice et al. 2015), and are capable of carrying even unstable toxins prone for degradation (Dorywalska et al. 2015). It thus expected that similar effects will be seen with this site-specific method since the same residue is modified, but of glycosylated antibodies. Glycosylation may further contribute to overall ADC stability, removal of the glycan moieties as with the mentioned approaches has been shown to result in less-stable antibodies (Zheng et al. 2011).

According to one further embodiment of the invention, the antibody to which the payload or linking moiety is conjugated is glycosylated.

Typical IgG shaped antibodies are N-glycosylated in position N297 (Asn-X-Ser/Thr-motif) of the $C_H2$ domain.

In the literature discussing the conjugation of linkers to a $C_H2$ Gln residue by means of a transglutaminase, the focus has been on small, low-molecular weight substrates, However, in the prior art literature, to accomplish such conjugation, a deglycosylation step in position N297, or the use of an aglycosylated antibody, is always described as necessary (WO 2015/015448; WO 2017/025179; WO 2013/092998).

Quite surprisingly, and against all expectations, however, site-specific conjugation to Q295 of glycosylated antibodies is indeed efficiently possible by using the above discussed oligopeptide structure.

Though Q295 is very close to N297, which is, in its native state, glycosylated, the method according to the invention, using the specified linker, still allows the conjugation of the linker or payload thereto.

However, as shown, the method according to the invention does not require an upfront enzymatic deglycosylation of Q295, nor the use of an aglycosylated antibody, nor a substitution of N297 against another amino acid, nor the introduction of a T299A mutation to prevent glycosylation.

These two points provide significant advantages under manufacturing aspects. An enzymatic deglycosylation step is undesired under GMP aspects, because it has to be made sure that the both the deglycosylation enzyme (e.g., PNGase F) as well as the cleaved glycan have to be removed from the medium.

Furthermore, no genetic engineering of the antibody for payload attachment is necessary, so that sequence insertions which may increase immunogenicity and decrease the overall stability of the antibody can be avoided.

The substitution of N297 against another amino acid has unwanted effects, too, because it may affect the overall stability of the entire Fc domain (Subedi et al, 2015), and the efficacy of the entire conjugate as a consequence that can lead to increased antibody aggregation and a decreased solubility (Zheng et al. 2011) that particularly gets important for hydrophobic payloads such as PBDs. Further, the glycan that is present at N297 has important immunomodulatory effects, as it triggers antibody dependent cellular cytotoxicity (ADCC) and the like. These immunomodulatory effects would get lost upon deglycosylation or any of the other approaches discussed above to obtain an aglycosylated antibody. Further, any sequence modification of an established antibody can also lead to regulatory problems, which is problematic because often times an accepted and clinically validated antibody is used as a starting point for ADC conjugation.

Hence, the method according to the invention allows to easily and with without disadvantages make stoichiometrically well-defined ADCs with site specific payload binding.

According to one further embodiment of the invention, the net charge of the linker is neutral or positive.

The net charge of a peptide is usually calculated at neutral pH (7.0). In the simplest approach, the net charge is determined by adding the number of positively charged amino acids residues (Arg and Lys and optionally His) and the number of negatively charged ones (Asp and Glu), and calculate the difference of the two groups.

According to one further embodiment of the invention, the linker does not comprise negatively charged amino acid residues.

Preferably, the oligopeptide does not comprise the negatively charged amino acid residues Glu and Asp.

According to one further embodiment of the invention, the linker comprises positively charged amino acid residues.

According to one embodiment of the invention, the linker comprises at least two amino acid residues selected from the group consisting of Lysine or a Lysine derivative or a Lysine mimetic, Arginine, and/or Histidine.

According to one further embodiment of the invention, B is a Cys residue with a free sulfhydryl group.

The free sulfhydryl group of such Cys residue (or derivative) can be used to conjugate a maleimide-comprising linker toxin construct thereto. See FIG. 5 for some more details of the conjugation reaction, and some potential linker constructs.

Toxins comprising a maleimide linker have frequently been used, and also approved by medical authorities, like Adcetris. Thus drugs comprising a MMAE toxin are conjugated to a linker comprising (i) a p-aminobenzyl spacer, (ii) a dipeptide and (iii) a maleimidocaproyl linker, which enables the conjugation of the construct to the free sulfhydryl group of a Cys residue in the antibody.

Providing a Cys-residue in the linker according to the present invention does therefore have the advantage to be able to use off-the-shelf-toxin-maleimide constructs to create antibody-payload conjugates, or, more generally, to be able to fully exploit the advantages of Cys-maleimide binding chemistry. At the same time, off-the-shelf antibodies can be used, which do not have to be deglycosylated.

In specific embodiments, the Cys residue is C-terminal, intrachain or N-terminal in the peptide linker.

According to one further embodiment of the invention, the antibody comprises the Asn residue N297 (EU numbering) in the $C_H2$ domain of the antibody.

According to one further embodiment of the invention, the N297 residue is glycosylated.

According to one further embodiment of the invention, the linker or payload is conjugated to the amide side chain of the Gln residue.

According to one further embodiment of the invention, it is provided that, in case B is a linking moiety, a further step of linking the actual payload to the linking moiety is carried out.

According to one further embodiment of the invention, the microbial transglutaminase is derived from *Streptomyces mobaraensis*, preferentially with a sequence identity of 80% to the native enzyme.

One such Microbial transglutaminase is commercially available from Zedira (Germany). It is recombinantly produced by *E. coli*. *Streptomyces mobaraensis* transglutaminase (UniProtKB-Q6E0Y3 (Q6E0Y3_STRMB) has an amino acid sequence as disclosed in SEQ ID NO 36.

In another embodiment, a microbial transglutaminase *Streptomyces ladakanum* (formerly known as *Streptoverticillium ladakanum* is being used. *Streptomyces ladakanum* transglutaminase (U.S. Pat. No. 6,660,510 B2) has an amino acid sequence as disclosed in SEQ ID NO 37.

Both the above transglutaminases can be sequence modified. In several embodiments, transglutaminases can be used which have 80% or more sequence identity with SEQ ID NO 36 or SEQ ID NO 37.

Another suitable microbial transglutaminase is commercially from Ajinomoto, called ACTIVA TG. In comparison to the transglutaminase from Zedira, ACTIVA TG lacks 4 N terminal amino acids, but has similar activity.

Further microbial transglutaminases which can be used in the context of the present invention are disclosed in Kieliszek and Misiewicz 2014, WO2015191883 A1, WO2008102007 A1 and US20100143970, the content of which is fully incorporated herein by reference.

According to one further embodiment of the invention, the linking moiety B is at least one selected from the group consisting of bioorthogonal marker group other non-bio-orthogonal entities for crosslinking The term "bioorthogonal marker group" has been established by Sletten and Bertozzi (2011) to designate reactive groups that can lead to chemical reactions to occur inside of living systems without interfering with native biochemical processes.

A number of chemical ligation strategies have been developed that fulfill the requirements of bioorthogonality, including the 1,3-dipolar cycloaddition between azides and cyclooctynes (also termed copper-free click chemistry, Baskin et al (2007), between nitrones and cyclooctynes (Ning et al (2010), oxime/hydrazone formation from aldehydes and ketones (Yarema, et al (1998), the tetrazine ligation Blackman et al (2008), the isonitrile-based click reaction (Stockmann et al (2011), and most recently, the quadricyclane ligation (Sletten & Bertozzi (JACS, 2011), Copper(I)-catalyzed azide-alkyne cycloaddition (CuAAC, Kolb & Sharpless 2003), Strain-promoted azide-alkyne cycloaddition (SPAAC, Agard et al 2006), or Strain-promoted alkyne-nitrone cycloaddition (SPANC, MacKenzie et al 2014).

All these documents are incorporated by reference herein to provide sufficient enabling disclosure, and avoid lengthy repetitions.

According to one further embodiment of the invention, the bioorthogonal marker group or the non-bio-orthogonal entity is at least one selected from the group consisting of:

—N—N≡N, or —$N_3$

Lys($N_3$)

Tetrazine

Alkyne

DBCO

BCN

Norborene

Transcyclooctene

—RCOH (aldehyde),

Acyltrifluoroborates,

—SH, and/or

Cysteine

These groups can for example engage in any of the following binding reactions:

TABLE 4

| binding partner 1 | binding partner 2 | reaction type |
|---|---|---|
| —N—N≡N | cyclooctyne derivatives (e.g. DIFO, BCN, DIBAC, DIBO, ADIBO/DBCO) | SPAAC |
| —N—N≡N | Alkyne | CuAAC |
| —N—N≡N | Triarylphosphines | Staudinger ligation |
| tetrazine | Cyclopropene | |
| | Norborene | |
| | Cyclooctyne (BCN) | |
| —SH, e.g., of a Cys residue | Maleimide | Thiol-Maleimide conjugation |
| Amine | N-hydroxysuccinimid | |
| —O-carbamoylhydroxylamines | Acyltrifluoroborates | KAT-ligation (potassium |

TABLE 4-continued

| binding partner 1 | binding partner 2 | reaction type |
|---|---|---|
| $R_1$-N(~~~)-O-C(=O)-N(Et)(Et) | $KF_3B$-C(=O)-~~~ | acyl-trifluoroborate) |
| $R_x$—S—S—$R_y$ | $R_z$—SH + reducing agent (e.g. TCEP, DTT) | Direct disulfide bioconjugation |
| —CHO (aldehyde) | HIPS-probe (indole-hydrazine structure) | Hydrazino-iso-Pictet-Spengler (HIPS) |
| —CHO (aldehyde) | $R_1$—N—N—$R_2$ HO—N—$R_1$ H2N—CHR$_1$—CH2—SH | Hydrazone-ligation Oxime-ligation Thiazolidine-Ligation |
| maleimide | —SH, e.g., of a Cys residue | Thiol-Maleimide conjugation |

In the above table 4, the said linking moieties can either be what is called therein "binding partner 1" or "binding partner 2".

According to one further embodiment of the invention, the payload B is at least one selected from the group consisting of:
- toxin
- cytokine
- growth factor
- radionuclide
- hormone
- anti-viral agent
- anti-bacterial agent
- fluorescent dye
- immunoregulatory/immunostimulatory agent
- half-life increasing moiety
- solubility increasing moiety
- a polymer-toxin conjugate
- a nucleic acid
- a biotin or streptavidin moiety
- a vitamin
- a target binding moiety, and/or
- anti-inflammatory agent.

Half-life increasing moieties are, for example, PEG-moieties (polyethylenglycol moieties; PEGylation), other polymer moieties, PAS moieties (oliogopeptides comporising Proline, Alanine and Serine; PASylation), or Serum albumin binders. Solubility increasing moiety are, for example PEG-moieties (PEGylation) or PAS moieties (PASylation).

Polymer-toxin conjugate are polymers that are capable of carrying many payload molecules. Such conjugates are sometimes also called fleximers, as e.g. marketed by Mersana therapeutics One example of a nucleic acid payload is MCT-485, which is a very small noncoding double stranded RNA which has oncolytic and immune activating properties, developed by MultiCell Technologies, Inc.

Anti-inflammatory agents are for example anti-inflammatory cytokines; which; when conjugated to a target specific antibody, can ameliorate inflammations caused, e.g., by autoimmune diseases.

According to one further embodiment of the invention, the toxin is at least one selected from the group consisting of
- Pyrrolobenzodiazepines (PBD)
- Auristatins (e.g., MMAE, MMAF)
- Maytansinoids (Maytansine, DM1, DM4)
- Duocarmycins
- Tubulysins
- Enediyenes (e.g. Calicheamicin)
- PNUs, doxorubicins
- Pyrrole-based kinesin spindle protein (KSP) inhibitors
- Calicheamicins
- Amanitins (e.g. α-Amanitin), and/or
- Camptothecins (e.g. exatecans, deruxtecans)

The vitamin can be selected from the group consisting of folates, including folic acid, folacin, and vitamin B9.

The target binding moiety can be a protein or small molecule being capable of specifically binding to a protein or non-protein target. In one embodiment, such target binding moiety is a scFv shaped antibody, a Fab fragment, a F(ab)2 fragment, a nanobody, affibody, a diabody, a VHH shaped antibody, or an antibody mimetic, including a DARPIN.

According to one further embodiment of the invention, the antibody is at least one selected from the group consisting of
- IgG, IgE, IgM, IgD, IgA and IgY
- IgG1, IgG2, IgG3, IgG4, IgA1 and IgA, and/or
- a fragment or recombinant variant thereof retaining target binding properties and comprising the $C_H2$ domain The antibody is preferably a monoclonal antibody.

The antibody can be of human origin, but likewise from mouse, rat, goat, donkey, hamster, or rabbit. In case the conjugate is for therapy, a murine or rabbit antibody can optionally be chimerized or humanized.

Fragment or recombinant variants of antibodies comprising the $C_H2$ domain are, for example,
- antibody formats comprising mere heavy chain domains (shark antibodies/IgNAR $(V_H-C_H1-C_H2-C_H3-C_H4-C_H5)_2$ or camelid antibodies/hcIgG $(V_H-C_H2-C_H3)_2)$
- scFv-Fc (VH-VL-$C_H2-C_H3)_2$ Fc fusion peptides, comprising an Fc domain and one or more receptor domains.

The antibody can also be bispecific (e.g., DVD-IgG, crossMab, appended IgG-HC fusion) or biparatopic. See Brinkmann and Kontermann (2017) for an overview.

According to one further embodiment of the invention, the linker has two or more linking moieties B.

In such embodiment, an antibody-payload conjugate can be created with, for example, an antibody to payload ratio of 2, with two payloads conjugated to each Q295 residue.

According to one further embodiment of the invention, the two or more linking moieties B differ from one another.

In such embodiment, a first linking moiety could for example be an azide (N₃), while a second linking moiety could be a tetrazine. Such oligopeptide linker thus allows to conjugate two different payloads to two Gln residues of the antibody, i.e., the Q295 of the $C_H2$ domains of the antibody.

In such way, an antibody payload ratio of 2+2 can be obtained. Using a second payload allows for the development of a completely new class of antibody payload conjugates that go beyond current therapeutic approaches with respect to efficacy and potency.

Such embodiment allows, inter alia, to target two different structures in a cell, like, e.g., the DNA and microtubule. Because some cancers can be resistant to one drug, like e.g., a mirobutule toxin, the DNA-toxin can still kill the cancer cells.

According to another embodiment, two drugs could be used that are only fully potent when they are released at the same time and in the same tissue. This may lead to reduced off-target toxicity in case the antibody is partially degraded in healthy tissues or one drug is pre-maturely lost.

Furthermore, dual-labeled probes can be used for non-invasive imaging and therapy or intra/post-operative imaging/surgery. In such embodiment, a tumor patient can be selected by means of the non-invasive imaging. Then, the tumor can be removed surgically using the other imaging agent (e.g., a fluorescent dye), which helps the surgeon or robot to identify all cancerous tissue.

According to another aspect of the invention, an antibody-payload conjugate is provided which has been generated with a method according to any one of the aforementioned steps.

According to another aspect of the invention, a linker having the peptide structure (shown in N->C direction) is provided:

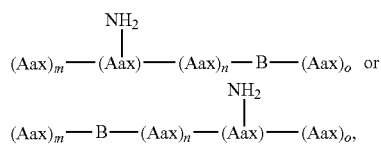

wherein
m is an integer between ≥0 and ≤12
n is an integer between ≥0 and ≤12
o is an integer between ≥0 and ≤12
m+n+o≥0,
Aax can be any naturally or non-naturally occurring L- or D-amino acid, or amino acid derivative or mimetic, and
B is a payload or a linking moiety.

and wherein

is an amino acid, amino acid derivative or amino acid mimetic comprising a side chain having a primary amine group.

Generally, the advantages and embodiments discussed above in accordance with the method of the present invention do also apply to this aspect. i.e., the linker as composition of matter. Hence, those embodiments shall be deemed disclosed also with the linker as composition of matter.

It is important to understand that in different linker peptides shown herein, the C-terminus and/or the N-terminus may or may not be protected, even if shown otherwise. Protection can be accomplished by amidation of the former, and/or acetylation of the latter. In the context of the present invention, both the protected and unprotected linker peptides are encompassed.

In one embodiment thereof,

is Lysine or a Lysine derivative or a Lysine mimetic.

In further embodiments, the linker is not cleavable by cathepsin B, and/or the linker does not comprise a valine-alanine motif or a valine-citrulline motif, and/or the linker does not comprise Polyethylenglycol or a Polyethylenglycol derivative.

According to one embodiment, m+n+o≤25, preferably ≤20, more preferably ≤15, more preferably ≤12, more preferably ≤10, more preferably ≤8, more preferably ≤7, more preferably ≤6, more preferably ≤5, more preferably ≤4.

According to one embodiment, the linking moiety B is at least one selected from the group consisting of
  bioorthogonal marker group
  other non-bio-orthogonal entities for crosslinking According to one embodiment, the bioorthogonal marker group or the non-bio-orthogonal entity is at least one selected from the group consisting of
  —N—N≡N, or —N₃
  Lys(N₃)
  Tetrazine
  Alkyne
  DBCO
  BCN
  Norborene
  Transcyclooctene
  —RCOH (aldehyde),
  Acyltrifluoroborates,
  —SH, and/or
  Cysteine.

In further embodiments, the net charge of the linker is neutral or positive, and/or the linker does not comprise negatively charged amino acid residues, and/or the linker comprises positively charged amino acid residues, and/or the linker comprises at least two amino acid residues selected from the group consisting of
  Lysine or a Lysine derivative or a Lysine mimetic,
  Arginine, and/or
  Histidine.

According to one embodiment the primary amine group is suitable to serve as the substrate of a microbial transglutaminase (MTG).

According to one further embodiment, the linker is suitable for generating an antibody-payload conjugate by means of a microbial transglutaminase (MTG).

According to one further embodiment, the linker is selected from
a) the list as shown in table 5, and/or
b) any one of SEQ ID NO 1-35 and 38-45

According to yet another aspect of the invention, a linker-payload construct is provided, comprising at least
a) a linker according to any the above description, and
b) one or more payloads,
wherein, in said construct, the linker and/or the payload have optionally been chemically modified during binding to allow covalent or non-covalent binding, to form said construct.

In case two or more payloads are being used, the latter can be identical or different from one another.

In one embodiment, the payload is at least one selected from the group consisting of
toxin
cytokine
growth factor
radionuclide
hormone
anti-viral agent
anti-bacterial agent
fluorescent dye
immunoregulatory/immunostimulatory agent
half-life increasing moiety
solubility increasing moiety
a polymer-toxin conjugate
a nucleic acid
a biotin or streptavidin moiety
a vitamin
a target binding moiety, and/or
anti-inflammatory agent.

In another embodiment, the toxin is at least one selected from the group consisting of
Pyrrolobenzodiazepines (PBD)
Auristatins (e.g., MMAE, MMAF)
Maytansinoids (Maytansine, DM1, DM4)
Duocarmycins
Tubulysins
Enediyenes (e.g. Calicheamicin)
PNUs, doxorubicins
Pyrrole-based kinesin spindle protein (KSP) inhibitors
Calicheamicins
Amanitins (e.g. α-Amanitin), and/or
Camptothecins (e.g. exatecans, deruxtecans)

According to another aspect of the invention, an antibody-payload conjugate is provided comprising
a) one or more linker-payload constructs according to the above description, and
b) an antibody comprising at least one Gln residue in the heavy or light chain,
wherein, in said conjugate, the linker-payload constructs and/or the antibody have optionally been chemically modified during conjugation to allow covalent or non-covalent conjugation, to form said conjugate.

According to another aspect of the invention, a pharmaceutical composition is provided, the composition comprising the linker according to the above description, the linker-payload construct according to the above description, and/or the antibody-payload conjugate according to the above description.

According to another aspect of the invention, a pharmaceutical product is provided, the product comprising the antibody-payload conjugate according to the above description, or the pharmaceutical composition according to the above description, and at least one further pharmaceutically acceptable ingredient.

According to another aspect of the invention, the pharmaceutical composition according to the above description or the product according to the above description is provided (for the manufacture of a medicament) for the treatment of a patient
suffering from,
being at risk of developing, and/or
being diagnosed for
a neoplastic disease, neurological disease, an autoimmune disease, an inflammatory disease or an infectious disease, or the prevention or for the prevention of such condition.

According to another aspect of the invention, a method of treating or preventing a neoplastic disease is provided, said method comprising administering to a patient in need thereof the antibody-payload conjugate according to the above description, the pharmaceutical composition according to the above description, or the product according to the above description.

The inflammatory disease can be an autoimmune disease. The infectious disease can be a bacterial infection or a viral infection.

Said conjugate or product is administered to the human or animal subject in an amount or dosage that efficiently treats the disease. Alternatively, a corresponding method of treatment is provided.

The following table 5 shows different linkers that can be used in the context of the present invention, and their SEQ ID Numbers. For the avoidance of doubt, if there is a discrepancy with the electronic WIPO ST 25 sequence listing, the sequences of this table are to be deemed the correct ones.

It is important to understand that in some linker peptides shown herein, the moiety at the C-terminus is simply designated as $N_3$. However, this should be understood as an abbreviation of Lys($N_3$). For example, RAKAR($N_3$) or ArgAlaLysAlaArg($N_3$) does actually mean $RAK_1ARK_2$, with $K_2$=Lys($N_3$), or ArgAlaLysAlaArgLys($N_3$) (SEQ ID NO:1).

It is furthermore important to understand that in different linker peptides shown herein, the C-terminus and/or the N-terminus may or may not be protected, even if shown otherwise.

Protection can be accomplished by amidation of the former, and/or acetylation of the latter. In the context of the present invention, both the protected and unprotected linker peptides are encompassed.

For example RAKARK($N_3$) (SEQ ID NO:1) does indeed encompass four variants, with a) both termini protected as discussed above, b) only the N-terminus or the C-terminus protected as discussed above, or c) both termini unprotected.

On the other hand, $NH_2$-ArgAlaLysLys($N_3$)—COOH (SEQ ID NO:2) for example explicitly specifies a peptide which is not protected, i.e., has unprotected N- and C terminus.

TABLE 5

| FIG. No | Three letter code | One letter code | Linking moiety B | peptide length | number of positive amino acids (Lys/Arg/His)* | SEQ ID No |
|---|---|---|---|---|---|---|
| Linkers with Lys providing primary amine for transglutaminase reaction (in bold print) | | | | | | |
| 2 | ArgAlaLysAlaArgLys(N$_3$) | RAK$_1$ARK$_2$, with K$_2$ = Lys(N$_3$) | Lys(N$_3$) | 6 | 3 | 1 |
| 9, 16 | ArgAlaLysLys(N$_3$) | RAK$_1$K$_2$, with K$_2$ = Lys(N$_3$) | Lys(N$_3$) | 4 | 2 | 2 |
| 9 | ArgAlaLysXaa(N$_3$) | RAKX, with X = Xaa(N$_3$), Xaa is 4-Azido-L-homoalanine | Xaa(N$_3$) | 4 | 2 | 3 |
| 9 | ArgAlaLys[PEG]$_3$(N$_3$) | RAK[PEG]$_3$N$_3$, with [PEG]$_3$ = triethylenglycol | N$_3$ | 5 | 2 | 4 |
| 9 | ArgAlaLysCys | RAKC | Cys-SH | 4 | 2 | 5 |
| 19A | ArgGlyLysLys(N$_3$) | RGK$_1$K$_2$, with K$_2$ = Lys(N$_3$) | Lys(N$_3$) | 4 | 2 | 6 |
| 19A | ArgSerLysLys(N$_3$) | RSK$_1$K$_2$, with K$_2$ = Lys(N$_3$) | Lys(N$_3$) | 4 | 2 | 7 |
| 19A | ArgHisLysLys(N$_3$) | RHK$_1$K$_2$, with K$_2$ = Lys(N$_3$) | Lys(N$_3$) | 4 | 3 | 8 |
| 19A | AlaHisLysLys(N$_3$) | AHK$_1$K$_2$, with K$_2$ = Lys(N$_3$) | Lys(N$_3$) | 4 | 2 | 9 |
| 19A | Lys(N$_3$)ArgAlaLysAlaArg | K$_1$RAK$_2$AR with K$_1$ = Lys(N$_3$) | Lys(N$_3$) | 6 | 3 | 10 |
| 19A | ArgLysArgLys(N$_3$) | RK$_1$RK$_2$ with K$_1$ = Lys(N$_3$) | Lys(N$_3$) | 4 | 3 | 11 |
| Linkers with Lys with primary amine for transglutaminase reaction (in bold print), N- and/or C-terminus not protected | | | | | | |
| 19B | NH$_2$-ArgAlaLysLys(N$_3$)-COOH | NH$_2$-RAK$_1$K$_2$-COOH with K$_1$ = Lys(N$_3$) | Lys(N$_3$) | 4 | 2 | 2 |
| Linkers with amino acid derivative or mimetic (italics), Lys providing primary amine for transglutaminase reaction (in bold print) | | | | | | |
| 18A | Arg*βAla*LysLys(N$_3$) | R*β*AK$_1$K$_2$, with K$_2$ = Lys(N$_3$) | Lys(N$_3$) | 4 | 2 | 12 |
| 18A | *HomoArg*AlaLysLys(N$_3$) | *h*RAK$_1$K$_2$, with K$_2$ = Lys(N$_3$) | Lys(N$_3$) | 4 | 2 | 13 |
| 18A | *homoArgβAla*LysLys(N$_3$) | *hRβ*AK$_1$K$_2$, with K$_2$ = Lys(N$_3$) | Lys(N$_3$) | 4 | 2 | 14 |
| Linkers with amino acid with Lys derivative or mimetic providing primary amine for transglutaminase reaction (in bold print) | | | | | | |
| 18B | ArgAlaOrnLys(N$_3$), Orn = Ornithine | RAoK, with K =Lys(N$_3$) and o =Orn | Lys(N$_3$) | 4 | 2 | 15 |
| 18B | ArgAlaDabLys(N$_3$), Dab = α,γ-diaminobutyric acid | RAdK, with K =Lys(N$_3$) and d = Dab | Lys(N$_3$) | 4 | 2 | 16 |
| 18B | ArgAlaβhLysLys(N$_3$), βhLys = L-β-homolysine ((S)-3,7-Diamino-heptanoic acid | RAβhK$_1$K$_2$, with K$_2$ = Lys(N$_3$) | Lys(N$_3$) | 4 | 2 | 17 |
| 18B | ArgAlahomoLysLys(N$_3$) homoLys = homolysine | RAhK$_1$K$_2$, with K$_2$ = Lys(N$_3$) | Lys(N$_3$) | 4 | 2 | 18 |
| 18C | ArgAladLysLys(N$_3$), dLys = D-Lysine | RAk$_1$K$_2$, with K$_2$ = Lys(N$_3$) and k$_1$ = dLys | Lys(N$_3$) | 4 | 2 | 19 |

TABLE 5-continued

| FIG. No | Three letter code | One letter code | Linking moiety B | peptide length | number of positive amino acids (Lys/Arg/His)* | SEQ ID No |
|---|---|---|---|---|---|---|
| Bifunctional linkers | | | | | | |
| 7A | ArgAlaLysLys(N₃)ArgAlaLys(Tetrazine) | RAK₁K₂RAK₃, with K₂ = Lys(N₃), K₃ = Lys(Tetrazine) | Lys(N₃) and Lys(Tetrazine) | 7 | 3 | 20 |
| 7B | Lys(N₃)CysArgAlaLys | K₁CRAK₂ with K₁ = Lys(N₃) | Lys(N₃), Cys-SH | 5 | 2 | 21 |
| 7C | LysAlaArgCysLys(N₃) | K₁ARCK₂ with K₂ = Lys(N₃) | Lys(N₃), Cys-SH | 5 | 2 | 22 |
| 8A | Lys(N₃)ArgAlaLysAlaArgLys(N₃) | K₁RAK₂ARK₃, with K₁ and K₃ = Lys(N₃)) | Lys(N₃) (2x) | 7 | 3 | 23 |
| 8B | LysAlaArgLys(N₃)Lys(N₃) | K₁ARK₂K₃; with K₂ and K₃ = Lys(N₃) | Lys(N₃) (2x) | 5 | 2 | 24 |
| Other linkers with Lys providing primary amine for transglutaminase reaction (in bold print) | | | | | | |
| 20 | ArgLys(N₃)Lys | RK₁K₂, with K₁ = Lys(N₃)) | Lys(N₃) | 3 | 2 | 38** |
| 20 | LysLys(N₃) | K₁K₂ | Lys(N₃) | 2 | 1 | 39** |
| 20 | LysCys | KC | Cys-SH | 2 | 1 | 40** |
|  | ArgLysArg-B | RKR |  | 3 | 3 | 41** |
|  | ArgHisLys-B | RHK |  | 3 | 3 | 42** |
|  | ArgAlaAlaArgLys-B | RAARK |  | 5 | 3 | 25 |
|  | LysTyrArg-B | KYR |  | 3 | 2 | 43** |
|  | ArgArgLysAlaTyr-B | RRKAY |  | 5 | 3 | 26 |
|  | ArgArgLysAsnTyr-B | RRKNY |  | 5 | 3 | 27 |
|  | LysAlaArgAlaArg-B | KARAR |  | 5 | 3 | 28 |
|  | LysAlaArgAla-B | KARA |  | 4 | 2 | 29 |
|  | ArgAlaLysAlaArg-B | RAKAR |  | 5 | 3 | 30 |
|  | AlaTyrAlaLys-B | AYAK |  | 4 | 1 | 31 |
|  | ArgAlaLysAlaArgGlyLys-B | RAKARGK |  | 7 | 4 | 32 |
|  | ArgAlaLysLysAsnArgAlaLys-B | RAKKNRAK |  | 8 | 5 | 33 |
|  | AsnLysAlaLeuLysAlaPro-B | NKALKAP |  | 7 | 2 | 34 |
|  | AspGlyValGluLysAsnAlaLysThrLysProArg-B | DGVEKNAKTKPR |  | 12 | 4 | 35 |
|  | ArgAlaLys-B | RAK |  | 3 | 2 | 44** |
|  | LysAlaArg-B | KAR |  | 3 | 2 | 45** |
|  | LysAlaHis-B | KAH |  | 3 | 2 | 46 |
|  | LysHisAla-B | KHA |  | 3 | 2 | 47 |
|  | LysGlyHis-B | KGH |  | 3 | 2 | 47 |
|  | LysHisGly-B | KHG |  | 3 | 2 | 48 |
|  | LysAlaAla-B | KAA |  | 3 | 1 | 49 |

TABLE 5-continued

| FIG. No | Three letter code | One letter code | Linking moiety B | peptide length | number of positive amino acids (Lys/Arg/His)* | SEQ ID No |
|---|---|---|---|---|---|---|
| | LysAlaSer-B | KAS | | 3 | 1 | 50 |
| | LysSerAla-B | KSA | | 3 | 1 | 51 |
| | LysSerArg-B | KSR | | 3 | 2 | 52 |
| | LysArgSer-B | KRS | | 3 | 2 | 53 |
| | LysHisArg-B | KHR | | 3 | 2 | 54 |
| | LysArgHis-B | KRH | | 3 | 2 | 55 |
| | LysArgTyr-B | KRY | | 3 | 2 | 56 |
| | LysTyrArg-B | KYR | | 3 | 2 | 57 |
| | LysGlyAla-B | KGA | | 3 | 1 | 58 |
| | LysAlaGly-B | KAG | | 3 | 1 | 59 |
| | LysSerGly-B | KSG | | 3 | 1 | 60 |
| | LysGlySer-B | KGS | | 3 | 1 | 61 |
| | LysAlaAsn-B | KAN | | 3 | 1 | 61 |

*note that Lys(N3) does not qualify as a positively charged amino acid
**Due to a length of max 3 AA. These linkers are not mentioned in the electronic sequence listing

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'->3'.

Example 1: Screening of Linker Library for Suitable Lys Comprising Peptides

Three lysine-containing oligopeptide libraries were screened in order to identify oligopeptide structures that are suitable to accomplish quantitative conjugation (i.e. >95%) to Q295 of native antibodies by means of the Microbial Transglutaminase as discussed herein. Peptides of library 1 were to some extent derived from Caporale et al., 2015 but also own ones were designed, while library 2 and 3 were generated and developed from the gained knowledge of the preceding libraries. A glycosylated IgG (IgG1) was used as the reference antibody.

Reaction conditions were as follows: 1 mg/mL native humanized IgG1 reference antibody, 80 molar excess of the peptide versus the antibody, 6-12 U/ml MTG, 20 h, 37° C., buffer pH 7.6. The reaction mixture was analyzed on a LC-MS-ESI (LCT-Premier, Waters, Milford, United States). For analysis, the antibody-conjugate was reduced with 50 mM DTT (15 min at 37° C.) to separate the light from the heavy chain. This was achieved using liquid chromatography (LC) and an Aeris WIDEPORE XB-C18 column (3.6 µm, 100 mm×2.1 mm; Phenomenex, USA) at a column temperature of 80° C., applying an LC-gradient shown in the following table 6.

TABLE 6

| Time [min] | Water [%] | Acetonitrile [%] | 2-Propanol [%] | Curve |
|---|---|---|---|---|
| 0 | 90 | 10 | 0 | Starting point |
| 3 | 70 | 25 | 5 | linear |
| 15 | 58 | 37 | 5 | linear |
| 20 | 5 | 90 | 5 | linear |

The obtained MS spectra were analyzed using MassLynx V4.1 and deconvoluted using the MaxEnt1 algorithm. The conjugation ratio $R_c$ was calculated as follows:

$$R_c = \frac{\sum (\text{intensity of conjugated peaks})}{\sum (\text{intensity of unconjugated peaks}) + \sum (\text{intensity of conjugated peaks})} \quad (1)$$

FIG. 3 shows the result of screening the three libraries. It was found that positively charged amino acids are favoring the conjugation reaction while negatively charged amino acids often suppress the conjugation reaction. However, negatively charged amino acids can be outbalanced by introduction of a positively charge amino acid. In such, the transglutaminase enzyme accepts such peptide.

These peptides are not functional, i.e. they do not carry the linker moiety, e.g., the bio-orthogonal group, but solely were used to find the lysine-containing peptide that was conjugated with highest efficiency.

The fact that charged oligopeptide structures can efficiently be conjugated to the Q295 of a non-deglycosylated (=native) antibody is advantageous, because it will also allow to attach even the most hydrophobic payloads, such as the pyrrolobenzodiazepine-toxins (PBD-toxins), and keeping them effectively in solution with minimized aggregation potential compared to low-molecular weight substrates with limited hydrophilicity that are based on poly(ethylene glycol).

Example 2: Cell Toxicity Assay

Cell lines and culture: MDA-MB-231, and SK-BR-3 were obtained from the American Type Culture Collection (ATCC) and cultured in RPMI-1640 following standard cell-culture protocols.

SK-BR-3 is a breast cancer cell line isolated by the Memorial Sloan-Kettering Cancer Center in 1970 that is used in therapeutic research, especially in context of HER2 targeting. MDA-MB-231 cells are derived from human breast adenocarcinoma of the "basal" type, and are triple negative (ER, PR and HER2 negative). Adcetris (Brentuximab Vedotin) is a commercially available antibody drug conjugate that targets CD30 and is hence expected to not be active against cells which do not express CD30, e.g., MDA-MB-231, and SK-BR-3. Kadcyla (Trastuzumab emtansin) is a commercially available antibody drug conjugate that targets Her2 and is hence expected to be active against cells which express Her2 (e.g., SK-BR-3), and not active against cells which do not express Her2 (e.g., MDA-MB-231). ADC (in-house) is an antibody drug conjugate produced with the linker technology as specified herein, using a non-deglycosylated antibody, and targets Her2, having a Drug to Antibody Ratio of 2, hence bearing two emtansin (DM-1) molecules. Anti-HER2 mAb is a non-deglycosylated, unconjugated antibody, targeting Her2.

Cell toxicity assay: Cells were seeded into 96 well plates (white walled, clear flat bottom plates) at densities of 10,000 cells per well and incubated overnight at 37° C. and 5% $CO_2$.

Monoclonal antibodies (mAbs) and antibody-drug conjugates (ADCs) were serially diluted 1:4 in media at a starting concentration of 10 μg/mL (66.7 nM). Media was removed from cells, and mAb/ADC dilutions were added. Cells treated with media only served as the reference for 100% viability. Cells were incubated with antibodies for three days at 37° C. and 5% $CO_2$.

Cell viability was assessed by Cell Titer-Glo® (Promega) following manufacturer's instructions and as briefly outlined here. Plates were equilibrated to room temperature for 30 minutes. Cell Titer-Glo® reagent was made by addition of Cell Titer-Glo buffer to substrate. 50 μL per well of Cell Titer-Glo® reagent was added and incubated at room temperature with shaking for two minutes followed by an additional 30 minutes incubation at room temperature. Luminescence was detected on a Perkin Elmer 2030 Multilabel Reader Victor™ X3 plate reader using an integration time of 1 second.

The data were processed as follows: luminescence values of wells treated with media only were averaged and served as the reference for 100% viability. Percent viability of mAb/ADC treated wells was calculated using the following equation:

$$\% \text{ viability} = \left( \frac{\text{Luminescence of treated well}}{\text{Average luminescence of media treated wells}} \right) * 100\%$$

Normalized percent viability was plotted versus the logarithm of mAb/ADC concentration and the data were fit using GraphPad Prism 7.00.

As can be seen in FIG. 22A-22B, ADC (in-house) has the same potency against SK-BR3 cells as Kadcyla. Hence, the advantages provided by the novel linker technology (ease of manufacture, site specificity, stable stoichiometry, no need to deglycosylate that antibody) do not come at any disadvantage regarding the cellular toxicity. This is even more important as the ADC (in-house) has a DAR of 2, while Kadcyla has an average DAR of 3.53±0.05, hence is capable to deliver more toxin to the target cells.

Example 3: Preparation of Site-Specifically Conjugated IgG1 Antibodies

Preparation of site-specifically conjugated IgG1 antibodies that remain native after conjugation (FIG. 10-12). The following conjugation conditions were used: native IgG1s in a standard buffer (1 mg/mL end conc.), 80 equivalents of azide-containing-peptide, 12 U/mL microbial transglutaminase, buffer pH 7.6 (25° C.), 20 h incubation at 37° C. The conjugated antibodies were then purified using a PD10 column followed by a centrifugation step in an Amicon Ultra-4 50 kDa filter. 10 eq DBCO-PEG4-5/6-FAM-dye or 10 eq DBCO-PEG4-5/6-Carboxyrhodamine-dye, dissolved in DMSO, was then added for a click reaction, 4 h at RT in the dark. The clean-up was done with iterative wash steps using buffer pH 7.6 and 50 kDa Amicons. Antibody concentrations were determined by UV-VIS spectrometry. The conjugation quantification was done by LC-MS, using an Aeris WIDEPORE XBC18 column and the conditions mentioned in Example 1.

Example 4: Flow-Cytometry Experiments

SKOV3ip cells (approx. $15*10^6$) got washed with 10 mL PBS (37° C.). The supernatant is discarded and 2.5 mL Accutase was added to lyse the cells from the surface for 10-30 min at 37° C. With additional 7.5 mL PBS the cells got gently pipette-mixed and transferred into a 15 mL Falcon tube. The cells were counted with a Neubauer cell counting chamber. The falcon tube was centrifuged for 5 min at 1000 g, the supernatant discarded and the cell pellet resuspended with ice-cold FACS buffer (PBS+3% FCS). The amount of buffer used corresponds to a concentration of 500'000 cells per 100 uL sample. From now it was worked on ice. 100 uL cells were aliquoted to the control well in a 96-well plate. 5 ug human IgG1 was added and mixed carefully by pipetting. The whole 96-well plate with the cells got incubated for 30 min while gently shaking. After 15 min incubation, a pipette-mixing step was performed. Then, additional 100 uL FACS-Buffer was added to the well and the cells got pelleted 5 min/500 g with a precooled centrifuge at 4° C. The supernatant got discarded and the cells gently resuspended in 200 uL FACS buffer. The cells were pelleted again and the washing procedure repeated for at least one more time. Then, 100 uL FACS buffer was used to resuspend the cells and 1 uL secondary goat anti-human IgG-FITC (1:75 dilution, Santa Cruz Biotechnology, USA) was added. The rest of the other wells were then provided with 100 uL cells. The control wells contained cells only, whereas the sample wells got provided with 5 ug of corresponding antibody (conjugated and clicked IgG1 including isotype IgG1 control). The 30 min incubation step as well as all the washing steps were done like described above. After the second washing step, 120 uL FACS buffer was used to resuspend the pellets to go for flow cytometry analysis with a Guava easyCyte Flow Cytometer (Merck-Millipore, Switzerland). Data were analysed with the FlowJo software (TreeStar Inc, USA). Results are shown in FIG. 13A-13B.

Example 5: Conjugation Efficiency

Peptides were used as obtained and dissolved at a suitable stock concentration (e.g. 25 mM) following the manufacturers instruction, aliquots were prepared and stored at −20° C. Two antibodies of IgG-subclass (antibody 1: anti Her2 IgG1, antibody 2: anti CD38 IgG1) were modified as follows: 1 mg/mL of non-deglycosylated antibody (~6.67 μM) was mixed with 80 molar equivalents of peptide linker (i.e. ~53304), 6 U/mL MTG and buffer. The reaction mixture was incubated for 20 h at 37° C. and then subjected for LC-MS analysis under reducing conditions. For Lys($N_3$)-RAKAR-Lys($N_3$) 12 U/ml MTG was used.

The following table shows the conjugation efficiency of some exemplary linkers according to the present invention:

| Linker | abbreviation | | Conjugation efficiency to Q295 in antibody 1/2 | |
|---|---|---|---|---|
| $NH_2$-(PEG)$_3$-TCO | TCO | Spycher et al., ChemBioChem, 2017 | 18 | 10 |
| $NH_2$-(PEG)$_3$-$N_3$ | PEGA | Lhospice et al., Mol Pharm, 2015 Dennler et al., Bioconj Chem, 2014 | 20 | 21 |
| Biotin cadaverine | BC | Dennler et al., Bioconj Chem, 2014 | 16 | 20 |

None of these linkers provides a primary amine group on amino acid side chain, and, hence, no conjugation to a non-deglycosylated antibody did occur.

Example 6: Dual-Payload Conjugation and Cell-Binding Study 6.1. Preparing Dual-Functionalized Humanized IgG1

IgG1 antibody was incubated for 24 h at 37° C. with 80 eq. Peptide $NH_2$-K($N_3$)CRAK—COOH and 6 U MTG/mg Antibody in buffer pH 7.6. The conjugated antibody was purified from excess linker and MTG enzyme by size exclusion chromatography on a Superdex 16/600 HiLoad 200 column. The fractions were concentrated in Amicon Ultra centrifugal filter units 30 MWCO. The antibody-linker conjugate was then reduced with 30eq Dithiothreitol (DTT), purified followed by exposure to 10 equivalents dehydroascorbic acid for one hour at 8° C. Another cleaning step is done three times as described using Amicon filter tubes of

| FIG. No | Three letter code | One letter code | Linking moiety B | Conjugation efficiency to Q295 in antibody 1/2 | | peptide length | number of positive amino acid residues | SEQ ID NO |
|---|---|---|---|---|---|---|---|---|
| 2 | ArgAlaLysAlaArgLys($N_3$) | RAK$_1$ARK$_2$, with K$_2$ = Lys($N_3$) | Lys($N_3$) | 84% | 82% | 6 | 3 | SEQ ID NO: 23 |
| 9, 16 | ArgAlaLysLys($N_3$) | RAK$_1$K$_2$, with K$_2$ = Lys($N_3$) | Lys($N_3$) | 90% | 90% | 4 | 2 | SEQ ID NO: 2 |
| 19A | ArgGlyLysLys($N_3$) | RGK$_1$K$_2$, with K$_2$ = Lys($N_3$) | Lys($N_3$) | 92% | | 4 | 2 | SEQ ID NO: 6 |
| 19A | ArgSerLysLys($N_3$) | RSK$_1$K$_2$, with K$_2$ = Lys($N_3$) | Lys($N_3$) | 91% | | 4 | 2 | SEQ ID NO: 7 |
| 19A | ArgHisLysLys($N_3$) | RHK$_1$K$_2$, with K$_2$ = Lys($N_3$) | Lys($N_3$) | 88% | | 4 | 2 | SEQ ID NO: 8 |
| 19A | AlaHisLysLys($N_3$) | AHK$_1$K$_2$, with K$_2$ = Lys($N_3$) | Lys($N_3$) | 92% | | 4 | 2 | SEQ ID NO: 9 |
| 19A | Lys($N_3$)ArgAlaLysAlaArg | K$_1$RAK$_2$AR with K$_1$ = Lys($N_3$) | Lys($N_3$) | 83% | | 6 | 3 | SEQ ID NO: 10 |
| 19B | NH2-ArgAlaLysLys($N_3$)-COOH | NH2-RAK$_1$K$_2$-COOH with K$_1$ = Lys($N_3$) | Lys($N_3$) | 93% | | 4 | 2 | SEQ ID NO: 2 |
| 7B | Lys($N_3$)CysArgAlaLys | K$_1$CRAK$_2$ with K$_1$ = Lys($N_3$) | Lys($N_3$), Cys-SH | 85% | | 5 | 2 | SEQ ID NO: 21 |
| 8A | Lys($N_3$)ArgAlaLysArgLys($N_3$) | K$_1$RAK$_2$RK$_3$, with K$_1$ and K$_3$ = Lys($N_3$) | Lys($N_3$) (2x) | 70% | | 7 | 3 | SEQ ID NO: 23 |

As a negative comparison, three linkers were used that are not in accordance with the present invention.

30 MWCO. The antibody-conjugate sample was then incubated with 20 eq. maleimide-NODAGA and put overnight to 8° C. After Amicon-washing to remove excess linker, the sample was incubated with 20 equivalents DBCO-PEG4-Ahx-DM1 for 4 h. After purification, the sample was analyzed with LC-MS. Results are shown in FIGS. 23A-23B.

6.2. Antibody Labeling and Cell-Binding Study (Lindmo-Assay)

70 µl functionalized antibody (1.3 mg/mL) was provided with 15 µL Indium-111 ($^{111}$In) (7.7 MBq), 15 µL HCl 0.05 M, and 30 µL Ammonium carbonate 0.5 M. The mix was incubated for one hour at 37° C. and then six times Amicon 30 MWCO cleaned up. Target expressing cells in a T150 flask were first washed with 10 mL PBS and then detached with 10 mL PBS+1 mM EDTA at 37° C. 10 mL complete cell culture medium was added and the cells were centrifuged in a falcon tube for 5 min at 1000 rpm. The cells were then washed with PBS and then suspended in PBS+1% BSA to a stock solution of 4*106 cells/0.5 mL. The cells were kept on ice for the following steps. Five cell-dilutions (in triplicates) were made from 0.25 Mio cells up to 4 Mio cells in 0.5 mL in a tube. 50 µL labeled antibody (normed to 25,000 cpm) was added to each tube. The control for non-specific binding was first provided with additional 15 µg unlabeled native IgG1-antibody. The tubes were incubated for 30 min at 37° C. and 220 rpm. Subsequently, 2 mL ice cold PBS+1% BSA was added and the samples got centrifuged 5 min at 1500 rpm at 4° C. The supernatant was removed and another 2 mL PBS+1% BSA was added. The centrifugation step was then repeated. After removing the supernatant, the samples were measured on a Gamma counter. The results show that the dual-labeled ADC (conjugated with Maleimide-NODAGA and DBCO-PEG4-Ahx-DM1) yet maintained binding specificity and could efficiently be labeled with Indium-111. Results are shown in FIG. 24.

Example 7: Control Conjugation of Ac-RβAK (N$_3$)—NH$_2$ (Ac-ArgβAlaLys(N$_3$)—NH$_2$) (i.e., a Linker not Containing an Amino Acid with a Primary Amine on a Side Chain) to Humanized IgG1

The conjugation was performed as outlined above in example 5. After LC-MS analysis, no modification of the antibody heavy chain could be detected, as expected. This indicates that MTG selectively reacts with primary amines of, e.g. Lysine residues, or Lysine analogues or mimetics. The amine group on the side chain of Arginine is however part of the guanidine group and hence not a primary amine in the meaning of the present invention. As a consequence, no conjugation to a non-deglycosylated antibody did occur. Results are shown in FIG. 25.

Example 8: Conjugation to Human IgG4 Antibody

Human IgG4 antibody was incubated using Ac-RAKAR-NH$_2$ peptide following the standard conjugation protocol. LC-MS analysis revealed after conjugation that the IgG4 was selectively modified at a single residue only at the heavy chain. Results are shown in FIGS. 26A-26C.

Example 9: ADC Preparation from a Humanized IgG1, Followed by LC-MS 3.9 mg/ml humanized IgG1 antibody was incubated with 2.4 U/mg antibody MTG and 80eq Ac-RAK-Lys(N$_3$)—NH$_2$ in buffer pH 7.6 at 37° C. and after incubation a conjugation ratio of >98% was achieved. After size-exclusion chromatography to remove excess linker and MTG, the sample was concentrated and reacted with 10eq DBCO-PEG4-Ahx-DM1 for 19 h and purified, a clicking efficiency of >98% was achieved. After each step, an LC-MS was done showing thus the assembly of the ADC step-by-step. No modification of the light chain was detected at all the steps. Results are shown in FIG. 27.

Example 10: SEC-MALS Experiments

Antibodies and antibody conjugates (Herceptin, an anti-HER2-mAb-linker construct using the claimed linker technology, an anti-HER2-mAb-linker-DM1 conjugate using the claimed linker technology (elsewhere herein called inhouse ADC), and Kadcyla® were dialyzed against buffer A (buffer A: 20 mM HEPES pH 7.5, 150 mM NaCl) at room temperature for 3 hours. Subsequently, the dialysis buffer was filtered through a 0.1 µm filter. A Superdex® 200 Increase 10/300 GL column was equilibrated overnight at room temperature in filtered dialysis buffer until a stable light scattering baseline was achieved. Samples were diluted to 4 mg/mL in dialysis buffer A and prepared by centrifugation at 13000 RPM for 5 minutes prior to loading 30 µL onto the size exclusion column. The flow rate was set to 0.5 mL/min, and both light scattering and the refractive index were monitored by Wyatt Technologies MiniDAWN TREOS and optilab-t-rex detectors, respectively. ASTRA chromatography software was used for baseline correction and data analysis.

Results are shown in FIG. 28. It can be seen that the Inhouse ADC is nicely defined both in the light scattering experiment (SEC, peak line) as well as in the multi angle light scattering (MALS) experiment (inclined line in the middle). Both values are comparable to naked Herceptin, indicating that there are no fragments or aggregates. The subject linker technology hence delivers, in a simple step, a very pure product. In contrast thereto, Kadcyla, which is conjugated by means of maleimide chemistry, has a broader peak, indicating more fragments and aggregates.

REFERENCES

Dorywalska et al (2015), Site-Dependent Degradation of a Non-Cleavable Auristatin-Based Linker-Payload in Rodent Plasma and Its Effect on ADC Efficacy. PLoS ONE 10(7): e0132282

Dorywalska, M.; et al., Effect of Attachment Site on Stability of Cleavable Antibody Drug Conjugates. Bioconjugate Chemistry 2015, 26 (4), 650-659.

van Geel et al (2015), Chemoenzymatic Conjugation of Toxic Payloads to the Globally Conserved N-Glycan of Native mAbs Provides Homogeneous and Highly Efficacious Antibody-Drug Conjugates Bioconjugate Chem, 26 (11), pp 2233-2242

Sletten, et al., From Mechanism to Mouse: A Tale of Two Bioorthogonal Reactions. Accounts of Chemical Research 2011, 44 (9), 666-676.

Stöckmann et al (2011). "Exploring isonitrile-based click chemistry for ligation with biomolecules". Organic & Biomolecular Chemistry. 9 (21): 7303.

Blackman et al (2008). "The Tetrazine Ligation: Fast Bioconjugation based on Inverse-electron-demand Diels-Alder Reactivity". Journal of the American Chemical Society. 130 (41): 13518-9.

Yarema, et al (1998). "Metabolic Delivery of Ketone Groups to Sialic Acid Residues. Application To Cell Surface Glycoform Engineering". Journal of Biological Chemistry. 273 (47): 31168-79.

Ning et al (2010). "Protein Modification by Strain-Promoted Alkyne-Nitrone Cycloaddition". Angewandte Chemie International Edition. 49 (17): 3065.

Sletten, et al., A Bioorthogonal Quadricyclane Ligation. J Am Chem Soc 2011,133 (44), 17570-17573.

Baskin et al (2007). "Copper-free click chemistry for dynamic in vivo imaging". Proceedings of the National Academy of Sciences. 104 (43): 16793-7.

MacKenzie, D A; Sherratt, A R; Chigrinova, M; Cheung, L L; Pezacki, J P (August 2014). "Strain-promoted cycloadditions involving nitrones and alkynes-rapid tunable reactions for bioorthogonal labeling". Curr Opin Chem Biol. 21: 81-8.

Agard, N. J.; Baskin, J. M.; Prescher, J. A.; Lo, A.; Bertozzi, C. R. (2006). "A Comparative Study of Bioorthogonal Reactions with Azides". ACS Chem. Biol. 1: 644-648

Kolb, H. C.; Sharpless, B. K. (2003). "The growing impact of click chemistry on drug discovery". Drug Discov Today. 8 (24): 1128-1137.

Lhospice et al., Site-Specific Conjugation of Monomethyl Auristatin E to Anti-Cd30 Antibodies Improves Their Pharmacokinetics and Therapeutic Index in Rodent Models, Mol Pharm 12 (6), 1863-1871.2015

Jeger et al, Site-specific and stoichiometric modification of antibodies by bacterial transglutaminase. Angew Chem Int Ed Engl. 2010 Dec. 17; 49(51):9995-7

Strop, et al., Versatility of Microbial Transglutaminase. Bioconjugate Chemistry 2014, 25 (5), 855-862.

Spycher et al., Dual Site-Specifically Modified Antibodies With Solid-Phase Immobilized Microbial Transglutaminase. Chembiochem. 2017 Aug. 3; 18(19): 1923-1927

Dennler et al., Transglutaminase-based chemo-enzymatic conjugation approach yields homogeneous antibody-drug conjugates. Bioconjug Chem. 2014 Mar. 19; 25(3):569-78

Dennler et al. Microbial transglutaminase and c-myc-tag: a strong couple for the functionalization of antibody-like protein scaffolds from discovery platforms. Chembiochem. 2015 Mar. 23; 16(5):861-7

Mindt, et al., Modification of different IgG1 antibodies via glutamine and lysine using bacterial and human tissue transglutaminase. Bioconjugate chemistry 2008, 19 (1), 271-8.

Azhdarinia, et al., Dual-labeling strategies for nuclear and fluorescence molecular imaging: a review and analysis. Mol Imaging Biol 2012, 14 (3), 261-76.

Dubowchik et al., Cathepsin B-labile dipeptide linkers for lysosomal release of doxorubicin from internalizing immunoconjugates: model studies of enzymatic drug release and antigen-specific in vitro anticancer activity. Bioconjug Chem. 2002 July-August; 13(4):855-69.

Zheng, et al., The impact of glycosylation on monoclonal antibody conformation and stability. Mabs-Austin 2011, 3 (6), 568-576.

Subedi, et al., The Structural Role of Antibody N-Glycosylation in Receptor Interactions. Structure 2015, 23 (9), 1573-1583.

Caporale, et al., The LQSP tetrapeptide is a new highly efficient substrate of microbial transglutaminase for the site-specific derivatization of peptides and proteins. Biotechnol J 2015, 10 (1), 154-161.

Kieliszek and Misiewicz, Folia Microbiol (Praha). 2014; 59(3): 241-250

Brinkmann and Kontermann, The making of bispecific antibodies. MAbs. 2017 February-March; 9(2): 182-212.

Azhdarinia A. et al., Dual-Labeling Strategies for Nuclear and Fluorescence Molecular Imaging: A Review and Analysis. Mol Imaging Biol. 2012 June; 14(3): 261-276.

Houghton J L. et al., Site-specifically labeled CA19.9-targeted immunoconjugates for the PET, NIRF, and multimodal PET/NIRF imaging of pancreatic cancer. Proc Natl Acad Sci USA. 2015 Dec. 29; 112(52):15850-5

Levengood M. et al., Orthogonal Cysteine Protection Enables Homogeneous Multi-Drug Antibody-Drug Conjugates Angewandte Chemie, Volume 56, Issue 3, Jan. 16, 2017

DISCLAIMER

It is important to understand that in some linker peptides shown herein, the moiety at the C-terminus is simply designated as N3. However, this should be understood as an abbreviation of Lys(N$_3$). For example, RAKAR(N$_3$) or ArgAlaLysAlaArg(N$_3$) does actually mean RAK$_1$ARK$_2$, with K$_2$=Lys(N$_3$), or ArgAlaLysAlaArgLys(N$_3$) (SEQ ID NO:1).

It is furthermore important to understand that in different linker peptides shown herein, the C-terminus and/or the N-terminus may or may not be protected, even if shown otherwise. Protection can be accomplished by amidation of the former, and/or acetylation of the latter. In the context of the present invention, both the protected and unprotected linker peptides are encompassed. For example RAKARK (N$_3$) does indeed encompass four variants, with a) both termini protected as discussed above, b) only the N-terminus or the C-terminus protected as discussed above, or c) both termini unprotected.

What is claimed is:

1. An antibody conjugate comprising
   a) one or more linker constructs comprising a linker having the peptide structure (shown in N->C direction):

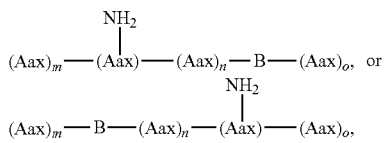

and
   b) an antibody comprising at least one Gln residue (Q295) at position 295 (EU numbering) of the CH2 domain of the antibody, wherein the antibody is N-glycosylated in position N297 (EU numbering) of the CH2 domain;
   wherein:
   m is an integer between ≥0 and ≤12;
   n is an integer between ≥0 and ≤12;
   o is an integer between ≥0 and ≤12;
   m+n+o is an integer between ≥1 and ≤12;
   Aax is any naturally or non-naturally occurring L- or D-amino acid, or amino acid derivative or mimetic;

is a lysine or a lysine derivative or a lysine mimetic having a primary amine group;
   B is a payload or a linking moiety
   and wherein:
   the linker construct is conjugated to the Gln residue Q295 of the CH2 domain of the antibody via the primary amine group of

2. A pharmaceutical composition comprising the antibody conjugate according to claim 1.

3. A pharmaceutical product comprising the antibody conjugate according to claim 1 and at least one additional pharmaceutically acceptable ingredient.

4. The antibody conjugate according to claim 1, wherein the linker is selected from the group consisting of any one of SEQ ID NOs: 2, 6-10, 21, and 23.

5. The antibody conjugate according to claim 1, wherein the linker has a sequence according to SEQ ID NO: 2.

6. The antibody conjugate according to claim 1, wherein the payload is selected from the group consisting of a toxin, a cytokine, a growth factor, a radionuclide, a hormone, an anti-viral agent, an anti-bacterial agent, a fluorescent dye, an immunoregulatory/immunostimulatory agent, a half-life increasing moiety, a solubility increasing moiety, a polymer-toxin conjugate, a nucleic acid, a biotin or streptavidin moiety, a vitamin, a target binding moiety, and/or an anti-inflammatory agent.

7. The antibody conjugate according to claim 6, wherein the payload is a toxin selected from the group consisting of a pyrrolobenzodiazepine, an auristatin, a maytansinoid, a duocarmycin, a tubulysin, an enediyene, a PNU and/or a doxorubicin, a pyrrole-based kinesin spindle protein (KSP) inhibitor, a calicheamicin, an amanitins, and/or a camptothecin.

8. The antibody conjugate according to claim 7, wherein the payload B is an auristatin.

9. The antibody conjugate according to claim 8, wherein the auristatin is selected from the group consisting of MMAE and MMAF.

10. The antibody conjugate according to claim 1, wherein the linker is not cleavable by cathepsin B.

11. The antibody conjugate according to claim 1, wherein m+n+o≤12.

12. The antibody conjugate according to claim 1, wherein the net charge of the linker is neutral or positive.

13. The antibody conjugate according to claim 1, wherein the linker is selected from the group consisting of any one of SEQ ID NOs: 1-35, or wherein the linker is selected from the group consisting of:
ArgLys(N$_3$)Lys,
LysLys(N$_3$),
LysCys,
ArgLysArg-B,
ArgHisLys-B,
LysTyrArg-B, ArgAlaLys-B,
LysAlaArg-B,
LysAlaHis-B,
LysHisAla-B,
LysGlyHis-B,
LysHisGly-B,
LysAlaAla-B,
LysAlaSer-B,
LysSerAla-B,
LysSerArg-B,
LysArgSer-B,
LysHisArg-B,
LysArgHis-B,
LysArgTyr-B,
LysTyrArg-B,
LysGlyAla-B,
LysAlaGly-B,
LysSerGly-B,
LysGlySer-B, and
LysAlaAsn-B.

14. The antibody conjugate of claim 1, wherein the linker does not comprise negatively charged amino acid residues.

15. The antibody conjugate of claim 1, wherein the linker comprises at least two amino acid residues selected from the group consisting of lysine or a lysine derivative or a lysine mimetic, arginine, and histidine.

16. The antibody conjugate of claim 1, wherein when B is a payload, the linker construct comprises one or more additional payloads.

17. The antibody conjugate of claim 1, wherein when B is a linking moiety, the linking moiety is linked to a payload.

18. The antibody conjugate of claim 17, wherein the linker construct comprises one or more additional payloads.

19. The antibody conjugate of claim 1, wherein in said linker constructs, the linker and/or the payload have been chemically modified during binding to allow covalent or non-covalent binding to form said constructs.

20. The antibody conjugate of claim 1, wherein in said conjugate, the linker-payload constructs and/or the antibody have been chemically modified during conjugation to allow covalent or non-covalent conjugation to form said conjugate.

21. The antibody conjugate according to claim 1, wherein the linker does not comprise a valine-alanine motif or a valine-citrulline motif.

22. The antibody conjugate according to claim 1, wherein the linker does not comprise polyethylenglycol or a polyethylenglycol derivative.

23. The antibody conjugate according to claim 1, wherein $m+n+o \leq 10$.

24. The antibody conjugate according to claim 1, wherein $m+n+o \leq 8$.

25. The antibody conjugate according to claim 1, wherein $m+n+o \leq 7$.

26. The antibody conjugate according to claim 1, wherein $m+n+o \leq 6$.

27. The antibody conjugate according to claim 1, wherein $m+n+o \leq 5$.

28. The antibody conjugate according to claim 1, wherein $m+n+o \leq 4$.

29. The antibody conjugate according to claim 1, wherein $m+n+o \leq 3$.

30. The antibody conjugate according to claim 1, wherein $m+n+o \leq 2$.

31. The antibody conjugate according to claim 1, wherein

is lysine.

* * * * *